(12) United States Patent
Keim et al.

(10) Patent No.: US 9,238,844 B2
(45) Date of Patent: Jan. 19, 2016

(54) COMPOSITIONS AND METHODS TO DETECT INFLUENZA VARIANTS

(75) Inventors: Paul Keim, Flagstaff, AZ (US); David Engelthaler, Flagstaff, AZ (US); Elizabeth Driebe, Flagstaff, AZ (US); Cindy Liu, Flagstaff, AZ (US)

(73) Assignees: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(*) Notice: Subject to any disclaimer, the term of this patent is extended or adjusted under 35 U.S.C. 154(b) by 663 days.

(21) Appl. No.: 12/908,536

(22) Filed: Oct. 20, 2010

(65) Prior Publication Data

US 2011/0092385 A1  Apr. 21, 2011

Related U.S. Application Data

(60) Provisional application No. 61/253,794, filed on Oct. 21, 2009.

(51) Int. Cl.
*C12Q 1/70* (2006.01)
*C12P 19/34* (2006.01)
*C12Q 1/68* (2006.01)

(52) U.S. Cl.
CPC .............. *C12Q 1/701* (2013.01); *C12Q 1/6851* (2013.01); *C12Q 2561/113* (2013.01)

(58) Field of Classification Search
CPC .............................. C12Q 1/701; C12Q 1/6883
See application file for complete search history.

(56) References Cited

U.S. PATENT DOCUMENTS 7,972,786 B2 * 7/2011 Hartshorn et al. ........... 435/6.12
8,354,230 B2 * 1/2013 Chen et al. ................... 435/6.12
2009/0305274 A1 * 12/2009 Gygax et al. .................... 435/6

OTHER PUBLICATIONS

Saito et al. Detection of amantadine-resistant influenza A virus strains in nursing homes by PCR-restriction fragment length polymorphism analysis with nasopharyngeal swabs. J. Clinical Microbiol. (2002) vol. 40, No. 1, pp. 84-88.*
Stephenson et al. Neuraminidase inhibitor resistance after oseltamivir treatment of acute influenza A and B in children. Clinical Infectious Diseases (2009) vol. 48, pp. 389-396.*
Lowe et al. A computer program for selection of oligonucleotide primers for polymerase chain reactions. Nucleic Acids Res. (1990) Vo. 18, No. 7, pp. 1757-1761).*
Hata et al. High frequency of amantadine-resistant influenza A (H3N2) viruses in the 2005-2006 season and rapid detection of amantadine-resistant influenza A (H3N2) viruses by MAMA-PCR. Japanese J. Infectious Dis. (2007) 60:202-204.*

* cited by examiner

*Primary Examiner* — Kenneth R. Horlick
*Assistant Examiner* — David Thomas

(57) ABSTRACT

Methods and kits used in the detection of variants of the Influenza virus are disclosed, including variants that are resistant to treatment with antiviral compositions.

29 Claims, 49 Drawing Sheets

**Key is the difference in amplification across two different templates, mutant vs wild-type. Must have this difference to quantify minor component.

** No difference between wt and mutant primer across alternate mutant template, so not able to quantify alternate mutant with MAMA assay.

SEQUENCE LISTING

```
<160> NUMBER OF SEQ ID NOS: 22

<210> SEQ ID NO 1
<211> LENGTH: 27
<212> TYPE: DNA
<213> ORGANISM: Influenza A virus

<400> SEQUENCE: 1
tgctgttcct kycgataytc ttccctc                                      27

<210> SEQ ID NO 2
<211> LENGTH: 26
<212> TYPE: DNA
<213> ORGANISM: Influenza A virus

<400> SEQUENCE: 2
cagatgcaac gattcaagtg ayccgc                                       26

<210> SEQ ID NO 3
<211> LENGTH: 29
<212> TYPE: DNA
<213> ORGANISM: Influenza A virus

<400> SEQUENCE: 3
gtgcagatgc aacgattcaa gtgaycttt                                    29

<210> SEQ ID NO 4
<211> LENGTH: 19
<212> TYPE: DNA
<213> ORGANISM: Influenza A virus

<400> SEQUENCE: 4
cttctacgga aggagtacc                                               19

<210> SEQ ID NO 5
<211> LENGTH: 26
<212> TYPE: DNA
<213> ORGANISM: Influenza A virus

<400> SEQUENCE: 5
cttgaaaatt tgcagrccta tcagaa                                       26

<210> SEQ ID NO 6
<211> LENGTH: 23
<212> TYPE: DNA
<213> ORGANISM: Influenza A virus
```

<400> SEQUENCE: 6
cccaatgata ytygcrgcaa cta                                          23

<210> SEQ ID NO 7
<211> LENGTH: 22
<212> TYPE: DNA
<213> ORGANISM: Influenza A virus

<400> SEQUENCE: 7
ccaatgatay tygcrgcaac tg                                           22

<210> SEQ ID NO 8
<211> LENGTH: 18
<212> TYPE: DNA
<213> ORGANISM: Influenza A virus

<400> SEQUENCE: 8
caacgattca agtgaccc                                                18

<210> SEQ ID NO 9
<211> LENGTH: 28
<212> TYPE: DNA
<213> ORGANISM: Influenza A virus

<400> SEQUENCE: 9
cttgaaaatt tgcagaccta tcagaaac                                     28

<210> SEQ ID NO 10
<211> LENGTH: 26
<212> TYPE: DNA
<213> ORGANISM: Influenza A virus

<400> SEQUENCE: 10
aagtgcaaga tcccaatgat artcac                                       26

<210> SEQ ID NO 11
<211> LENGTH: 26
<212> TYPE: DNA
<213> ORGANISM: Influenza A virus

<400> SEQUENCE: 11
aagtgcaaga tcccaatgat artcat                                       26

<210> SEQ ID NO 12
<211> LENGTH: 17
<212> TYPE: DNA
<213> ORGANISM: Influenza A virus

<400> SEQUENCE: 12
atgcaacgat tcaagtg                                                 17

<210> SEQ ID NO 13
<211> LENGTH: 29
<212> TYPE: DNA
<213> ORGANISM: Influenza A virus

<400> SEQUENCE: 13
caatatcaag tgcaagatcc caatgatgc                                    29

<210> SEQ ID NO 14
<211> LENGTH: 29
<212> TYPE: DNA
<213> ORGANISM: Influenza A virus

<400> SEQUENCE: 14
caatatcaag tgcaagatcc caatgatgt                                              29

<210> SEQ ID NO 15
<211> LENGTH: 25
<212> TYPE: DNA
<213> ORGANISM: Influenza A virus

<400> SEQUENCE: 15
tcatgtttca ccataatgac cgatg                                                  25

<210> SEQ ID NO 16
<211> LENGTH: 26
<212> TYPE: DNA
<213> ORGANISM: Influenza A virus

<400> SEQUENCE: 16
gggtaacagg aacattcctc atattg                                                 26

<210> SEQ ID NO 17
<211> LENGTH: 27
<212> TYPE: DNA
<213> ORGANISM: Influenza A virus

<400> SEQUENCE: 17
tgggtaacag gaacattcct catagta                                                27

<210> SEQ ID NO 18
<211> LENGTH: 19
<212> TYPE: DNA
<213> ORGANISM: Influenza A virus

<400> SEQUENCE: 18
taaccttccc cttttcgat                                                         19

<210> SEQ ID NO 19
<211> LENGTH: 97
<212> TYPE: PRT
<213> ORGANISM: Influenza A virus

<400> SEQUENCE: 19

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Val His Leu Ile Leu Trp Ile Ile Asp Arg Leu Phe Ser
        35                  40                  45

Lys Ser Ile Tyr Arg Ile Phe Lys His Gly Leu Lys Arg Gly Pro Ser
    50                  55                  60

Thr Glu Gly Val Pro Glu Ser Met Arg Glu Glu Tyr Arg Glu Glu Gln
65                  70                  75                  80

Gln Asn Ala Val Asp Ala Asp Asp Gly His Phe Val Ser Ile Glu Leu
                85                  90                  95

Glu

<210> SEQ ID NO 20
<211> LENGTH: 294
<212> TYPE: DNA
<213> ORGANISM: Influenza A virus -continued

<400> SEQUENCE: 20

```
atgagtcttc taaccgaggt cgaaacgcct atcagaaacg aatggggtg cagatgcaac      60
gattcaagtg atcctcttgt tgttgccgca agtataattg ggattgtgca cctgatattg    120
tggattattg atcgccttt ttccaaaagc atttatcgta tctttaaaca cggttaaaa      180
agagggcctt ctacggaagg agtaccagag tctatgaggg aagaatatcg agaggaacag    240
cagaatgctg tggatgctga cgatggtcat tttgtcagca tagagctgga gtaa          294
```

<210> SEQ ID NO 21
<211> LENGTH: 469
<212> TYPE: PRT
<213> ORGANISM: Influenza A virus

<400> SEQUENCE: 21

```
Met Asn Pro Asn Gln Lys Ile Ile Thr Ile Gly Ser Ile Ser Ile Ala
  1               5                  10                  15

Ile Gly Ile Ile Ser Leu Met Leu Gln Ile Gly Asn Ile Ile Ser Ile
             20                  25                  30

Trp Ala Ser His Ser Ile Gln Thr Gly Ser Gln Asn His Thr Gly Val
         35                  40                  45

Cys Asn Gln Arg Ile Ile Thr Tyr Glu Asn Ser Thr Trp Val Asn His
     50                  55                  60

Thr Tyr Val Asn Ile Asn Asn Thr Asn Val Val Ala Gly Lys Asp Lys
 65                  70                  75                  80

Thr Ser Val Thr Leu Ala Gly Asn Ser Ser Leu Cys Ser Ile Ser Gly
                 85                  90                  95

Trp Ala Ile Tyr Thr Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Leu Gly Glu Ala Pro Ser Pro Tyr Asn Ser Lys Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Glu Thr Ile Lys Ser Trp Lys Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Ala Ala Ser Tyr Lys Ile Phe
                245                 250                 255

Lys Ile Glu Lys Gly Lys Val Thr Lys Ser Ile Glu Leu Asn Ala Pro
            260                 265                 270

Asn Phe His Tyr Glu Glu Cys Ser Cys Tyr Pro Asp Thr Gly Thr Val
        275                 280                 285

Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320
```

```
Val Phe Gly Asp Asn Pro Arg Pro Lys Asp Gly Glu Gly Ser Cys Asn
                325                 330                 335

Pro Val Thr Val Asp Gly Ala Asp Gly Val Lys Gly Phe Ser Tyr Lys
            340                 345                 350

Tyr Gly Asn Gly Val Trp Ile Gly Arg Thr Lys Ser Asn Arg Leu Arg
        355                 360                 365

Lys Gly Phe Glu Met Ile Trp Asp Pro Asn Gly Trp Thr Asp Thr Asp
    370                 375                 380

Ser Asp Phe Ser Val Lys Gln Asp Val Val Ala Ile Thr Asp Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Val Arg Gly Leu Pro Arg
            420                 425                 430

Glu Asn Thr Thr Ile Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp
465

<210> SEQ ID NO 22
<211> LENGTH: 1457
<212> TYPE: DNA
<213> ORGANISM: Influenza A virus

<400> SEQUENCE: 22
agcaaaagca ggagtttaaa atgaacccaa atcaaaagat aataaccatt ggatcaatca      60
gtatagcaat cggaataatt agtctaatgt tgcaaatagg aaatattatt caatatgggg     120
ctagtcactc aatccaaact ggaagtcaaa acaacactgg aatatgcaac caaagaatca     180
tcacatatga aaacagcacc tgggtgaatc acacatatgt taatattaac aacactaaag     240
ttgttgctgg agaggacaaa acttcagtga cattggccgg caattcatct ctttgttcta     300
tcagtggatg gctatatac acaaaagaca cagcataag aattggctcc aaaggagatg     360 ttttttgtcat aagagaacct ttcatatcat gttctcactt ggaatgcaga accttttttc     420
tgacccaagg cgctctatta aatgacaaac attcaaatgg accgtaaag acagaagtc     480 cttatagggc cttaatgagc tgtcctctag gtgaagctcc gtccccatac aattcaaagt     540
tcgaatcagt tgcatggtca gcaagcgcat gccatgatgg catgggctgg ttaacaatcg     600
gaatttctgg tccagacaat ggagctgtgg ctgtactaaa atacaacgga ataataactg     660
gaaccataaa aagttggaaa aagcaaatat taagaacaca agagtctgaa tgtgtctgta     720
tgaacgggtc atgtttcacc ataatgaccg atggcccgag taataaggcc gcctcttaca     780
aaattttcaa gatcgaaaag gggaaggtta ctaaatcaat agagttgaat gcacccaatt     840
tttattatga ggaatgctcc tgttacccag acactggcat agtgatgtgt gtatgcaggg     900
acaactggca tggttcaaat cgaccttggg tgtctttaa tcaaaacttg gattatcaaa     960
taggatacat ctgcagtgga gtgtttggtg acaatccgcg tcccgaagat ggagagggca    1020
gctgcaatcc agtgactgtt gatggagcaa acggagtaaa agggttttca tacaaatatg    1080 gtaatgggt ttggatagga aggaccaaaa gtaacagact tagaaagggg tttgagatga    1140
tttgggatcc taatgatgg acaaataccg cagtgattc tcagtgaaaa caggatgttg    1200
tagcaataac tgattggtca gggtacagcg gaagtttcgt ccaacatcct gagttaacag    1260
```

```
gattggactg tataagacct tgcttctggg ttgagttagt cagagggctg cctagagaaa    1320
atacaacaat ctggactagt gggagcagca tttcttttg tggcgttaat agtgatactg     1380
caaactggtc ttggccagac ggtgctgagt tgccgttcac catcgacaag tagttcgttg    1440
aaaaaactcc ttgtttc                                                   1457
```

COMPOSITIONS AND METHODS TO DETECT INFLUENZA VARIANTS

CLAIM OF PRIORITY

This application claims the benefit of U.S. Provisional Application No. 61/253,794, filed on 21 Oct. 2009, the entirety of which is incorporated by reference into this application.

BACKGROUND OF THE INVENTION

Influenza surveillance and therapy requires monitoring of subpopulations of influenza resistant to antiviral drugs. Assays that track such subpopulations should rapidly, quantitatively, sensitively and specifically detect the subpopulations in mixed concentrations of antiviral sensitive viruses.

BRIEF SUMMARY OF THE INVENTION

The present invention provides among other things: compositions and methods used to detect Influenza virus variants.

It is an object of the invention to characterize minor components in influenza viral mixtures.

It is an object of the invention to characterize mutations that confer antiviral resistance.

It is an object of the invention to provide a highly sensitive and specific set of allele-specific PCR assays capable of characterizing the frequency of mutation for SNP minor components in influenza virus mixtures across a wide range of DNA concentrations.

It is an object of the invention to provide an assay to detect subtypes, variants, mutants or other forms of Influenza virus that are resistant to antiviral drugs.

It is an object of the invention to provide an assay to detect antiviral resistant forms of influenza that is easily translatable for clinical and public health diagnostic use.

It is an object of the invention to provide an assay to detect antiviral resistant forms of influenza that can be adapted to a diverse group of strains and subtypes.

It is an object of the invention to calculate the amount of Influenza A virus resistant to an antiviral composition in a sample.

It is an object of the invention to detect Influenza A virus variants resistant to antiviral compositions in a sample.

It is an object of the invention to provide kits used in calculating the amount of Influenza A virus resistant to antiviral compositions in a sample.

The above and other objects may be achieved through the use of methods involving isolating a nucleic acid from a sample, adding a first oligonucleotide capable of binding to a marker selected from the group consisting of SEQ ID NO. 21 and SEQ ID NO. 22 to a mixture comprising the nucleic acid, subjecting the mixture to conditions that allow nucleic acid amplification, and classifying the strain into a cohort selected from the following cohorts: viruses resistant to antiviral compositions, and viruses sensitive to antiviral compositions. The classification is performed on the basis of a result of the nucleic acid amplification. The first oligonucleotide includes a sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, and SEQ ID NO. 18. If the first oligonucleotide includes SEQ ID NO. 1, a second oligonucleotide may be added to the mixture. The second oligonucleotide may be any oligonucleotide that binds to the marker, such as an oligonucleotide that includes SEQ ID NO. 2 or SEQ ID NO. 3. The method may further comprise adding a third oligonucleotide to the mixture, which may be any oligonucleotide, such as an oligonucleotide that includes SEQ ID NO. 4. If the second oligonucleotide includes SEQ ID NO. 2, then the method may further comprise adding a fourth oligonucleotide to the mixture, such as an oligonucleotide that includes SEQ ID NO. 3. If the first oligonucleotide includes SEQ ID NO. 5, a second oligonucleotide may be added to the mixture. The second oligonucleotide may be any oligonucleotide that binds to the marker, such as an oligonucleotide that includes SEQ ID NO. 6, SEQ ID NO. 7, SEQ ID NO. 13, or SEQ ID NO. 14. The method may further comprise adding a third oligonucleotide to the mixture, which may be any oligonucleotide, such as an oligonucleotide that includes SEQ ID NO. 8. If the second oligonucleotide includes SEQ ID NO. 6, then the method may further comprise adding a fourth oligonucleotide to the mixture, such as an oligonucleotide that includes SEQ ID NO. 7. If the second oligonucleotide includes SEQ ID NO. 13, then the method may further comprise adding a fourth oligonucleotide to the mixture, such as an oligonucleotide that includes SEQ ID NO. 14. If the first oligonucleotide includes SEQ ID NO. 9, a second oligonucleotide may be added to the mixture. The second oligonucleotide may be any oligonucleotide that binds to the marker, such as an oligonucleotide that includes SEQ ID NO. 10 or SEQ ID NO. 11. The method may further comprise adding a third oligonucleotide to the mixture, which may be any oligonucleotide, such as an oligonucleotide that includes SEQ ID NO. 12. If the second oligonucleotide includes SEQ ID NO. 10, then the method may further comprise adding a fourth oligonucleotide to the mixture, such as an oligonucleotide that includes SEQ ID NO. 11. If the first oligonucleotide includes SEQ ID NO. 15, a second oligonucleotide may be added to the mixture. The second oligonucleotide may be any oligonucleotide that binds to the marker, such as an oligonucleotide that includes SEQ ID NO. 16 or SEQ ID NO. 17. The method may further comprise adding a third oligonucleotide to the mixture, which may be any oligonucleotide, such as an oligonucleotide that includes SEQ ID NO. 18. If the second oligonucleotide includes SEQ ID NO. 16, then the method may further comprise adding a fourth oligonucleotide to the mixture, such as an oligonucleotide that includes SEQ ID NO. 17. The first oligonucleotide may comprise a first label. The first label may be any label such as a fluorescent label. An oligonucleotide comprising a fluorescent label may be any oligonucleotide including, for example, SEQ ID NO. 4, SEQ ID NO. 8, SEQ ID NO. 12, and SEQ ID NO. 18. The fluorescent label may be any fluorescent label including FAM, dR110, 5-FAM, 6FAM, dR6G, JOE, HEX, VIC, TET, dTAMRA, TAMRA, NED, dROX, PET, BHQ+, Gold540, and LIZ. The result may be any result including a $\Delta Ct_{r-s}$ value. If the first oligonucleotide includes a sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, and SEQ ID NO. 14, then the antiviral composition may comprise adamantine. If the first oligonucleotide includes a sequence selected from the group consisting of SEQ ID NO. 15, SEQ ID NO. 16, SEQ ID NO. 17, and SEQ ID NO. 18, then the antiviral composition may comprise a neuraminidase inhibitor. The sample may be any sample including an environmental sample or a sample derived from a subject, such as a sputum sample.

The above and other objects may be achieved through the use of methods involving adding a first reagent capable of detecting a mutation in a codon selected from the group consisting of position 26 of SEQ ID NO. 19, the codon encoding position 27 of SEQ ID NO. 19, the codon encoding position 30 of SEQ ID NO. 19, the codon encoding position 31 of SEQ ID NO. 19, and the codon encoding position 275 of SEQ ID NO. 21 to a mixture comprising the sample, and assigning the sample to a cohort on the basis of the binding of the reagent to the sample, wherein the cohort is selected from the group consisting of a cohort with virus resistant to an antiviral composition and a cohort with virus sensitive to an antiviral composition. The mutation may be any mutation in the above positions including a mutation that results in an amino acid change selected from the group consisting of L26F in SEQ ID NO. 19, V27A in SEQ ID NO. 19, A30T in SEQ ID NO. 19, S31N in SEQ ID NO. 19, and H275Y in SEQ ID NO. 21. The first reagent may comprise a nucleic acid. Examples include nucleic acids selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, and SEQ ID NO. 18. The mixture may be subjected to nucleic acid amplification. The mixture may be subjected to conditions that allow nucleic acid sequencing. The first reagent may be affixed to a solid substrate. The first reagent may comprise an antibody.

The above and other objects may be achieved through the use of kits involving a first oligonucleotide selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, and SEQ ID NO. 18 and an indication of a result that signifies the amount of Influenza A virus resistant to an antiviral composition. If the first oligonucleotide includes SEQ ID NO. 2, then the kit may further comprise a second oligonucleotide such as one that includes SEQ ID NO. 3. The kit may still further comprise a third oligonucleotide such as one that includes SEQ ID NO. 1 and a fourth oligonucleotide such as one that includes SEQ ID NO. 4. If the first oligonucleotide includes SEQ ID NO. 6, then the kit may further comprise a second oligonucleotide such as one that includes SEQ ID NO. 7. The kit may still further comprise a third oligonucleotide such as one that includes SEQ ID NO. 5 and a fourth oligonucleotide such as one that includes SEQ ID NO. 8. If the first oligonucleotide includes SEQ ID NO. 13, then the kit may further comprise a second oligonucleotide such as one that includes SEQ ID NO. 14. The kit may still further comprise a third oligonucleotide such as one that includes SEQ ID NO. 5 and a fourth oligonucleotide such as one that includes SEQ ID NO. 8. If the first oligonucleotide includes SEQ ID NO. 10, then the kit may further comprise a second oligonucleotide such as one that includes SEQ ID NO. 11. The kit may still further comprise a third oligonucleotide such as one that includes SEQ ID NO. 9 and a fourth oligonucleotide such as one that includes SEQ ID NO. 12. If the first oligonucleotide includes SEQ ID NO. 16, then the kit may further comprise a second oligonucleotide such as one that includes SEQ ID NO. 17. The kit may still further comprise a third oligonucleotide such as one that includes SEQ ID NO. 15 and a fourth oligonucleotide such as one that includes SEQ ID NO. 18. The kit may further comprise an enzyme such as a reverse transcriptase or a DNA polymerase such as a thermostable DNA polymerase. The first oligonucleotide may be affixed to a solid substrate. The result may be any result such as a $\Delta Ct_{r-s}$ value. The indication may be any indication such as a positive control. If the indication comprises a positive control, the kit may comprise a first mixture with a known percentage of Influenza A resistant to an antiviral composition and a known percentage of Influenza A sensitive to the antiviral composition. The indication may comprise a writing. The writing may be physically contained within the kit, it may be made available via the Internet, it may comprise an amplification plot, or a ΔCt normalization value.

BRIEF DESCRIPTION OF THE FIGURES

A more complete understanding of the present invention may be derived by referring to the detailed description when considered in connection with the following illustrative figures.

FIG. 1 depicts the variance of the FluMAMA assay between replicates with mixtures comprising about 50% and about 100% L26F mutant at the total DNA concentrations on the X axis.

FIG. 2 depicts the variance of the FluMAMA assay between replicates with mixtures comprising about 5% and about 10% L26F mutant at the total DNA concentrations on the X axis.

FIG. 3 depicts the variance of the FluMAMA assay between replicates with mixtures comprising about 0%, about 0.25%, about 0.5%, and about 1% L26F mutant at the total DNA concentrations on the X axis.

FIG. 4 depicts the variance of the FluMAMA assay between replicates with mixtures comprising about 50% and about 100% V27A mutant at the total DNA concentrations on the X axis.

FIG. 5 depicts the variance of the FluMAMA assay between replicates with mixtures comprising about 5% and about 10% V27A mutant at the total DNA concentrations on the X axis.

FIG. 6 depicts the variance of the FluMAMA assay between replicates with mixtures comprising about 0%, about 0.25%, about 0.5%, and about 1% V27A mutant at the total DNA concentrations on the X axis.

FIG. 7 depicts the variance of the FluMAMA assay between replicates with mixtures comprising about 50% and about 100% A30T mutant at the total DNA concentrations on the X axis.

FIG. 8 depicts the variance of the FluMAMA assay between replicates with mixtures comprising about 5% and about 10% A30T mutant at the total DNA concentrations on the X axis.

FIG. 9 depicts the variance of the FluMAMA assay between replicates with mixtures comprising about 0%, about 0.25%, about 0.5%, and about 1% A30T mutant at the total DNA concentrations on the X axis FIG. 10 depicts the variance of the FluMAMA assay between replicates with mixtures comprising about 50% and about 100% S31N mutant at the total DNA concentrations on the X axis.

FIG. 11 depicts the variance of the FluMAMA assay between replicates with mixtures comprising about 5% and about 10% S31N mutant at the total DNA concentrations on the X axis.

FIG. 12 depicts the variance of the FluMAMA assay between replicates with mixtures comprising about 0%, about 0.25%, about 0.5%, and about 1% S31N mutant at the total DNA concentrations on the X axis FIG. 13 depicts the variance of the FluMAMA assay between replicates with mixtures comprising about 50% and about 100% H274Y mutant at the total DNA concentrations on the X axis.

FIG. 14 depicts the variance of the FluMAMA assay between replicates with mixtures comprising about 5% and about 10% H274Y mutant at the total DNA concentrations on the X axis.

FIG. 15 depicts the variance of the FluMAMA assay between replicates with mixtures comprising about 0%, about 0.25%, about 0.5%, and about 1% H274Y mutant at the total DNA concentrations on the X axis.

Figure 1:
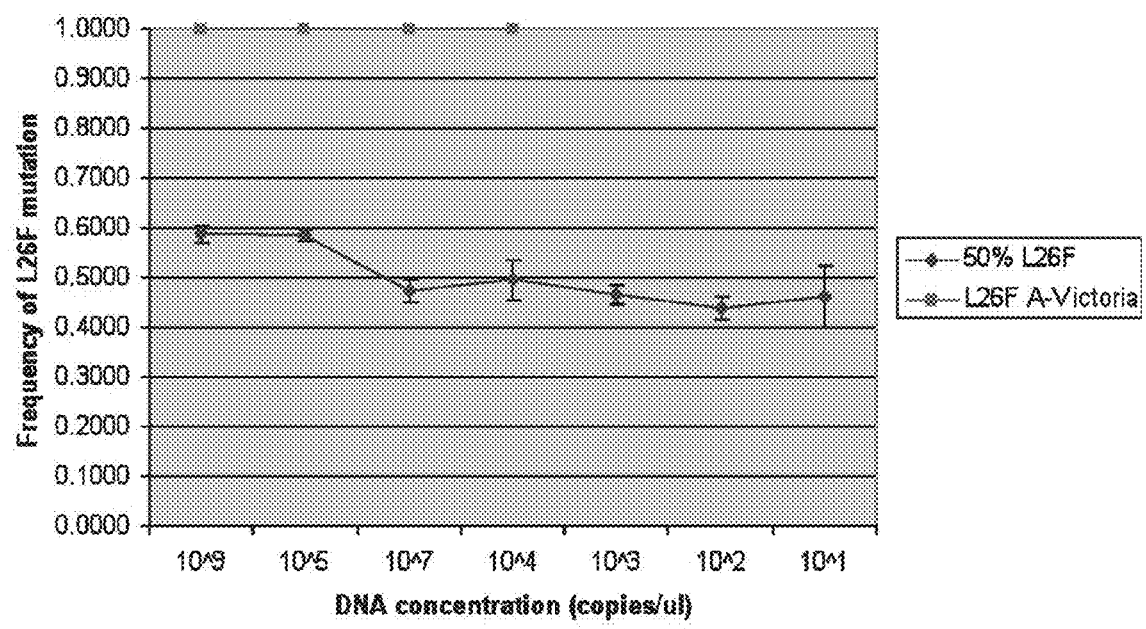
Figure 2:
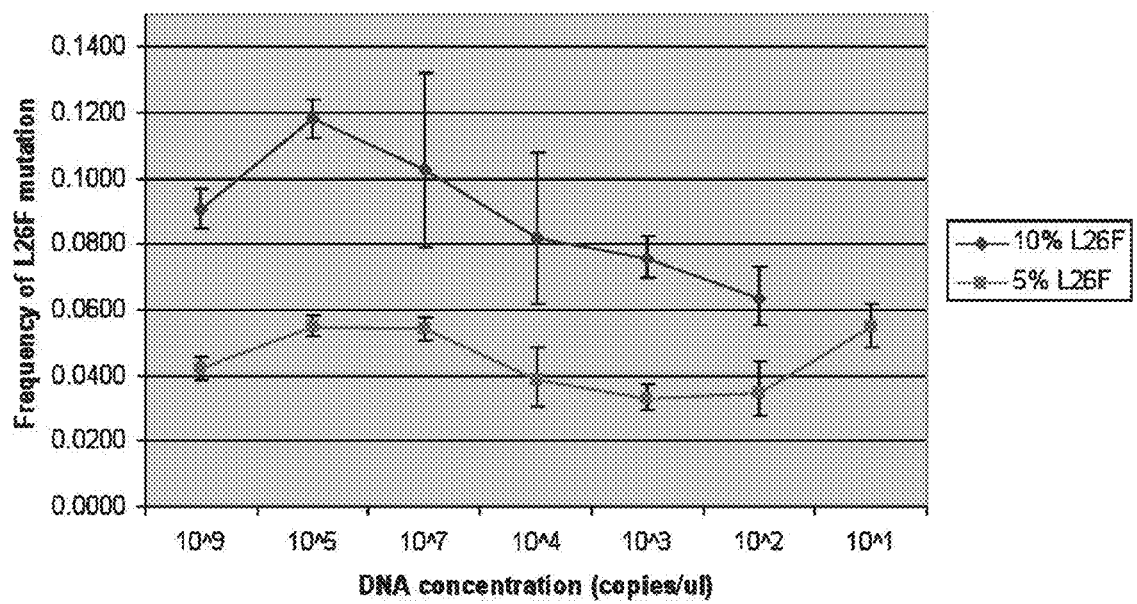
Figure 3:
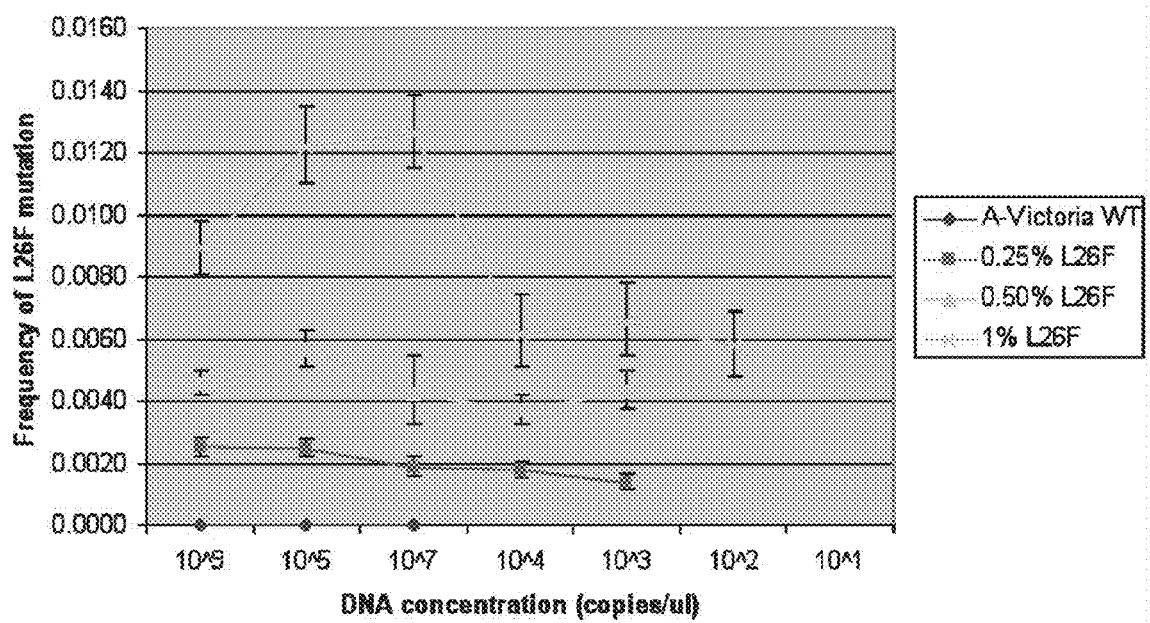
Figure 4:
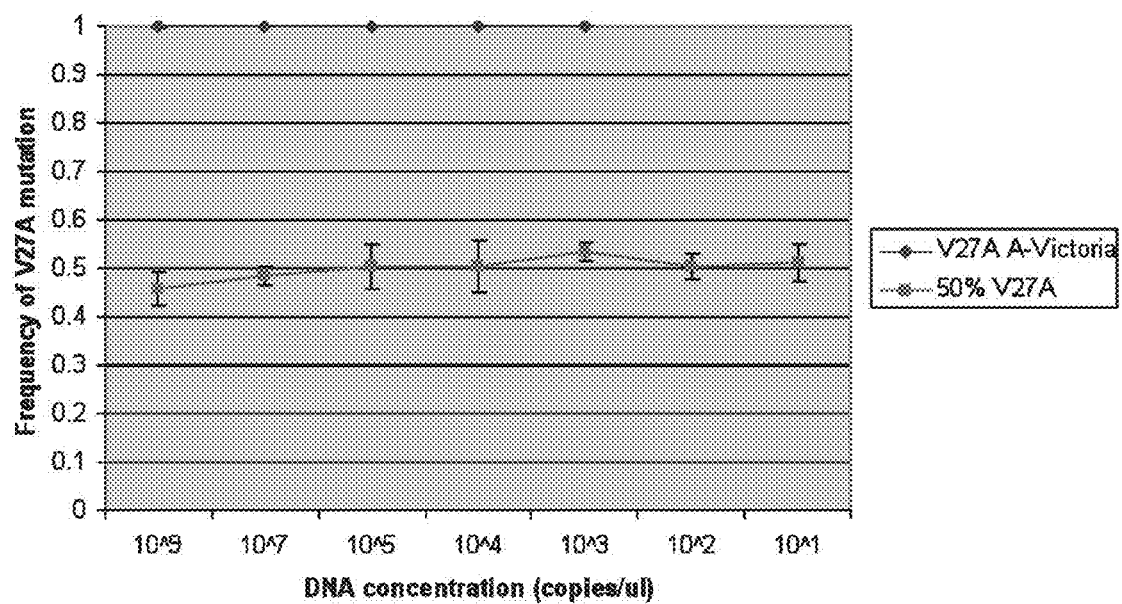
Figure 5:
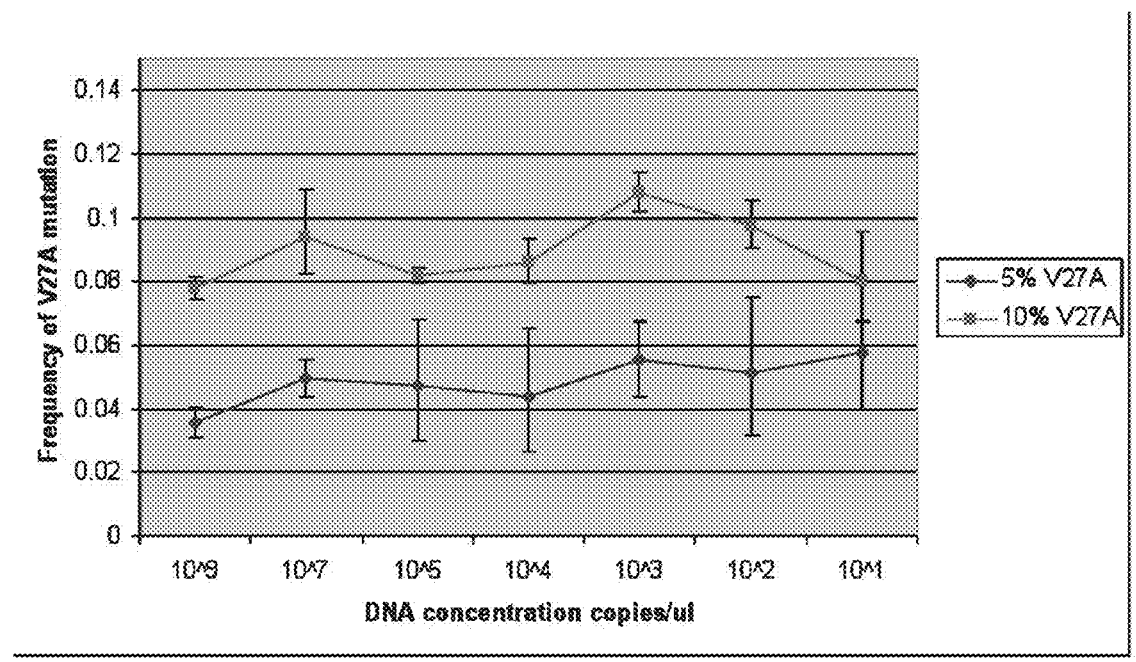
Figure 6:
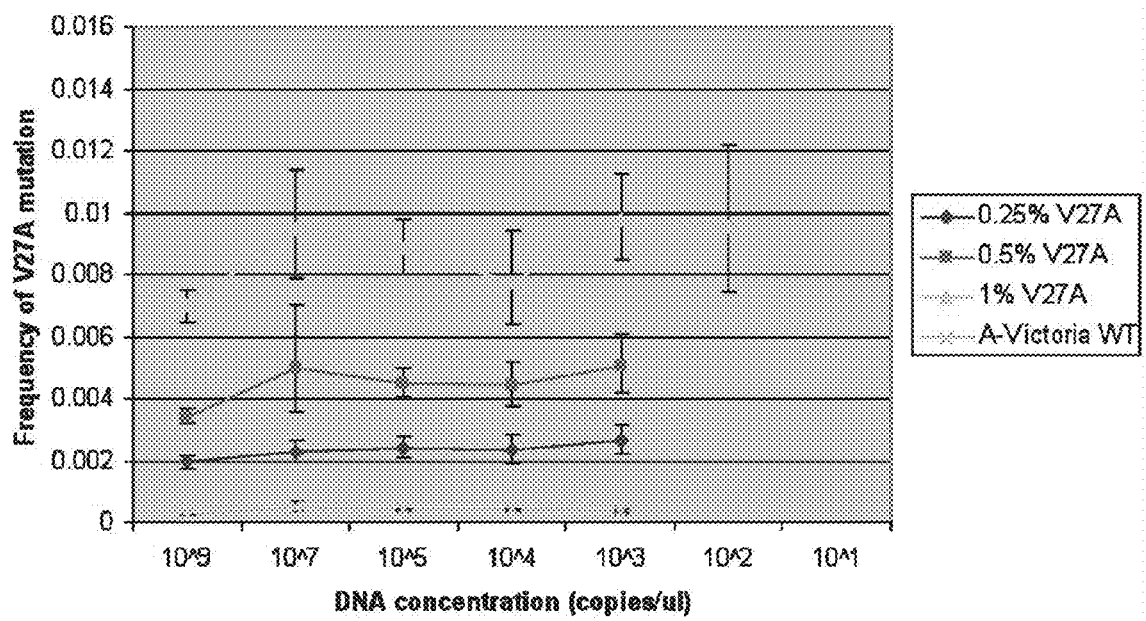
Figure 7:
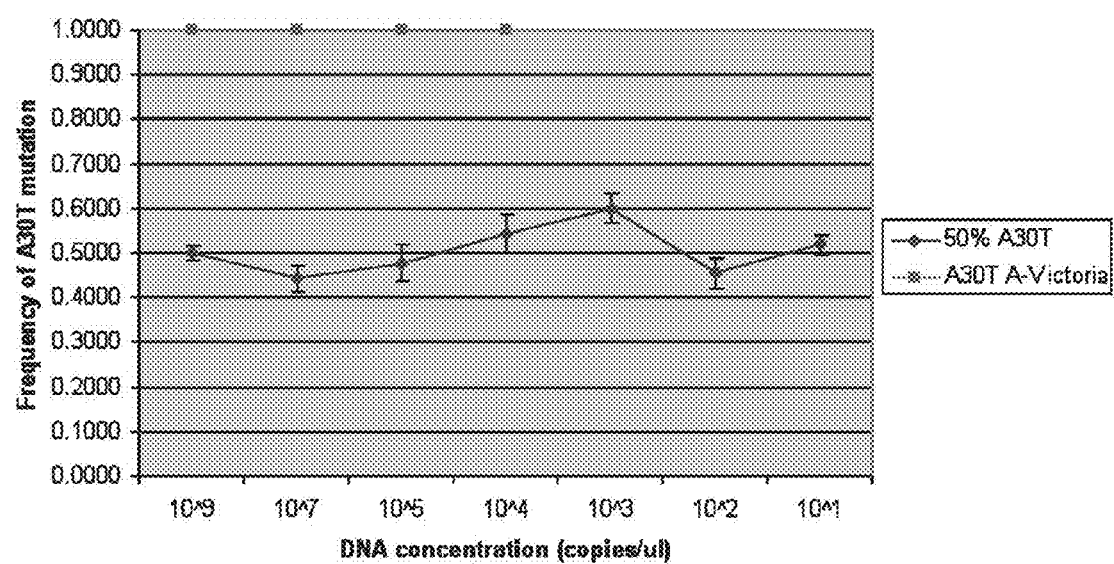
Figure 8:
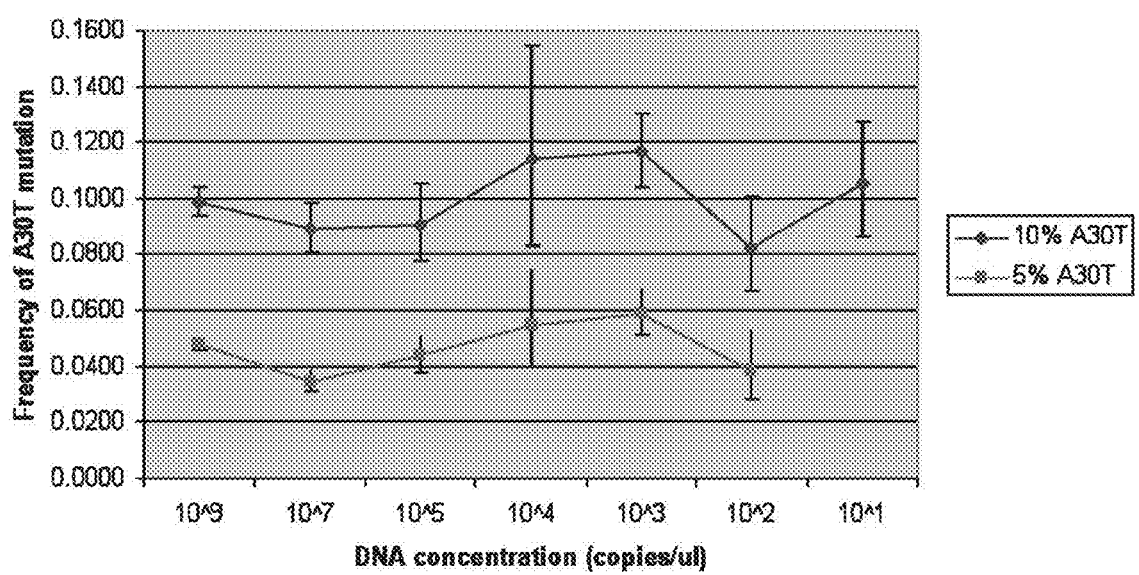
Figure 9:
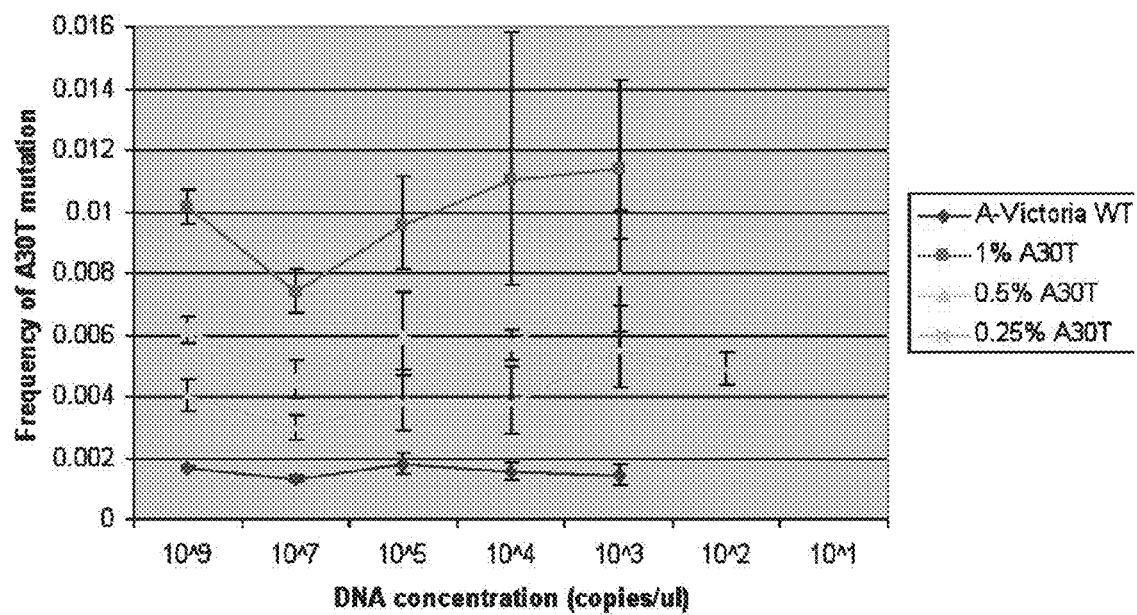
Figure 10:
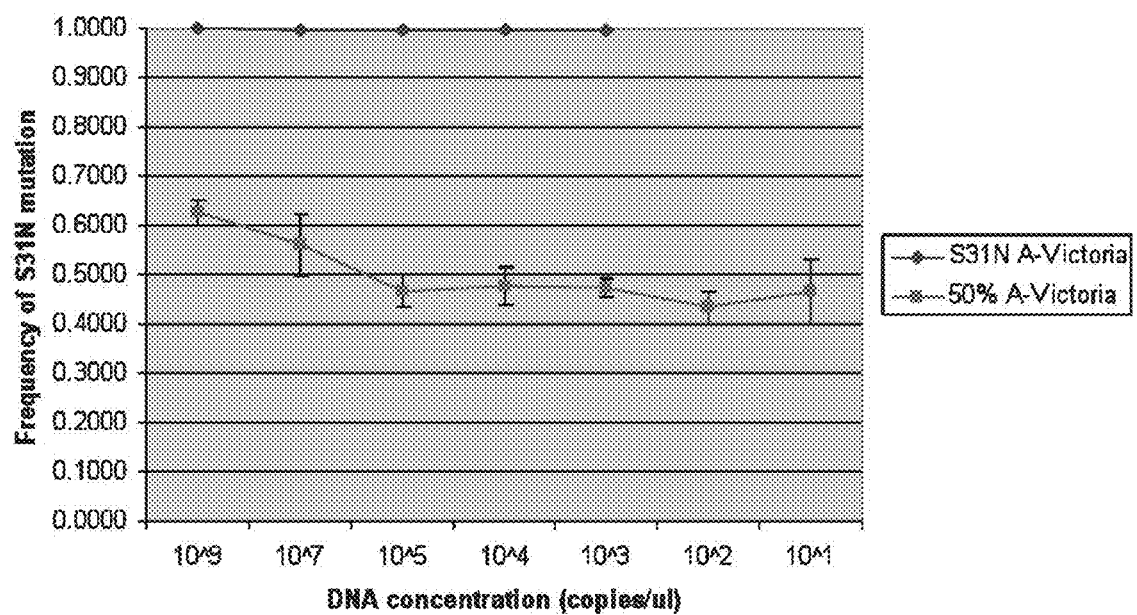
Figure 11:
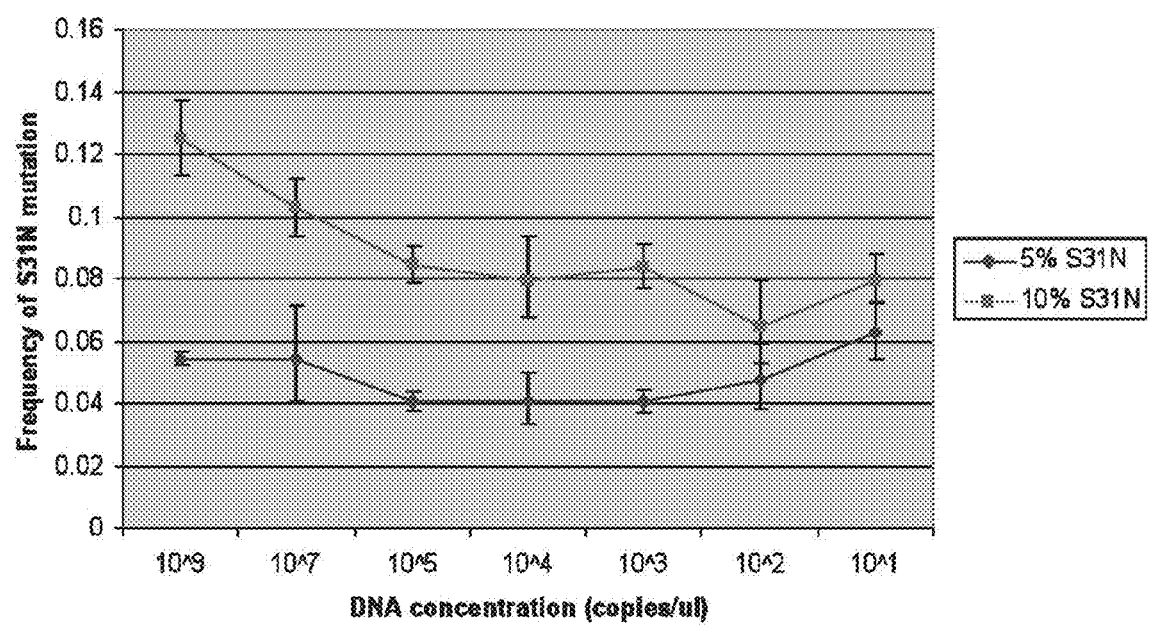
Figure 12:
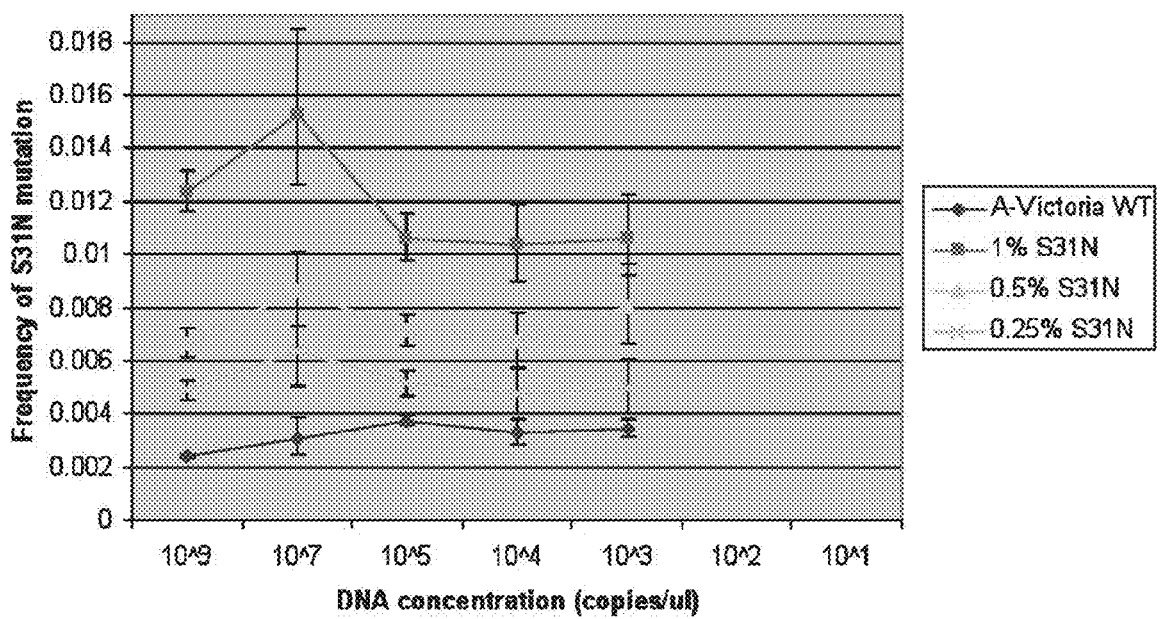
Figure 13:
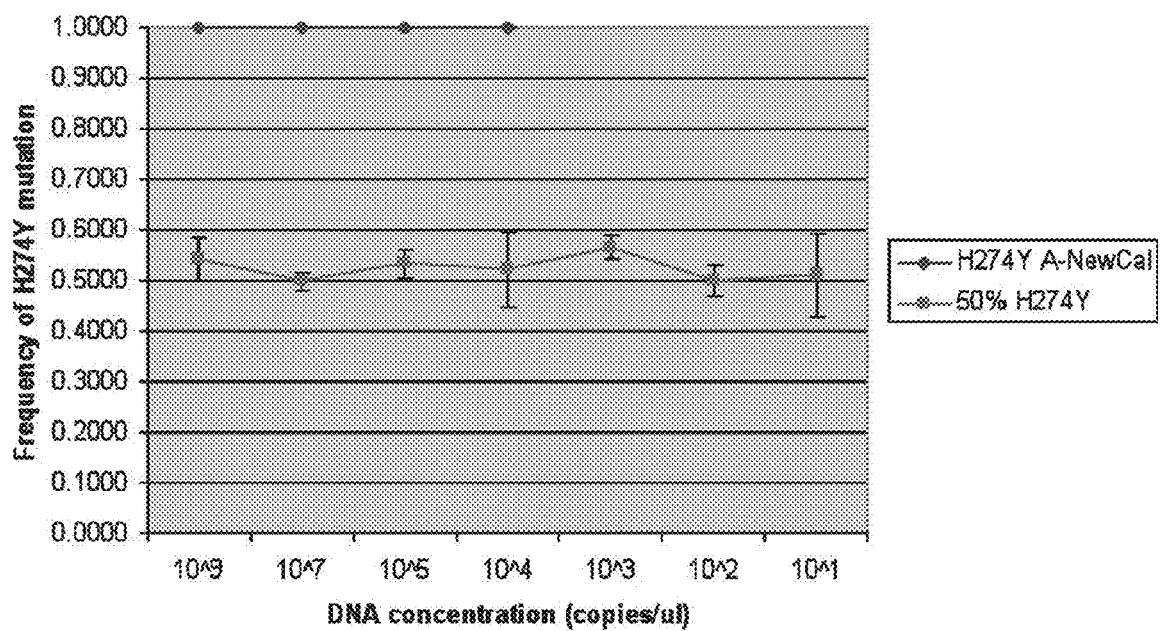
Figure 14:
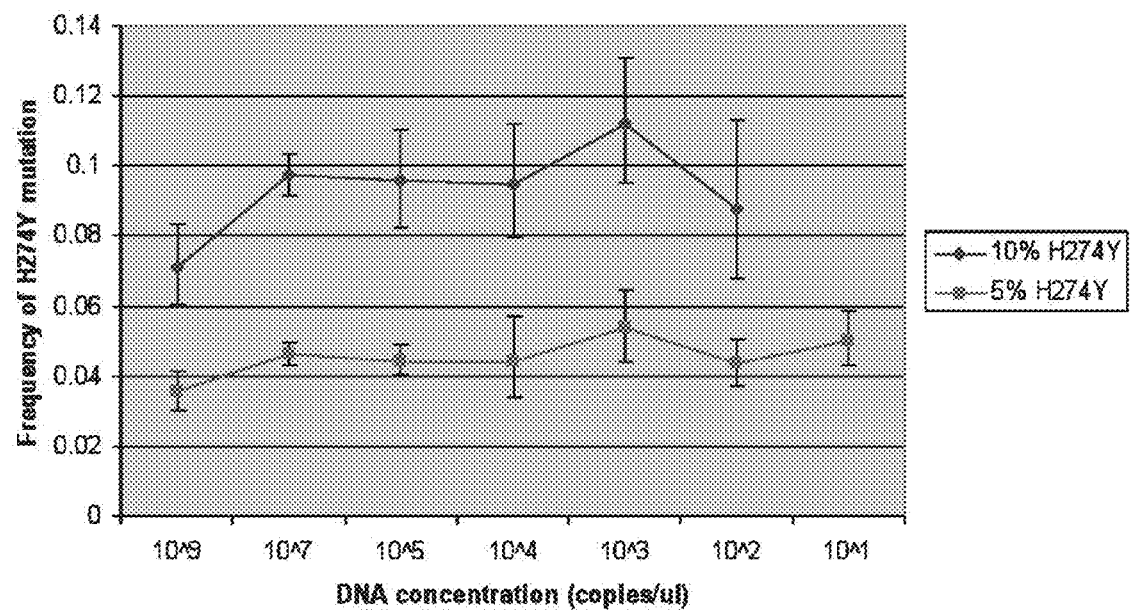
Figure 15:
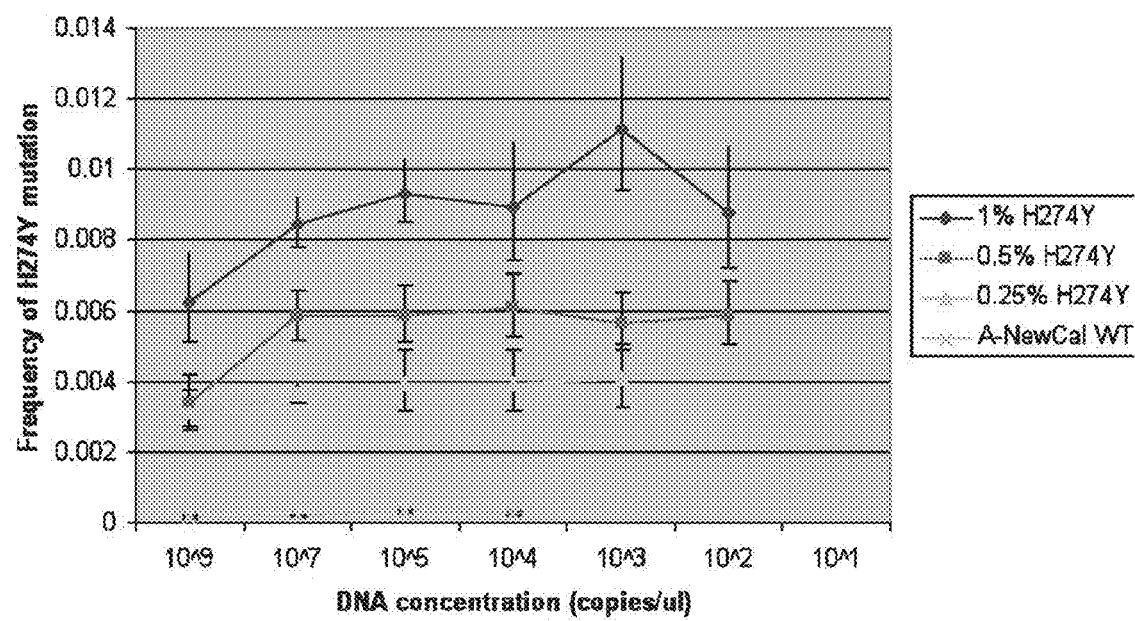

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Inventors are fully aware that they can be their own lexicographers if desired.

Inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that the noun, term, or phrase is given its broadest possible meaning.

Further, the inventors are fully informed of the standards and application of the special provisions of 35 U.S.C. §112, ¶ 6. Thus, the use of the words "function," "means" or "step" in the Detailed Description or Description of the Drawings or claims is not intended to somehow indicate a desire to invoke the special provisions of 35 U.S.C. §112, ¶ 6, to define the invention. To the contrary, if the provisions of 35 U.S.C. §112, ¶ 6 are sought to be invoked to define the inventions, the claims will specifically and expressly state the exact phrases "means for" or "step for, and will also recite the word "function" (i.e., will state "means for" performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶ 6. Moreover, even if the provisions of 35 U.S.C. §112, ¶ 6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Investigators herein disclose nucleotide compositions of matter and methods of using said compositions to detect and/or quantify influenza variants.

A marker may be any molecular structure produced by a cell, expressed inside the cell, accessible on the cell surface, or secreted by the cell. A marker may be any protein, carbohydrate, fat, nucleic acid, catalytic site, or any combination of these such as an enzyme, glycoprotein, cell membrane, virus, cell, organ, organelle, or any uni- or multimolecular structure or any other such structure now known or yet to be disclosed whether alone or in combination. A marker may also be called a target and the terms are used interchangeably.

A marker may be represented by the sequence of a nucleic acid from which it can be derived. Examples of such nucleic acids include miRNA, tRNA, siRNA, mRNA, cDNA, or genomic DNA sequences. While a marker may be represented by the sequence of a single nucleic acid strand (e.g. 5'→3'), nucleic acid reagents that bind the marker may also bind to the complementary strand (e.g. 3'→5'). Alternatively, a marker may be represented by a protein sequence. The concept of a marker is not limited to the products of the exact nucleic acid sequence or protein sequence by which it may be represented. Rather, a marker encompasses all molecules that may be detected by a method of assessing the expression of the marker.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A—Adenine base; C—Cytosine base; G—guanine base; T or U—thymine or uracil base. M-A or C; R-A or G; W-A or T; S—C or G; Y—C or T; K-G or T; V-A or C or G; H-A or C or T; D-A or G or T; B—C or G or T; N or X-A or C or G or T. Note that T or U may be used interchangeably depending on whether the nucleic acid is DNA or RNA. A reagent capable of binding to a nucleic acid sequence having less than 60% 70%, 80%, 90%, 95%, 99% or 100% identity to the identifying sequence may still be encompassed by the invention if it is still capable of binding to its complimentary sequence and/or facilitating nucleic acid amplification of a desired sequence. Although a nucleic acid sequence represented by the sequence of a single nucleic acid strand (e.g. the 5'→3' strand) the totality of reagents that bind to the sequence also includes all reagents capable of binding to the complementary strand (e.g the 3'→5' strand). If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence. Examples of molecules encompassed by a marker represented by a particular sequence or structure include point mutations, silent mutations, deletions, frameshift mutations, translocations, alternative splicing derivatives, differentially methylated sequences, truncations, soluble forms of cell membrane associated markers, and any other variation that results in a product that may be identified as the marker. The following nonlimiting examples are included for the purposes of clarifying this concept: If expression of a specific marker in a sample is assessed by PCR, and if the sample expresses an DNA sequence different from the sequence used to identify the specific marker by one or more nucleotides, but the marker may still be detected using PCR, then the specific marker encompasses the sequence present in the sample. A marker may also be represented by a protein sequence, which includes mutated and differentially modified protein sequences.

The invention may comprise methods detecting the presence of a particular virus in a sample. A sample may be derived from anywhere that a virus or any part of a virus may be found including soil, air, water, solid surfaces (whether natural or artificial,) culture media, foodstuffs, and any interfaces between or combinations of these elements. Additionally, a sample may be derived from a subject, such as a plant or animal, including humans. Samples derived from animals include but are not limited to biopsy or other in vivo or ex vivo analysis of prostate, breast, skin, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF,) cerebrospinal fluid, semen, amniotic fluid, lacrimal fluid, stool, urine, hair, or any other source in which a fungus, or any part of a fungus might be present. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may be suspected of containing a virus if they are derived from a subject displaying symptoms of a viral infection or from an environmental sample from an area in which a virus is thought to be present.

Direct methods of detecting the presence of a marker include but are not limited to any form of DNA sequencing including Sanger, next generation sequencing, pyrosequencing, SOLID sequencing, massively parallel sequencing, pooled, and barcoded DNA sequencing or any other sequencing method now known or yet to be disclosed; PCR-based methods such as real-time PCR, quantitative PCR, or any combination of these; allele specific ligation; comparative genomic hybridization; array based genotyping including SNP genotyping, or any other method that allows the detection of a particular nucleic acid sequence within a sample or enables the differentiation of one nucleic acid from another nucleic acid that differs from the first nucleic acid by one or more nucleotides. A sample may be suspected of including a nucleic acid from a fungus of interest. A subject may be any organism that may be infected by a virus including bacteria, plants, animals, chordates, mammals, humans, insects, endangered species, or any other organism of agricultural, environmental, or other significance.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a phyrophosphate upon nucleotide incorporation. An ATP sulfyrlase enayme converts pyrophosphate into ATP which in turn catalyzes the conversion of luciferin to oxyluciferin which results in the generation of visible light that is then detected by a camera.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence The beads are bound to a glass surface. Sequencing is then performed through 2-base encoding.

In massively parallel sequencing, randomly fragmented DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

Indirect methods of detecting a marker generally involve assessing the expression of material created from a genomic DNA template such as a RNA or protein molecule. Such expression may be assessed by any of a number of methods used currently in the art and yet to be developed. Examples include any nucleic acid detection method including the following nonlimiting examples, microarray RNA analysis, RNA in situ hybridization, RNAse protection assay, Northern blot, reverse transcription PCR, and quantitative reverse transcription PCR. Other examples include any process of detecting expression that uses an antibody including the following nonlimiting examples, flow cytometry, immunohistochemistry, ELISA, Western blot, Northwestern blot, and immunoaffinity chromatography. Antibodies may be monoclonal, polyclonal, or any antibody fragment including an Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

A reagent may be any substance that facilitates any method of detecting a marker. Examples of reagents include nucleic acids such as oligonucleotide probes, nucleic acid mixtures, or full length nucleic acids; proteins such as antibodies, natural ligands, or enzymes; or small molecule compounds in or out of solution such as drugs, buffers, vitamins, or any other artificial or naturally occurring compound that may facilitate the detection of a marker. A reagent may be capable of specific binding to the marker such as a nucleic acid probe or antibody with specificity for the marker.

A reagent may be added to a sample by any of a number of methods including manual methods, mechanical methods, or any combination thereof. The presence of the marker may be signified by any of a number of methods including amplification of a specific nucleic acid sequence, sequencing of a native or amplified nucleic acid, or the detection of a label either bound to or released as a result of the detection of the marker. Addition of a reagent capable of specifically binding a marker to a sample also encompasses addition of the reagent to a sample in which the marker to which the nucleic acid has specificity is absent.

In some aspects of the invention, the presence of a marker may be established by binding to a microarray such as a DNA chip. Examples of DNA chips include chips in which a number of single stranded oligonucleotide probes are affixed to a solid substrate such as silicon glass. Oligonucleotides capable of binding to a marker are capable of hybridizing to all or part of the marker to the exclusion of sequences that differ from those included within the marker by one or more nucleotides. The number of nucleotide differences that may be tolerated are dependant upon the hybridization conditions. Labeled sample DNA is hybridized to the oligonucleotides and detection of the label is correlated with binding of the sample and consequently the presence of the allele in the sample.

In allele-specific hybridization, oligonucleotide sequences representing all possible variations at a polymorphic site are included on a chip. The chip and sample are subject to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read at least four different fluorescent labels on a DNA chip. In another alternative, the identity of the final dNTP added to the oligonucleotide may be assessed by mass spectrometry. In this alternative, the dNTP's may, but need not be labeled with a label of known molecular weight.

A reagent may be affixed to a substrate. In other aspects of the invention, a sample may be affixed to the substrate and made available to a reagent in solution. A reagent or sample may be covalently bound to the substrate or it may be bound by some non covalent interaction including electrostatic, hydrophobic, hydrogen bonding, Van Der Waals, magnetic, or any other interaction by which a reagent capable of specific binding to a marker such as an oligonucleotide probe may be attached to a substrate while maintaining its ability to recognize the marker to which it has specificity. A substrate may be any solid or semi solid material onto which a probe may be affixed, attached or printed, either singly or in the presence of one or more additional probes or samples as is exemplified in a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A reagent may include a label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include but are not limited to: fluorescein, biotin, digoxigenin, alkaline phosphatese, biotin, streptavidin, $^{3}H$, $^{14}C$, $^{32}P$, $^{35}S$, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of such dyes include but are not limited to: FAM, dR110, 5-FAM, 6FAM, dR6G, JOE, HEX, VIC, TET, dTAMRA, TAMRA, NED, dROX, PET, BHQ+, Gold540, and LIZ.

nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of two or more nucleotide bases, whether DNA or RNA, may be termed a nucleic acid.

A nucleic acid reagent may be affixed to a solid substrate. Alternatively, the sample may be affixed to a solid substrate and the oligonucleotide placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which an oligonucleotide may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

Nucleic acid amplification may be performed using nucleic acids from any source. In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA,) amplification with Qβ replicase, whole genome amplification with enzymes such as ϕ29, whole genome PCR, in vitro transcription with Klenow or any other RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that may based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands may be detected or labeled probes that bind to a specific sequence during the annealing phase release their fluorescent tags during the extension phase. Either of these will allow a quantification of the amount of specific DNA present in the initial sample. RNA may be detected by PCR analysis by creating a DNA template from RNA through a reverse transcriptase enzyme. In some aspects of the invention, the marker may be detected by quantitative PCR analysis, which may be performed using a kit containing components that facilitate genotyping analysis. Genotyping analysis may be performed using a probe that is capable of hybridizing to a nucleic acid sequence of interest.

An oligonucleotide is a reagent capable of binding a nucleic acid sequence. An oligonucleotide may be any polynucleotide of at least 2 nucleotides. Oligonucleotides may be less than 10, less than 15, less than 20, less than 30, less than 40, less than 50, less than 75, less than 100, less than 200, less than 500, or more than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

Oligonucleotide synthesis is the chemical synthesis of oligonucleotides with a defined chemical structure and/or nucleic acid sequence by any method now known in the art or yet to be disclosed. Oligonucleotide synthesis may be carried out by the addition of nucleotide residues to the 5'-terminus of a growing chain. Elements of oligonucleotide synthesis include: De-blocking (detritylation): A DMT group is removed with a solution of an acid, such as TCA or Dichloroacetic acid (DCA), in an inert solvent (dichloromethane or toluene) and washed out, resulting in a free 5' hydroxyl group on the first base. Coupling: A nucleoside phosphoramidite (or a mixture of several phosphoramidites) is activated by an acidic azole catalyst, tetrazole, 2-ethylthiotetrazole, 2-bezylthiotetrazole, 4,5-dicyanoimidazole, or a number of similar compounds. This mixture is brought in contact with the starting solid support (first coupling) or oligonucleotide precursor (following couplings) whose 5'-hydroxy group reacts with the activated phosphoramidite moiety of the incoming nucleoside phosphoramidite to form a phosphite triester linkage. The phosphoramidite coupling may be carried out in anhydrous acetonitrile. Unbound reagents and by-products may be removed by washing. Capping: A small percentage of the solid support-bound 5'-OH groups (0.1 to 1%) remain unreacted and should be permanently blocked from further chain elongation to prevent the formation of oligonucleotides with an internal base deletion commonly referred to as (n−1) shortmers. This is done by acetylation of the unreacted 5'-hydroxy groups using a mixture of acetic anhydride and 1-methylimidazole as a catalyst. Excess reagents are removed by washing. Oxidation: The newly formed tricoordinated phosphite triester linkage is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. This step can be substituted with a sulfurization step to obtain oligonucleotide phosphorothioates. In the latter case, the sulfurization step is carried out prior to capping. Upon the completion of the chain assembly, the product may be released from the solid phase to solution, deprotected, and collected. Products may be isolated by HPLC to obtain the desired oligonucleotides in high purity.

Kits that facilitate methods of detecting a marker may include one or more of the following reagents: specific nucleic acids such as oligonucleotides, labeling reagents, enzymes including PCR amplification reagents such as the thermostable DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A kit may also contain an indication of a result of the use of the kit that signifies a particular characteristic. An indication includes any guide to a result that would signal the presence or absence of any characteristic that the kit is configured to predict. For example, the indication may be expressed numerically, expressed as a color or density of a color, expressed as an intensity of a band, derived from a standard curve, or expressed in comparison to a control. The indication may be communicated through the use of a writing. A writing may be any communication of the result in a tangible medium of expression. The writing may be contained physically in or on the kit (on a piece of paper for example), posted on the Internet, mailed to the user separately from the kit, or embedded in a software package. The writing may be in any medium that communicates how the result may be used to predict the cellular or physiological characteristic that the kit is intended to predict, such as a printed document, a photograph, sound, color, or any combination thereof.

The influenza virus is a member of the family orthomyxoviridae viruses, including Influenzavirus A, Influenzavirus B, and Influenzavirus C. There are multiple serotypes of Influenza A typed according to their hemagglutinin and neuraminidase type including H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7. Further genotypic and phenotypic variances in the Influenza virus may interchangeably be called strains, subtypes, or variants.

An antiviral drug may be any composition of matter that adversely affects viral replication, infectivity, ability to evade the immune system or any other feature of a virus that promotes its ability to replicate or infect a cell. Antiviral drugs used in the treatment of influenza include adamantanes such as amantadine and rimantadine as well as neuraminidase inhibitors such as zanamivir and oseltamivir.

EXAMPLE 1

Elements and acts in the example are intended to illustrate the invention for the sake of simplicity and have not necessarily been rendered according to any particular sequence or embodiment. The example is also intended to establish possession of the invention by the Inventors.

A number of mismatch amplification mutation assays (MAMA) were developed in order to characterize the frequency of SNP minor components in a mixed influenza A sample with unexpected sensitivity and specificity. Such assays may be referred to interchangeably as allele specific mismatch assays (ASMA.)

Five SNP mutations were targeted, each of which confers resistance to antiviral drugs on the influenza virus. These mutations include L26F, V27A, A30T, and S31N in the Influenza A M2 gene and H274Y in the Influenza A NA gene. Viruses lacking these mutations may be considered sensitive to antiviral drugs.

Assays were designed and screened to determine if they were able to quantitate at least a 0.01 resistant:sensitive mixture (FluMAMA). MAMA primers were designed with 3' penultimate or antepenultimate mismatch incorporated into the primer flanking the locus of interest. Known mixtures of plasmid standards were used in FluMAMA validation.

A panel of mixtures of consisting of resistant:sensitive ratios ranging from 0.50:1 to 0.0025:1 were generated at a total concentration of $10^9$ copies/µl using normalized plasmid standards. The FluMAMA assays were then tested against the full panel of resistant:sensitive mixtures in 7 dilutions encompassing 9 logs.

All five FluMAMA assays are capable of detecting the difference between pure sensitive and 0.025 resistant:sensitive at the 95% significance level. FluMAMA validation produced the following results for each mutation: L26F has a validated quantitative threshold at 0.0025 resistant: sensitive at $10^3$ copies/µl and a theoretical quantitative threshold at $3.8*10^6$ resistant:sensitive at $10^7$ copies/µl. V27A has a validated quantitative threshold at 0.0025 resistant:sensitive at $10^3$ copies/µl and a theoretical quantitative threshold of 0.0001 resistant:sensitive at $2*10^3$ copies/µl. A30T has a validated quantitative threshold at 0.025 resistant:sensitive at $10^3$ copies/µl and a theoretical quantitative threshold of 0.0025 resistant:sensitive at $10^3$ copies/µl. S31N has a validated quantitative threshold at 0.05 resistant:sensitive at $10^3$ copies/µl and a theoretical quantitative threshold of 0.05 resistant: sensitive at $10^3$ copies/µl. H274Y has a validated quantitative threshold at 0.025 resistant:sensitive at $10^3$ copies/µl and a theoretical quantitative threshold at $4.88*10^{-4}$ resistant:sensitive at $5*10^3$ copies/µl. While assays detecting M2 alleles (L26F, V27A, A30T, S31N) were validated using the A/Victoria/3/75 influenza strain and assays detecting the NA mutation (H274Y) was validated using the A/New Calcdonia/20/1999 strain, each assay can also be applied to additional strains/subtypes based on sequencing types.

FluMAMA Primer and Probe Design

Influenza A M2 and NA (N1) sequences were obtained from a database of all previously sequenced influenza strains and the influenza nucleotide database in GenBank, then aligned using SeqMan software (Lasergene Software, DNAStar). Codons 26, 27, 30, 31 in M2 and codon 274 in NA were then identified and marked on the aligned sequences.

The most common single nucleotide mutations resulting in L26F, V27A, A30T, S31N, and H274Y mutations, respectively, were used as the mutant SNP target in the final assay. All FluMAMA assays were originally designed with a 3' penultimate (i.e. second from last) mismatch incorporated into the primer flanking the SNP of interest. A perfect match for either the wild-type or the mutant allele at the locus of interest was then incorporated at the 3' end to generate a non-mutant primer and a mutant primer for the antiviral-sensitive assay and the antiviral-resistant assay, respectively. Both sensitive and resistant assays share one primer and a TaqMan MGB probe.

The shared primer was designed to allow ≤five degeneracies and to produce an amplicon size of ≤200 bp. The TaqMan MGB probe was not allowed to contain any degeneracies and was designed using Primer Express® (Applied Biosystems). The Tm and possible dimer and hairpin formations of the designed primers and probes were checked against qPCR design criteria using OligoCalc (Northwestern University) and Primer Express® (Applied Biosystems). If the 3' penultimate mismatch primers failed to produce an assay capable of discriminating at least a 0.01 resistant:sensitive mixture from a pure sensitive mixture, then new primers were designed with a 3' antepenultimate (i.e. third from last) mismatch.

Plasmid Construction Using cDNA or Synthetic Plasmids

Candidate cDNA that could be used to construct plasmids was available for L26F, V27A and S31N mutations. Such plasmids could be used to generate standards. An initial PCR was performed, and the amplified gene targets were then inserted into plasmids, clonally propagated in *E. coli*, then sequence verified.

Primers used to amplify the M2 gene were forward 5' CYA GCA CTA CAG CTA AGG CTA TGG AGC A 3' and reverse 5' CAT CCA CAG CAY TCT GCT GTT CCT 3' and for NA forward 5' CAA AGG AGA TGT TTT TGT CAT AAG AGA ACC 3' and reverse 5' CTC CAT CAA CAG TCA CTG GAT TAC AGC 3'.

PCR was performed using a concentration of 200 nM primers, 300 μM dNTPs, 3 mM MgCl, 1 U/rxn Taq Polymerase, and 1× Taq DNA Polymerase PCR buffer (Invitrogen). A TOPO TA Cloning Kit (Invitrogen) was used to insert the PCR products into the plasmid and to clonally propagate the plasmid. All methods were performed according to the kit instructions (hereby incorporated by reference in their entirety).

PCR products were ligated into the kit's pCR2.1 plasmid vectors in separate reactions. The plasmid vectors were then used to transform *E. coli* cells by heat shock. *E. coli* cells were then plated onto LB X-Gal plates and incubated overnight. White or light blue (as opposed to dark blue) colonies were picked and grown in selective LB broth for approximately 24 hrs. Plasmid was isolated from cultures using QIAprep Spin Miniprep kit (Qiagen), the kit instructions of which are hereby incorporated by reference in their entirety.

A plasmid containing an M2 gene with an A30T mutation and a plasmid containing an NA gene with an H274Y mutation were ordered from Blue Heron Biotechnology GeneMaker®. Both of these plasmids were based on pUC119 vectors. A sequence of the plasmid insert containing the synthetic A30T gene insert was generated using SeqMan (Lasergene software) by aligning common laboratory Influenza A strains and incorporating the most likely SNP (i.e, a single base mutation) to generate the A30T mutation. A sequence of the H274Y gene insert was generated using SeqMan (Lasergene software) by aligning all available H274Y and select recent influenza A H1N1 sequences from GenBank. Both inserts included about 100 bp of sequence both upstream and downstream of the gene sequence. Clonal propagation of the plasmid and plasmid isolation were performed in an identical fashion as the plasmid standards generated from cDNA.

Sequence Verification of Plasmid Standards Generated from cDNA

A PCR was performed in order to verify plasmid sequences. Primers used were the M13 forward 5' CAG GAA ACA GCT ATG AC 3' and M13 Reverse 5' CAG GAA ACA GCT ATG AC 3' on plasmid standards generated from cDNA. The PCR products were sequenced using dye-labeled dideoxy-terminator cycle sequencing using a Big Dye Terminator v3.1 Cycle Sequencing Kit (Applied Biosystems), the instructions for which are hereby incorporated by reference in their entirety. Unincorporated dye-terminators were removed using a DyeEx kit (Qiagen), the instructions for which are hereby incorporated by reference in their entirety. The purified product was then sequenced using capillary electrophoresis on the 3130×1 Genetic Analyzer (Applied Biosystems), manual and instructions for which are hereby incorporated by reference in their entireties. The resulting sequences were aligned with a reference sequence using SeqMan (Lasergene software) to confirm the presence of the targeted alleles.

Plasmid Standard Quantification and Normalization

To normalize all FluMAMA plasmid standards to $10^9$ copies/μl, a qPCR assay, designated Plasquant was designed and validated and used to generate a $10^9$ copies/μl plasmid stock. Plasquant was designed to target a unique region in the β-lactamase gene, a single-copy gene present in most commercially available plasmid vectors. The plasmid standard was generated by diluting a plasmid stock to near single-copy level and testing a large number of replicates (n=64) using a separate validated qPCR to achieve a theoretical failure rate of 30%. The 30% failure rate was calculated using the Poisson distribution. A single-copy dilution factor was then used to back-calculate the copy number in the standard stock ($10^9$ copies/0.

Using Plasquant, which has a dynamic range encompassing 7 orders of magnitude, ($10^9$-$10^2$ copies of plasmid), the $10^9$ copies/μl standard stock was evaluated to obtain a Cp value unique to the concentration (Cp=10). All plasmid preps were then tested using Plasquant to obtain the Cp values and then normalized to Cp=10 to bring all FluMAMA plasmid standards to $10^9$ copies/μ1.

Known Mixture Generation

Resistant:sensitive mixtures at ratios of (0.50, 0.10, 0.05, 0.01, 0.005, 0.0025) at $10^9$ copies/μl were generated using influenza A wild-type strain A/Victoria/3/75 plasmids for the M2 mutations (L26F, V27A, A30T, S31N) and influenza A wild-type strain A/New Calcdonia/20/99 plasmids for H274Y. Mixtures were generating using the calculations in Table 2.

FluMAMA qPCR Procedure

FluMAMA Real Time Quantitative PCR (qPCR) was performed in 10 μl reaction volumes in PRISM™ 384-well Clear Optical Reaction Plates (Applied Biosystems). In each 10 μl reaction, 1 μl of template was added to 9 μl of qPCR reaction mix containing 900 nM of each Forward and Reverse primer (listed in Table 1), 225 nM of the appropriate TaqMan MGB probe (listed in Table 1), 1× TaqMan Universal PCR Master Mix (Applied Biosystems), and molecular-grade water. Separate reactions were carried out with either the sensitive or the resistant allele-specific primer. All reactions were performed in triplicate. Amplification and real-time fluorescence detections were performed on the 7900HT Real Time PCR System (Applied Biosystems) using and the following PCR incubations: 3 min at 50° C.; 10 min at 95° C.; and 40 cycles of the following: 15 s at 95° C., and 1 min at 60°. A manual Ct threshold was set at 0.2 and the baseline was automatically selected. A Ct value was obtained for each reaction using the Sequence Detection System v2.3 software (Applied Biosystems).

FluMAMA Primer Screening

Resistant and sensitive plasmid standards were initially tested across three 1:10 dilutions, and the 50:50 resistant:sensitive mixture was tested across two 1:10 dilutions using both the resistant and sensitive assays.

FluMAMA Assay Validation

Eight resistant:sensitve ratios (100.0, 0.50, 0.10, 0.05, 0.01, 0.005, 0.0025, 0.0) were tested across seven plasmid concentrations ($10^9$, $10^7$, $10^5$, $10^4$, $10^3$, $10^2$, $10^1$ copies/μl). Each targeted mutation (L26F, V27A, A30T, S31N, H274Y) was assessed in three separate runs with identical DNA concentrations and mixtures to assess both intra-run and inter-run variation and to estimate the variances between replicates. Four negative controls were included in each qPCR plate.

Data Analysis

Any Ct data point with a ≥1 Ct difference from the other two data points was excluded as an outlier.

Using the Ct outputs from the FluMAMA wild-type and mutant assays, a mean-difference statistic ($\Delta Ct_{r-s}$) was first calculated using:

$$\Delta Ct_{r-s} = \text{Mean } Ct_{resistant} - \text{Mean } Ct_{sensitive}$$

ΔCt Normalization was performed on the calculated $\Delta Ct_{r-s}$ according to the following: the mean $\Delta Ct_{r-s}$ from the 0.50 resistant-sensitive ratio was calculated and subtracted from the $\Delta Ct_{r-s}$ values from other resistant:sensitive mixtures. Then the resistant:sensitive ratio was calculated using the following formula: resistant:sensitive ratio=$1/(2^{\Delta Ct_{r-s}}+1)$ Alternatively, a percentage of an antiviral resistant mutant may be expressed as:

$$\% \text{ mutant} = 1/(2^{\Delta Ct_{mut-wt}}+1) \times 100$$

To obtain the 95% confidence interval of the calculated resistant:sensitive ratio, the pooled variance of the two Ct means was first calculated using:

$$\text{Pooled variance of Mean } Ct_{resistant} \text{ and Mean } Ct_{sensitive} = \frac{(N_{resistant}-1)SD^2_{resistant} + (N_{sensitive}-1)SD_{sensitive}}{N_{resistant}+N_{sensitive}-2}$$

where N=# of replicates for the FluMAMA mutant or wild-type assay, SD=standard deviation of the mean Ct indicated.

The square root of the pooled variance was then taken to obtain the pooled standard deviation between the two groups of means. The pooled standard deviation was then used to calculate the standard error (SE) of the mean difference statistic (i.e. of $\Delta Ct_{r-s}$) using the formula:

$$SE \text{ of } \Delta Ct_{r-s} = \text{Pooled } SD * (1/N_{resistant}+1/N_{sensitive})^{1/2}$$

The SE of $\Delta Ct_{r-s}$ was then used to calculate the upper and the lower limits of the 95% confidence interval for $\Delta Ct_{r-s}$, which was then used to calculate the upper and lower limits of the calculated resistant:sensitive ratio using:

(resistant:sensitive ratio lower limit, resistant:sensitive ratio upper limit)=$((1/(2^{\Delta Ct_{r-s} \text{ lower limit}}+1), 1/(2^{\Delta Ct_{r-s} \text{ upper limit}}+1))$ To calculate the 95% confidence interval for % mutant estimation, the pooled variance of the two Ct means was first calculated, then the pooled standard deviation between the two means was obtained, which was used to calculate the standard error (SE) of the mean difference statistic (i.e. of $\Delta Ct_{mut-wt}$). The SE of $\Delta Ct_{mut-wt}$ was then used to calculate the upper and the lower limits of the 95% confidence interval for $\Delta Ct_{mut-wt}$, which was then used to calculate the upper and lower limits of the calculated mutant:WT ratio using:

(% mutant lower limit, % mutant ratio upper limit)=
$((1/(2^{\Delta Ct_{mut-wt} \text{ lower limit}}+1) \times 100, 1/(2^{\Delta Ct_{mut-wt} \text{ upper limit}}+1) \times 100)$ Theoretical lower limit of quantification was calculated using $\Delta Ct_{mut-wt}$ calculated using data from 100% wild-type plasmid standard template in the following equation $$\% \text{ mutant quantification threshold} = 1/(2^{\Delta Ct_{mut-wt}-1}+1) \times 100$$

And the minimum total gene target concentration required for the calculated % mutant lower limit of quantification can be calculated using:

Minimum total gene target concentration=25/(calculated % mutant quantification threshold)

Data Analysis for Primer Screening

FluMAMA assay results were then subjected to the following criteria: $\Delta C_{r-s} \geq 8$ against pure A/Victoria or A/New Calcdonia wild-type plasmid, as applicable and $\Delta Ct_{r-s} \leq 1$ against a 50:50 resistant:sensitive mixture. Assays meeting the criteria were selected for validation.

Figure 18:
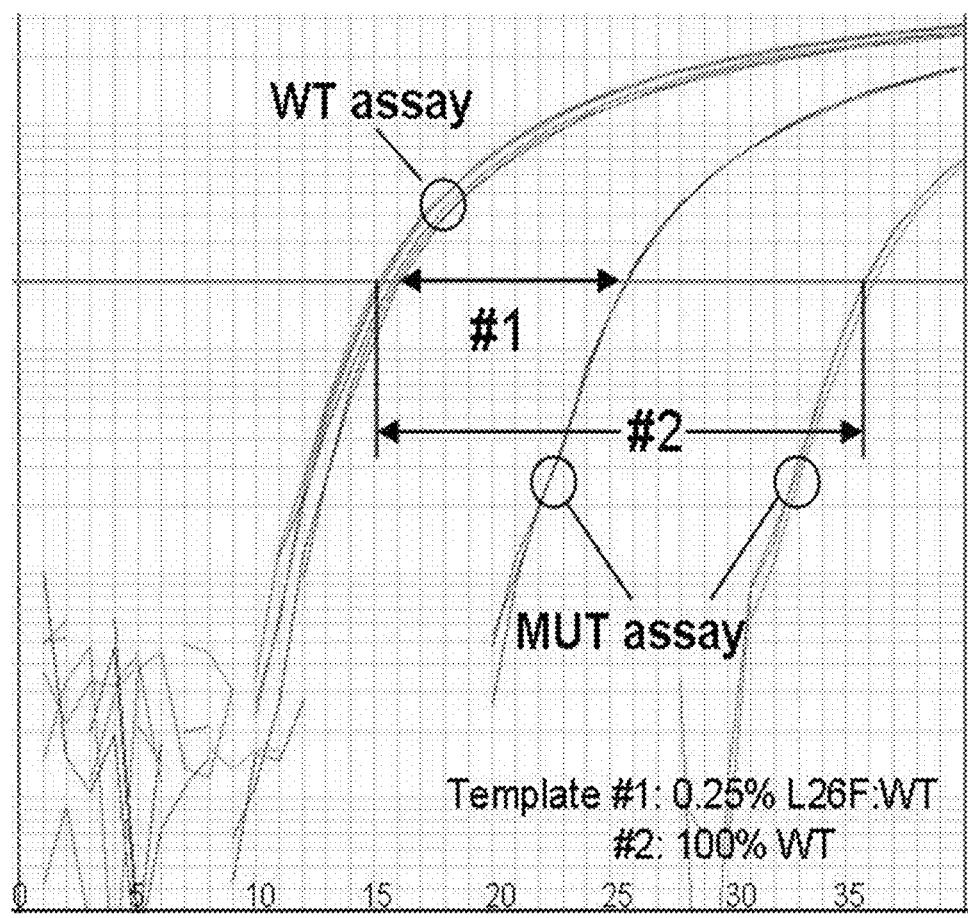
FIG. 18 depicts a plot used to determine an analysis threshold and a minor mutant component using $\Delta Ct$ from allele-specific arrays.
Figure 19:
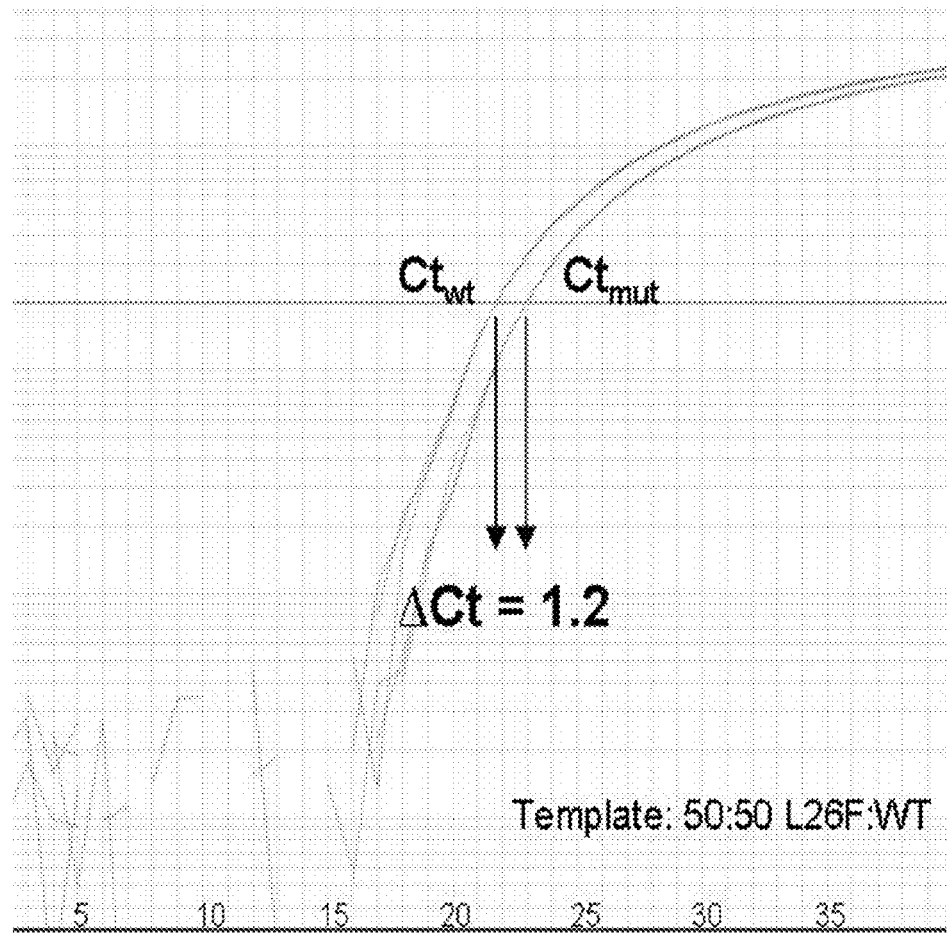
FIG. 19 depicts an example of a plot used to determine a $\Delta Ct$ value for normalization.

Simultaneous application of the sensitive and resistant FluMAMA assays to the same sample generate Ct values that can be used to estimate the mutant to wild-type ratio in mixtures (FIG. 18) and to determine assay-specific normalization values (FIG. 19) and quantitative analysis thresholds (FIG. 18). Using the coupled allele-specific PCR assays, the $\Delta Ct_{r-s}$ and its associated standard error may be obtained in each and estimate the % mutant in each tested mixture with a 95% confidence interval. This allows FluASMA to perform sensitive quantitative SNP analysis using samples that contain multiple alleles. In FIG. 19, the ΔCt normalization value may be determined using data from a 50:50 L26F:WT mixture. At $10^5$ template copies, a mixture of 50% L26F mutant in otherwise unmutated plasmid resulted in an L26F assay value of $Ct_{resistant}=22.95$ (μ, n=3) and a sensitive allele assay value of $Ct_{sensitive}=21.75$ (μ, n=3) to generate a ΔCt=1.2. This ΔCt value, combined with ΔCt values calculated across the entire dynamic range is used to generate a range-wide combined average ΔCt=1.1, which is used to normalize subsequent experimental data for the L26F FluMAMA.

Figure 20:
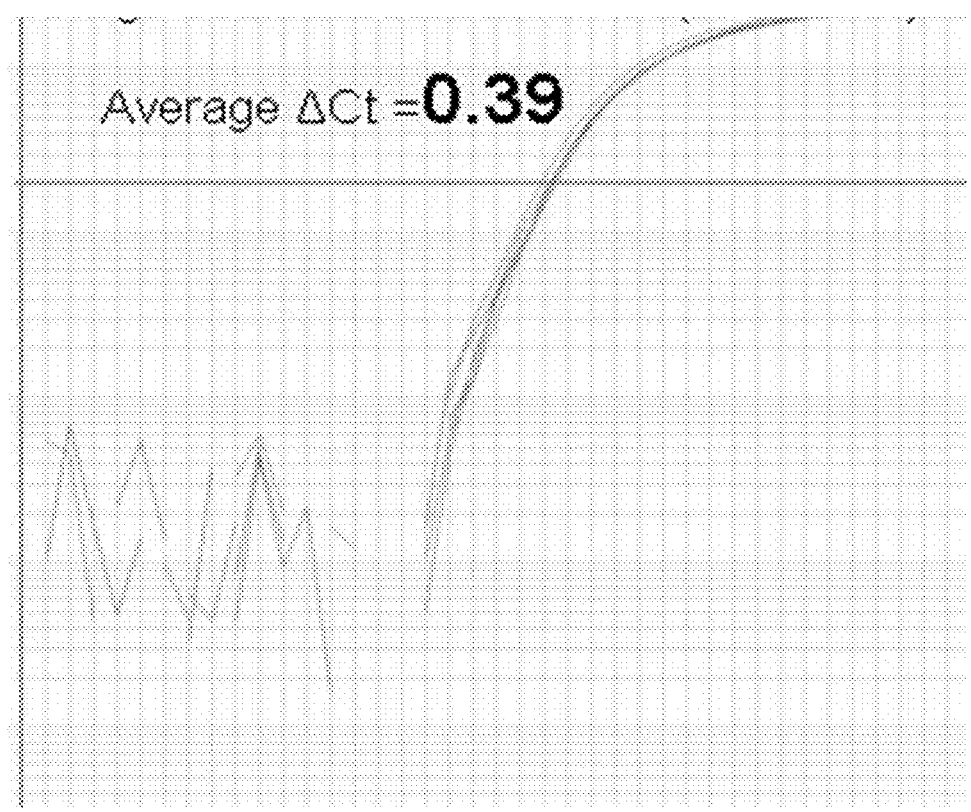
FIG. 20 depicts a plot used to determine the $\Delta Ct$ normalization value of a 50% V27A mixture.

In FIG. 20, a FluMAMA quantitative analysis threshold and mutant to wild-type ratio using $\Delta Ct_{r-s}$ data from allele-specific assays is depicted as an example. A 0.25% L26F mixture at $10^6$ template copies was used as a template. The allele-specific assays produced $Ct_{sensitive}$ (SD)=22.70 (0.03) and $Ct_{resistant}$(SD)=32.19 (0.09). Using these experimental data, we can calculate the percent L26F mutant (95% CI) to be 0.30 (0.28, 0.32), The theoretical quantification threshold of L26F FluMAMA using $\Delta Ct_{r-s}$ data from allele-specific assays against 100% WT standards. The theoretical quantification threshold was determined to be at $1/(2^{18}+1) * 100 = 0.000381\%$.

We further illustrated the application of FluASMA using V27A FluASMA against various known mixtures at a DNA concentration of $10^5$ copies/μl (FIGS. 20-25). Using the average $\Delta Ct_{r-s}$ calculated from 50% V27A mixtures, a normalization value unique to V27A FluMAMA was calculated (FIG. 20). Then, we generated the normalized $\Delta Ct_{r-s}$ values and calculated the % mutant and its associated 95% confidence interval for each tested mixture (FIGS. 21-25). The one Ct difference we observed between the normalized $\Delta Ct_{r-s}$ values of 0.25% V27A and 0.50% V27A, 0.50% V27A and 1% V27A, and 5% V27A and 10% V27A further illustrate the sensitivity of the FluASMA in quantifying SNP minor components in mixtures.

Figure 21:
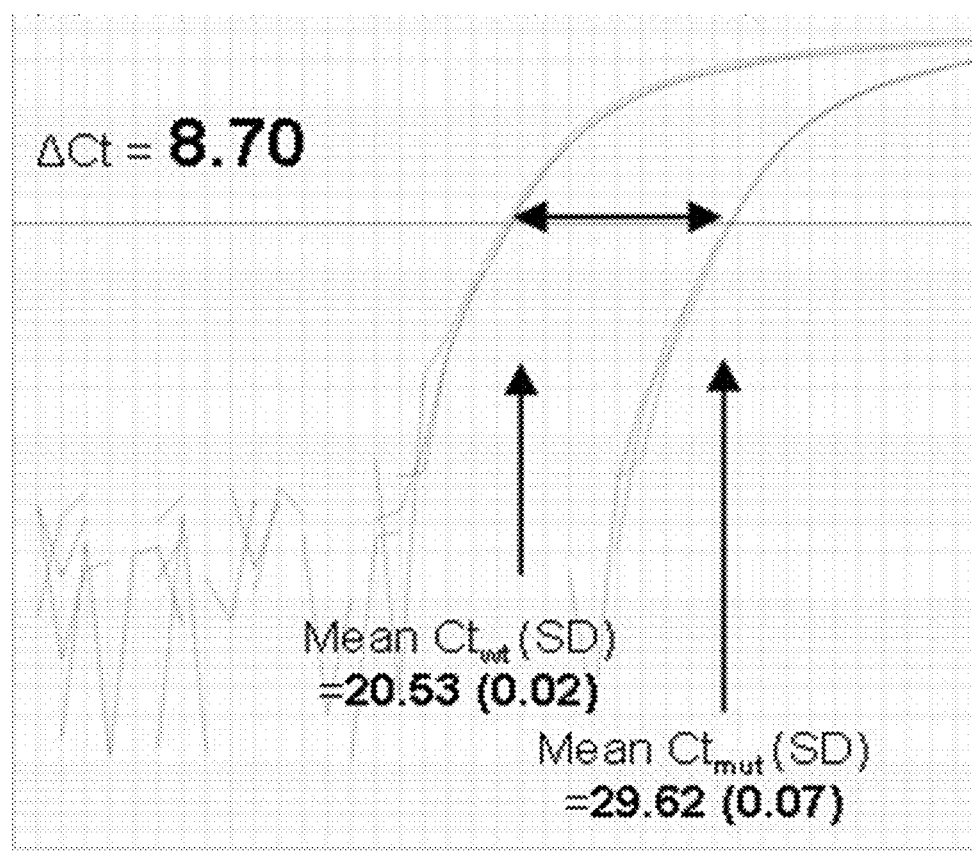
FIG. 21 depicts a plot used to determine the $\Delta Ct$ normalization value of a 0.25% V27A mixture.
Figure 22:
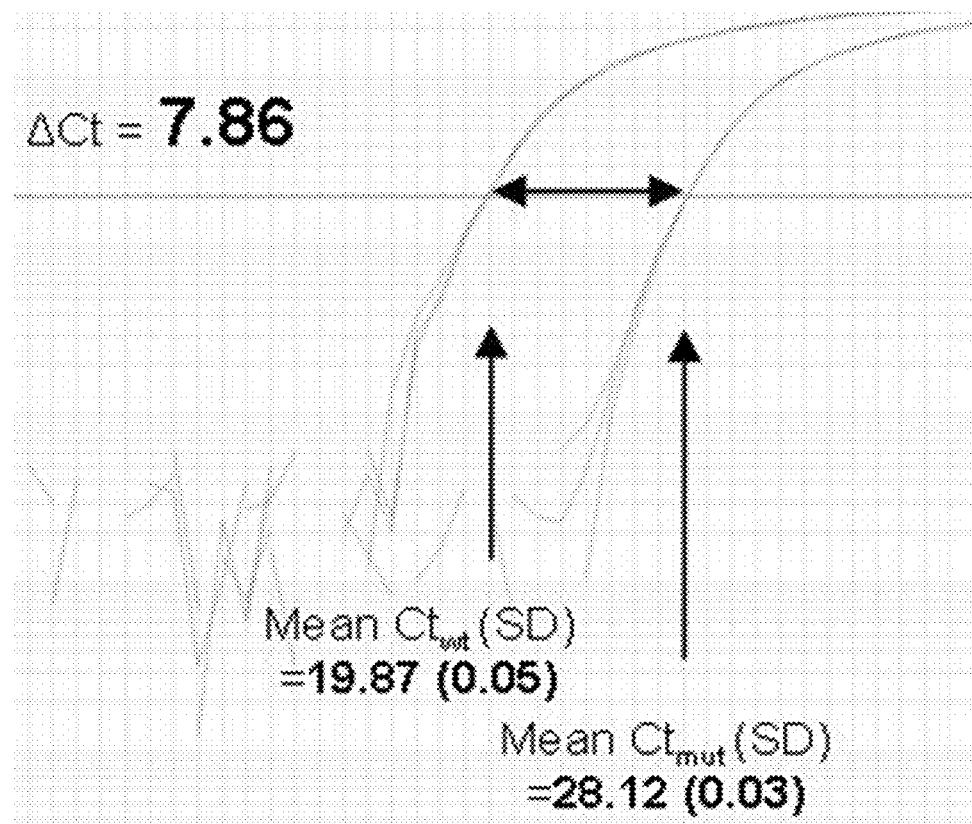
FIG. 22 depicts a plot used to determine the $\Delta Ct$ normalization value of a 0.5% V27A mixture.
Figure 23:
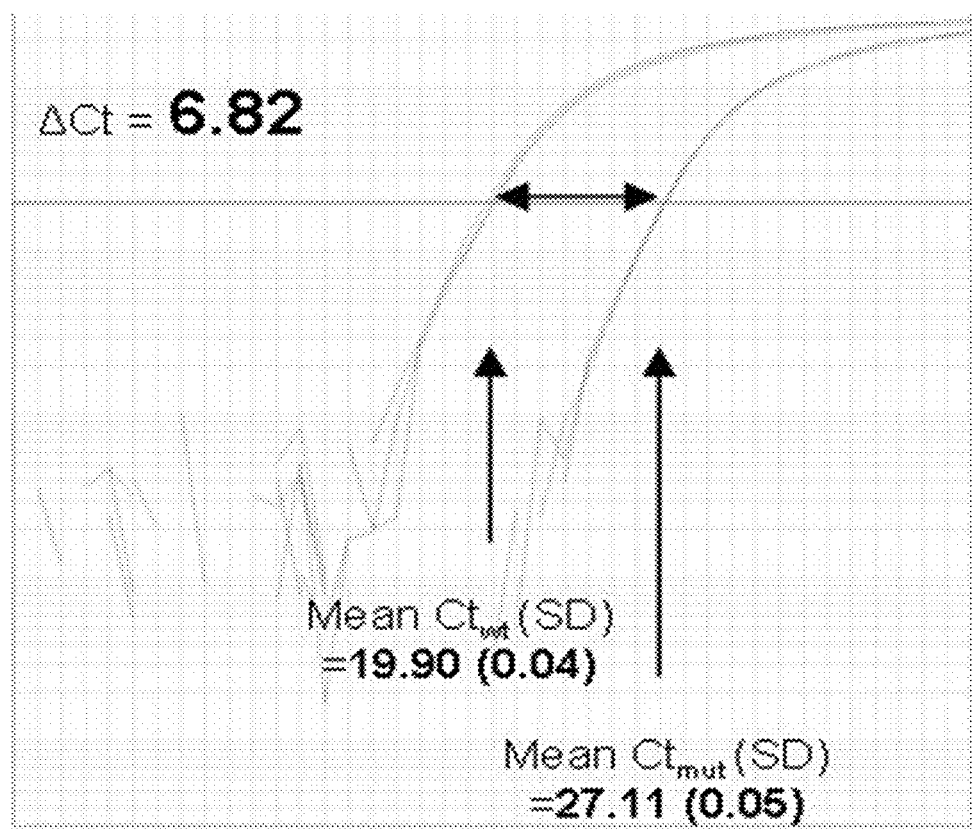
FIG. 23 depicts a plot used to determine the $\Delta Ct$ normalization value of a 1% V27A mixture.
Figure 24:
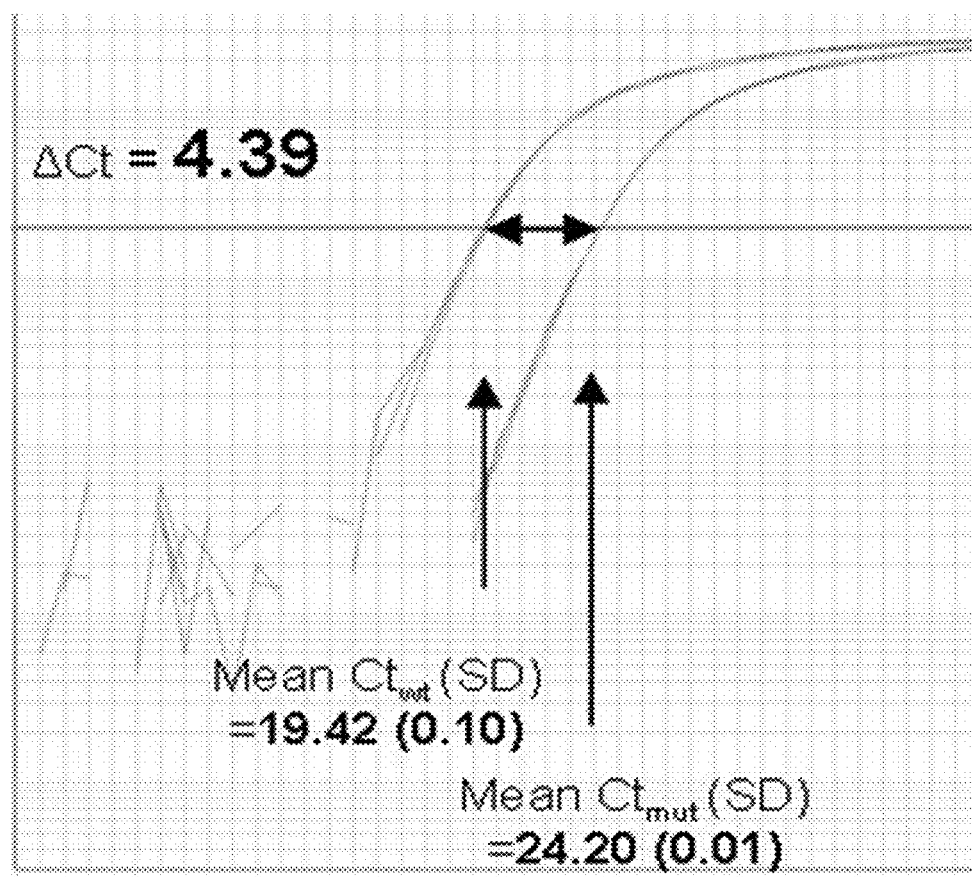
FIG. 24 depicts a plot used to determine the $\Delta Ct$ normalization value of a 5% V27A mixture.
Figure 25:
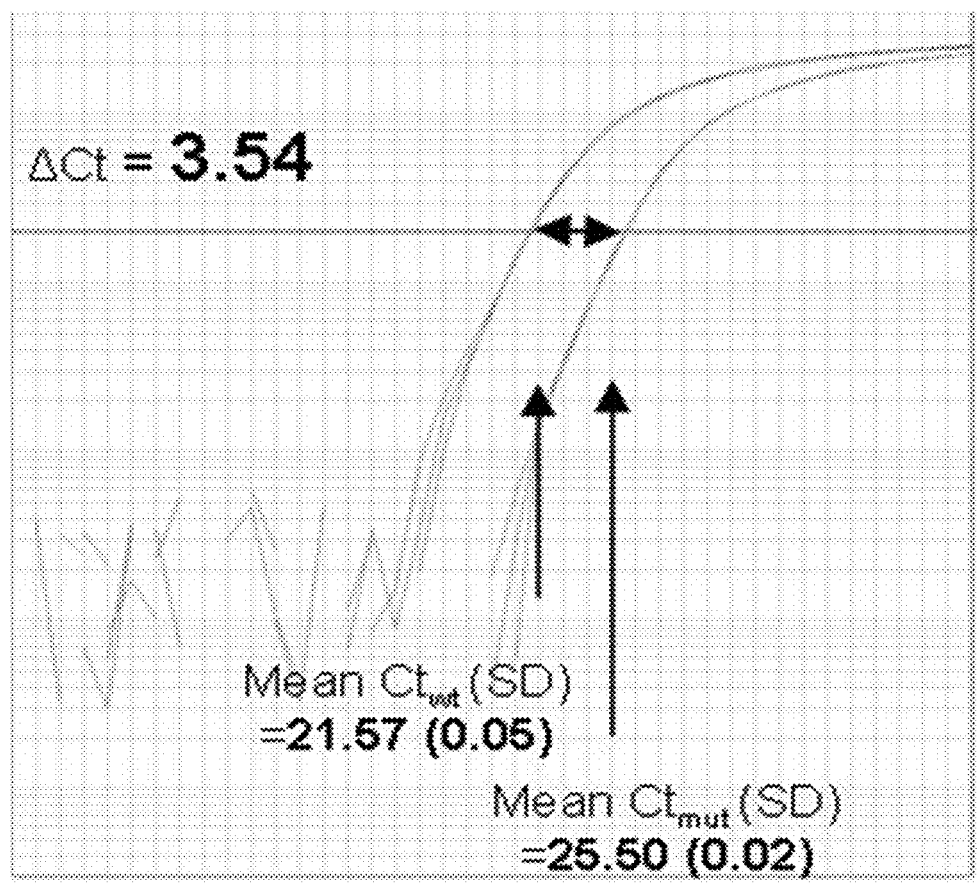
FIG. 25 depicts a plot used to determine the $\Delta Ct$ normalization value of a 10% V27A mixture.

FIGS. 20-25 depict the application of the V27A FluMAMA assay to prepared mixtures of V27A mutation DNA and sensitive DNA. Sequential mixtures of mutant and wild-type alleles result in predictable changes in ΔCt. The % mutant (95% CI) was estimated using pure standards and known mixtures: In FIG. 20, using data from a 50% V27A mutation mixture, a normalization value of 0.39 was determined for the V27A FluMAMA. FIG. 21 depicts the results of the assay using a 0.25% V27A mutation mixture that yields a V27A percentage of 0.24% (0.22, 0.26), FIG. 22 depicts the results using a 0.5% V27A mixture that yields a V27A percentage of 0.43% (0.41, 0.45), FIG. 23 depicts a 1.0% V27A mixture that yields a V27A percentage of 0.88% (0.83, 0.93). FIG. 24 depicts the results using a 5% V27A mixture that yields a V27A percentage of 4.57% (4.24, 4.91). FIG. 25 depicts the results using a 10% V27A mixture that yields a V27A percentage of 8.93% (8.69, 9.17).

Figure 26:
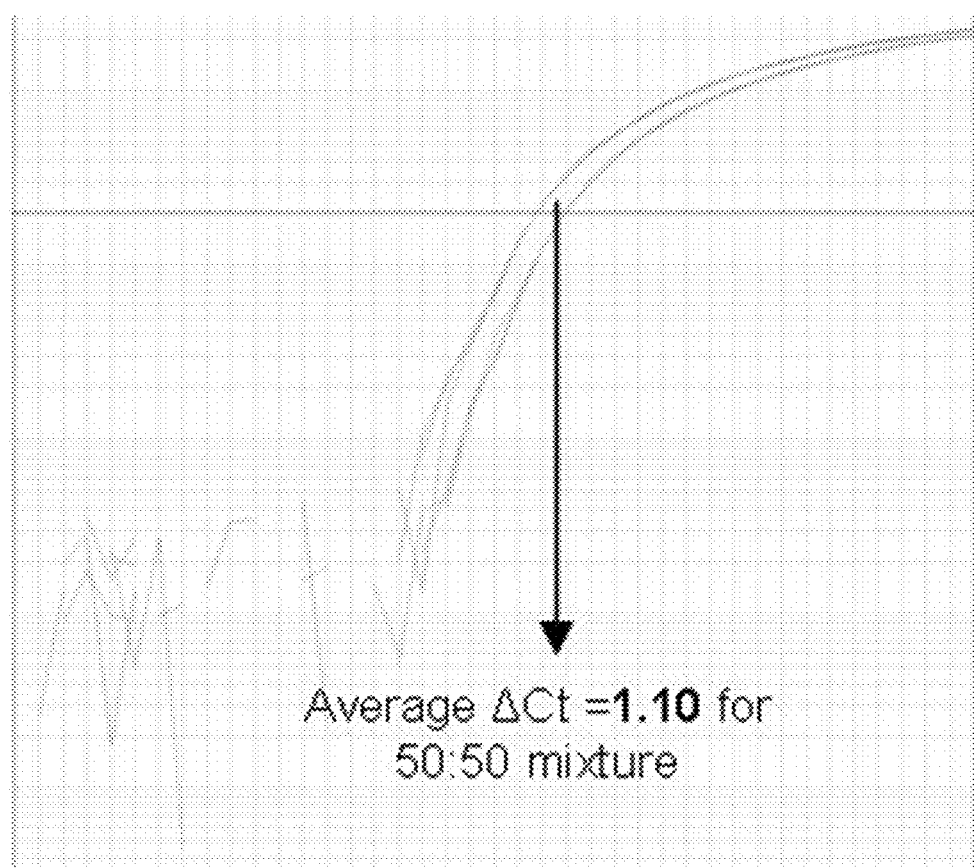
FIG. 26 depicts a plot used to determine the $\Delta Ct$ normalization value of a of a 50% L26F mutant mixture.
Figure 27:
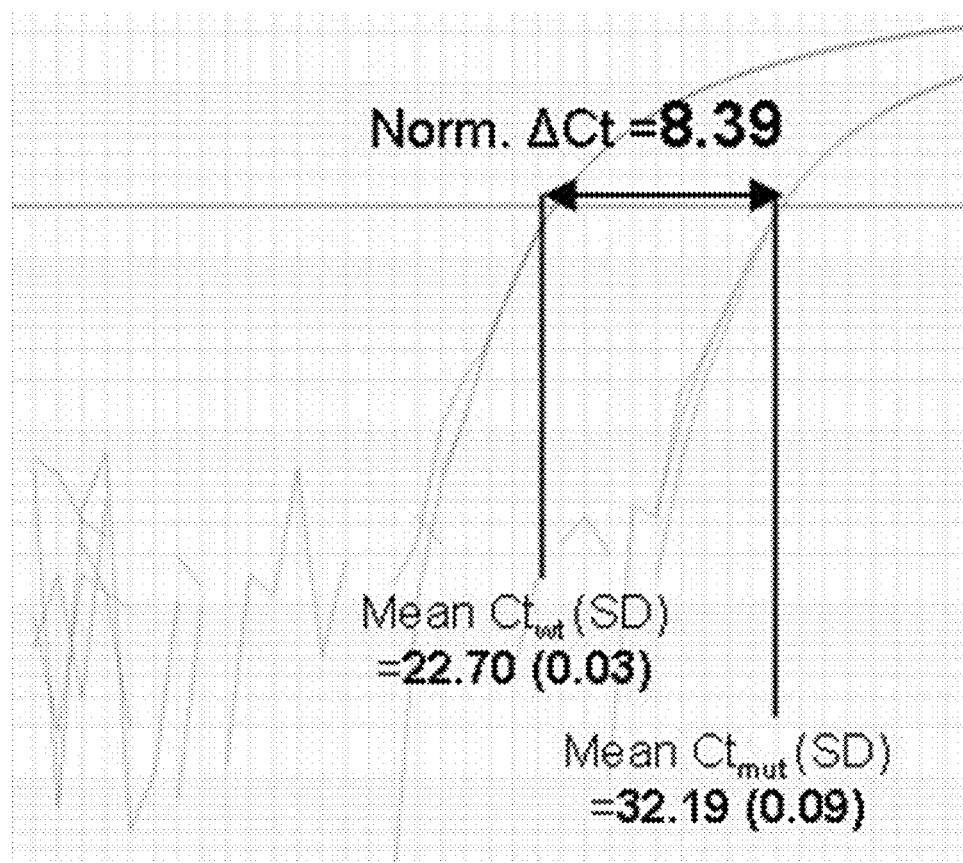
FIG. 27 depicts a plot used to determine the $\Delta Ct$ normalization value of a 0.25% L26F mixture.
Figure 28:
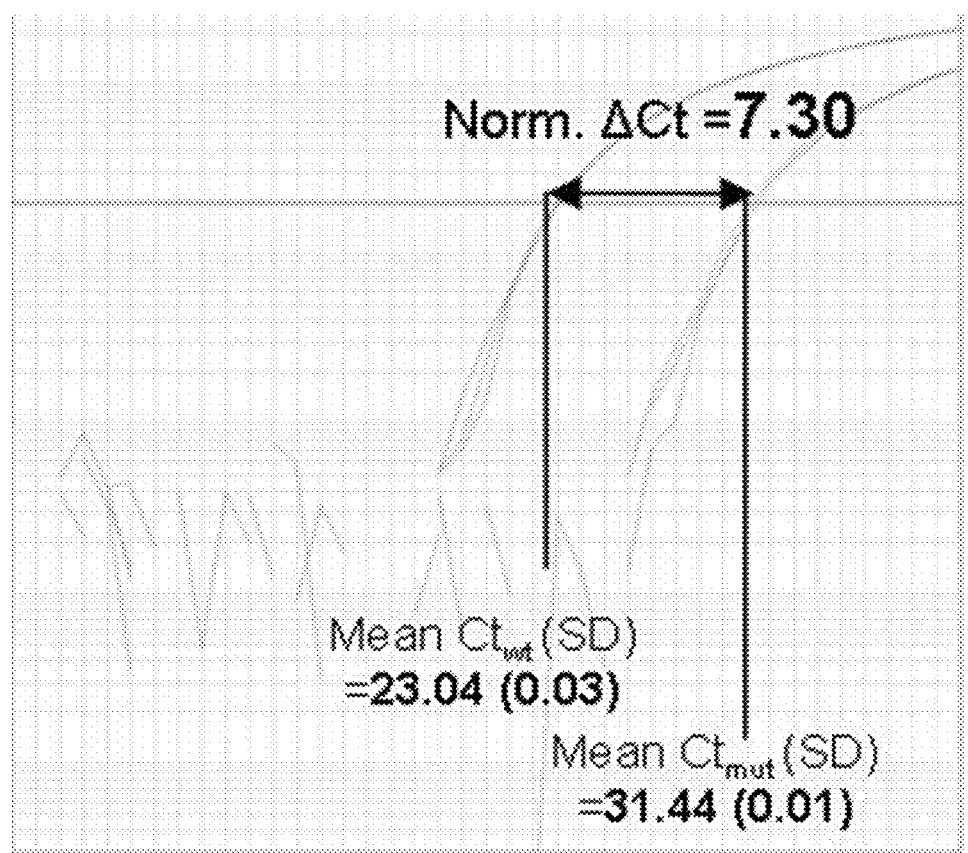
FIG. 28 depicts a plot used to determine the $\Delta Ct$ normalization value of a 0.5% L26F mixture.
Figure 29:
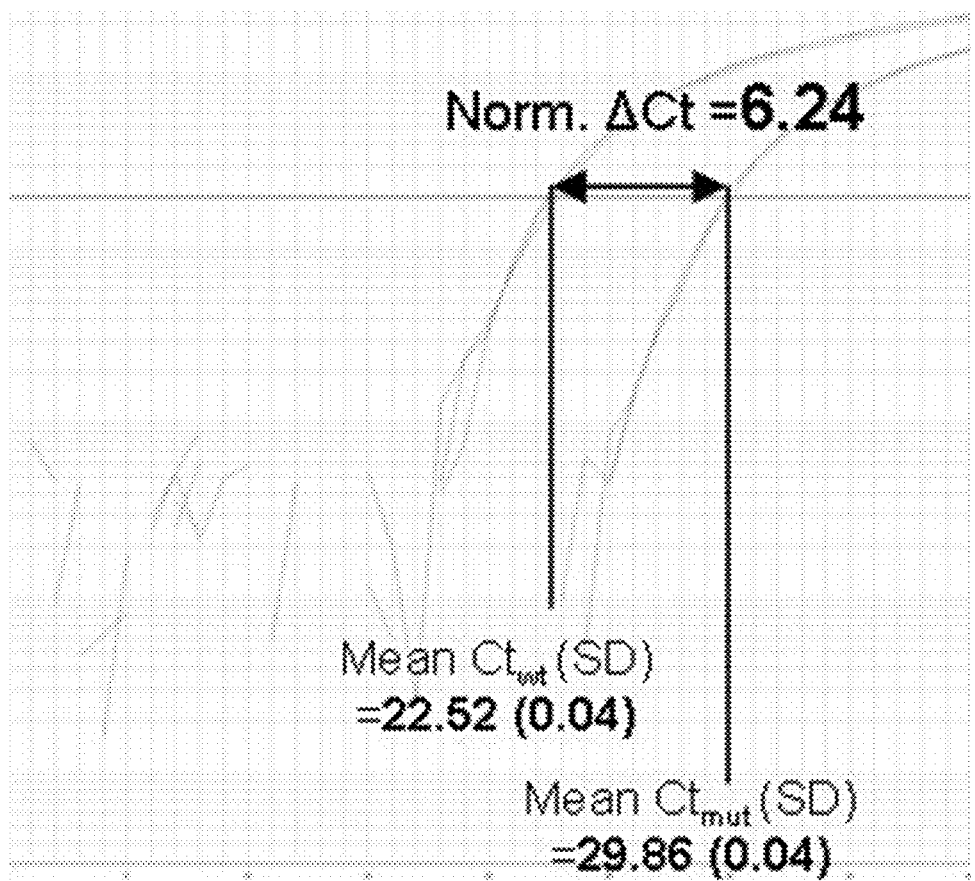
FIG. 29 depicts a plot used to determine the $\Delta Ct$ normalization value of a 1% L26F mixture.
Figure 30:
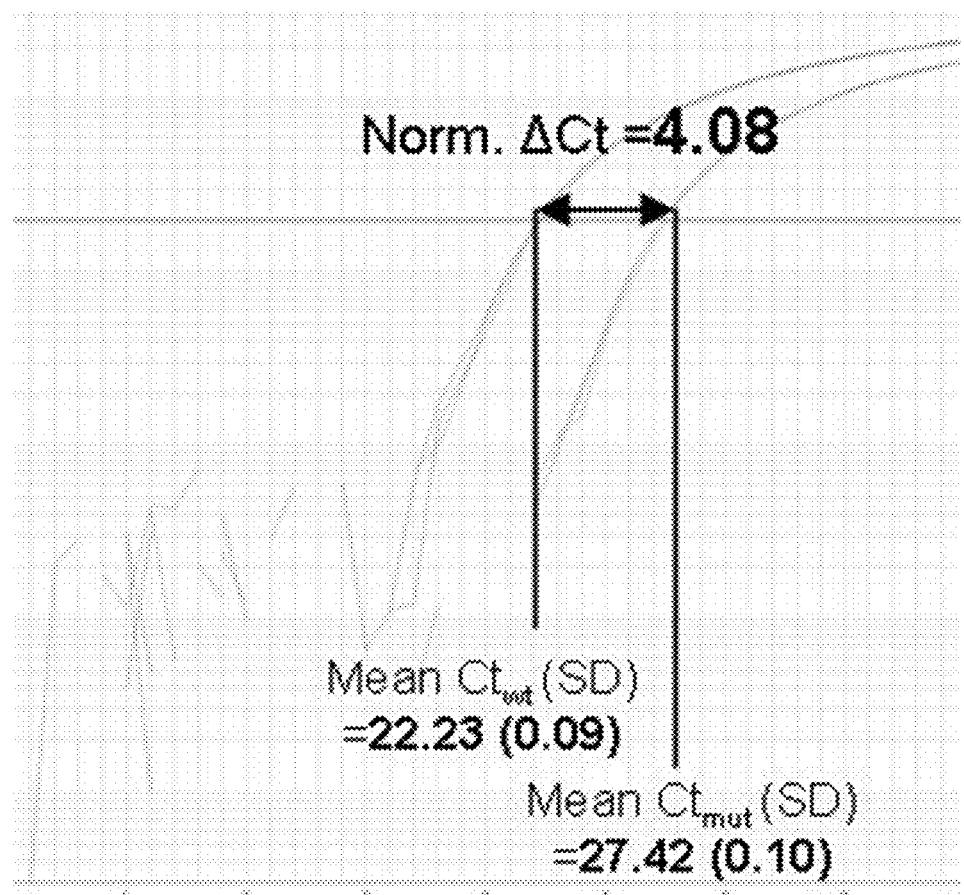
FIG. 30 depicts a plot used to determine the $\Delta Ct$ normalization value of a 5% L26F mixture.
Figure 31:
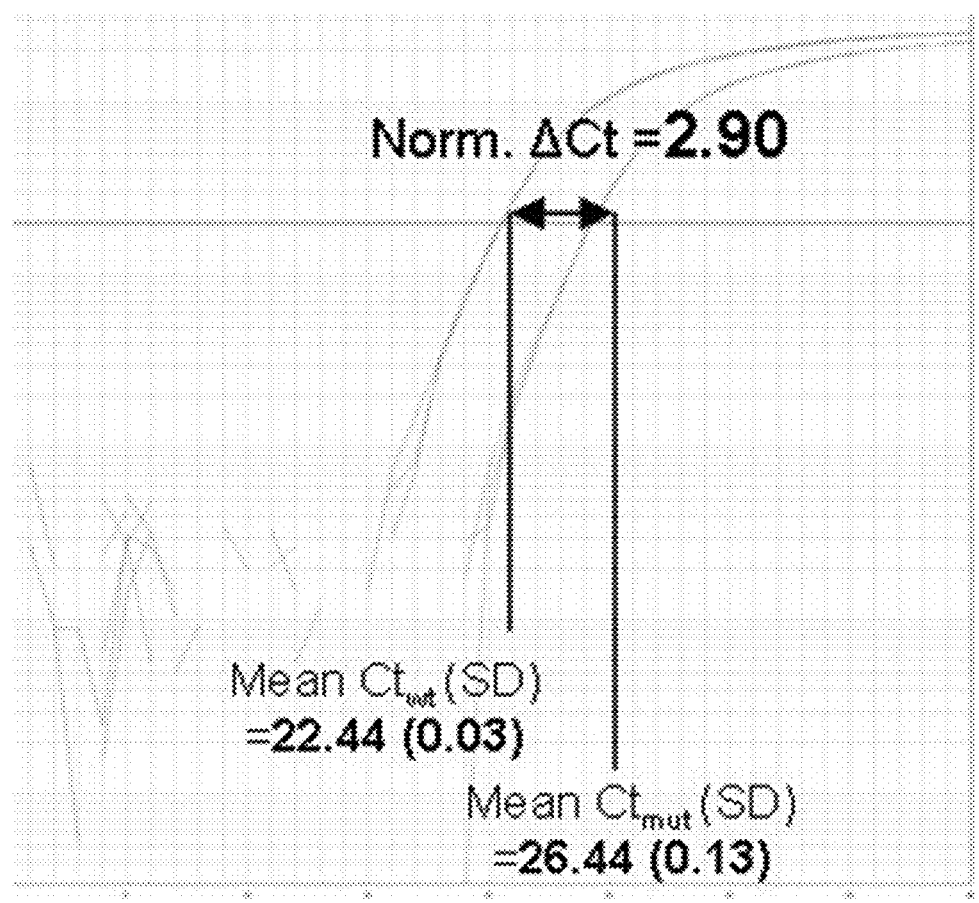
FIG. 31 depicts a plot used to determine the $\Delta Ct$ normalization value of a 10% L26F mixture.

FIGS. 26-31 depict the application the L26F FluMAMA assay to known mixtures of sensitive and L26F plasmid standards. In FIG. 26, data from a 50% L26F mixture was used to calculate a normalization value of 1.1. FIG. 27 depicts a 0.25% L26F mixture that yields a L26F percentage of 0.30% (0.28, 0.32). FIG. 28 depicts a 0.5% L26F mixture that yields an L26F percentage of 0.63% (0.61, 0.65), FIG. 29 depicts a 1% L26F mixture that yields an L26F percentage of 1.30% (1.23, 1.38). FIG. 30 depicts a 5% L26F mixture that yields an L26F percentage of 5.57% (5.05, 6.14). FIG. 31 depicts a 10% L26F mixture that yields an L26F percentage of 11.81% (10.5, 13.3).

Figure 32:
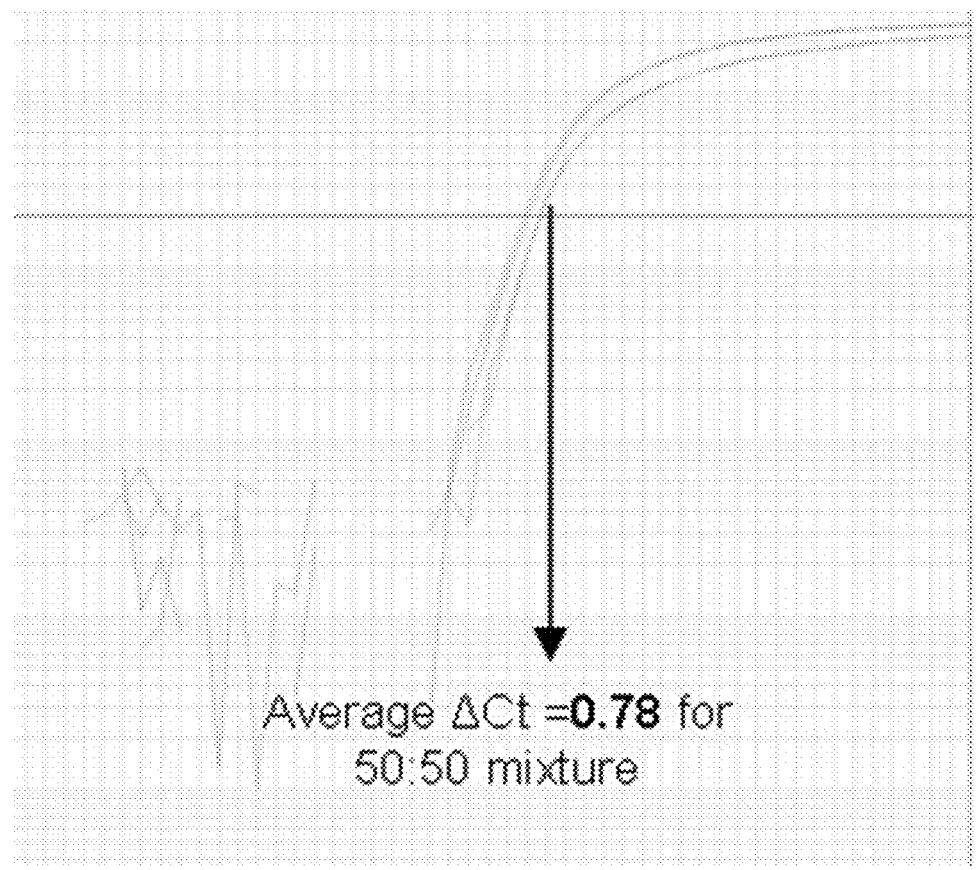
FIG. 32 depicts a plot used to determine the $\Delta Ct$ normalization value of a 50% A30T mixture.
Figure 33:
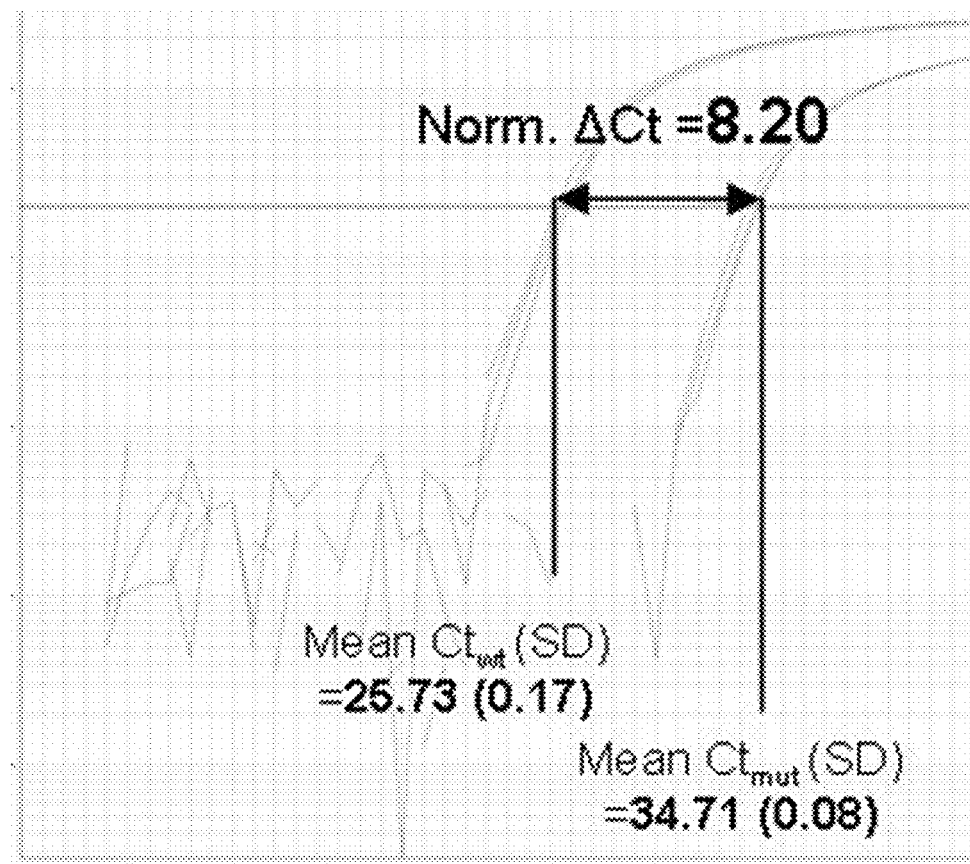
FIG. 33 depicts a plot used to determine the $\Delta Ct$ normalization value of a 0.25% A30T mixture.
Figure 34:
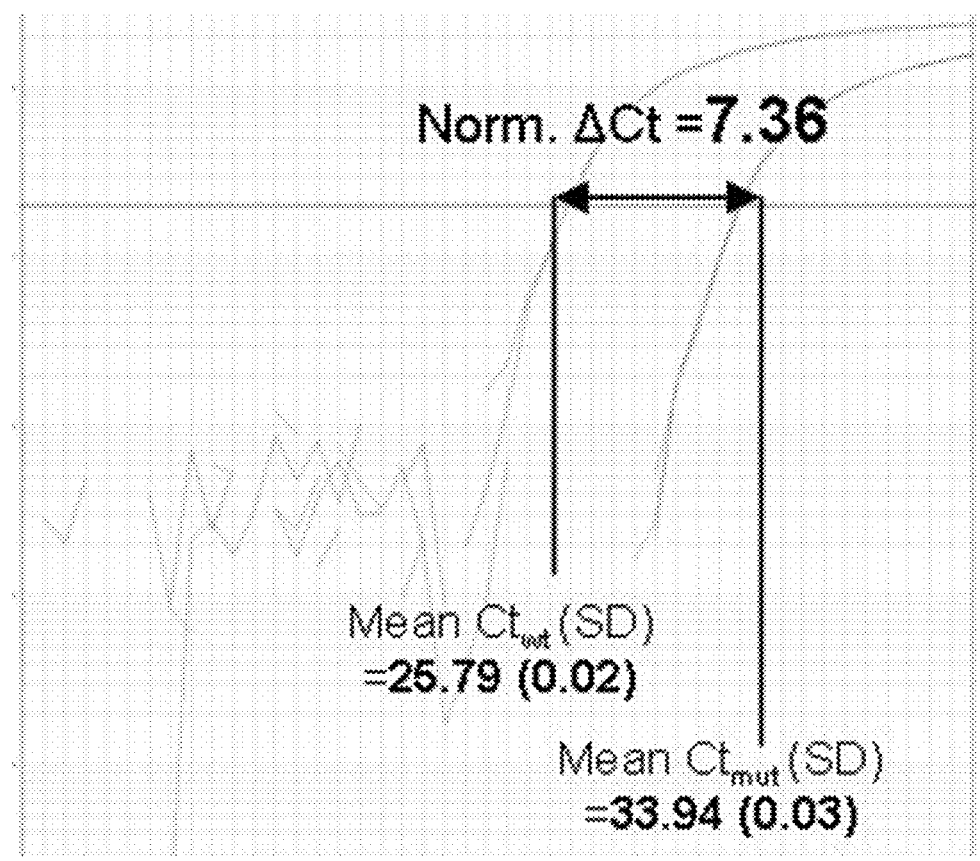
FIG. 34 depicts a plot used to determine the $\Delta Ct$ normalization value of a 0.5% A30T mixture.
Figure 35:
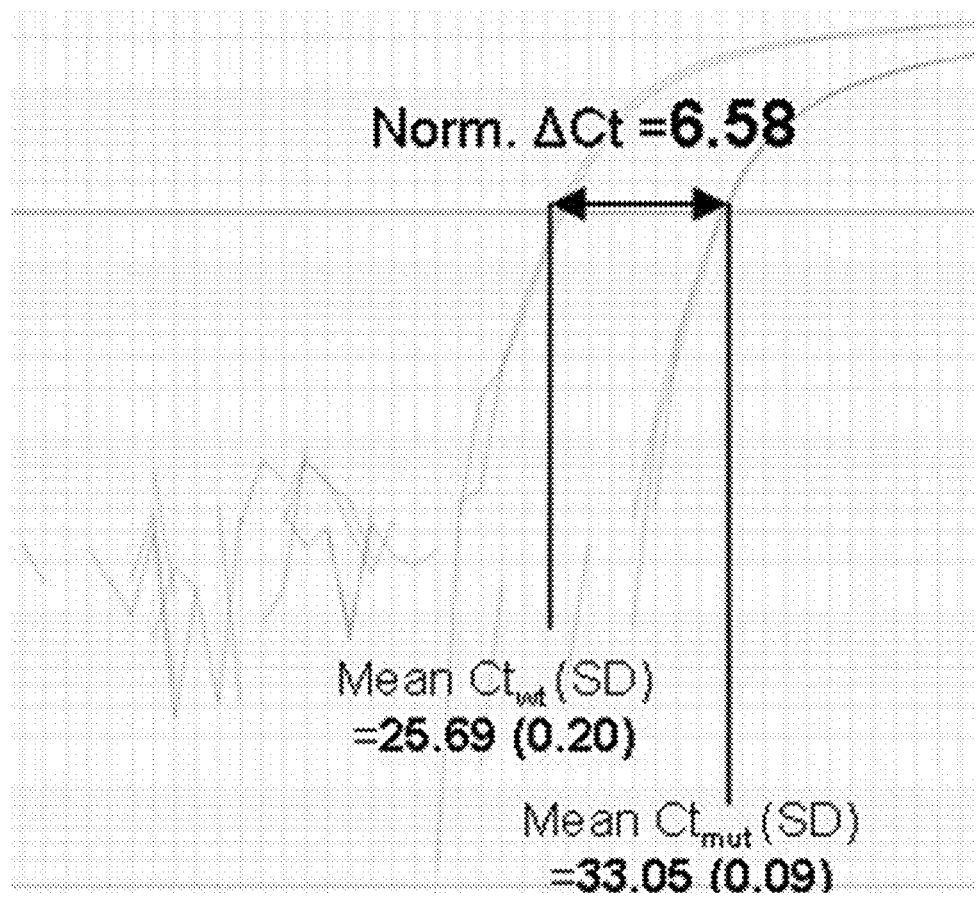
FIG. 35 depicts a plot used to determine the $\Delta Ct$ normalization value of a 1% A30T mixture.
Figure 36:
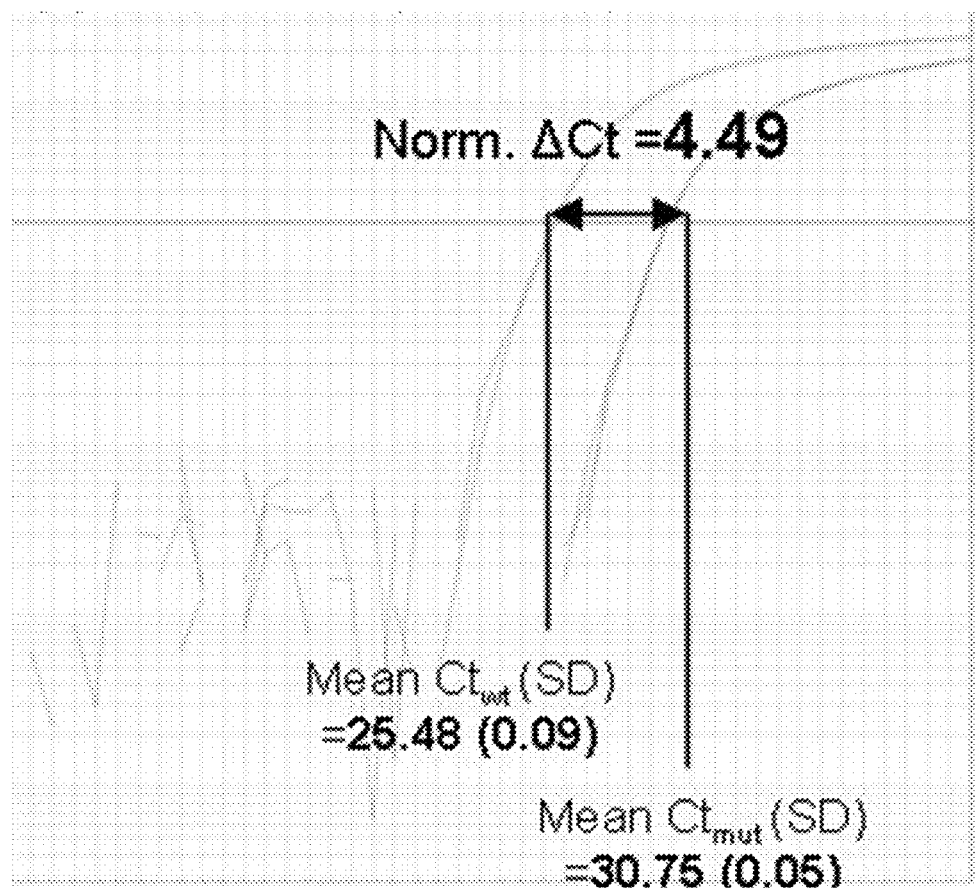
FIG. 36 depicts a plot used to determine the $\Delta Ct$ normalization value of a 5% A30T mixture.
Figure 37:
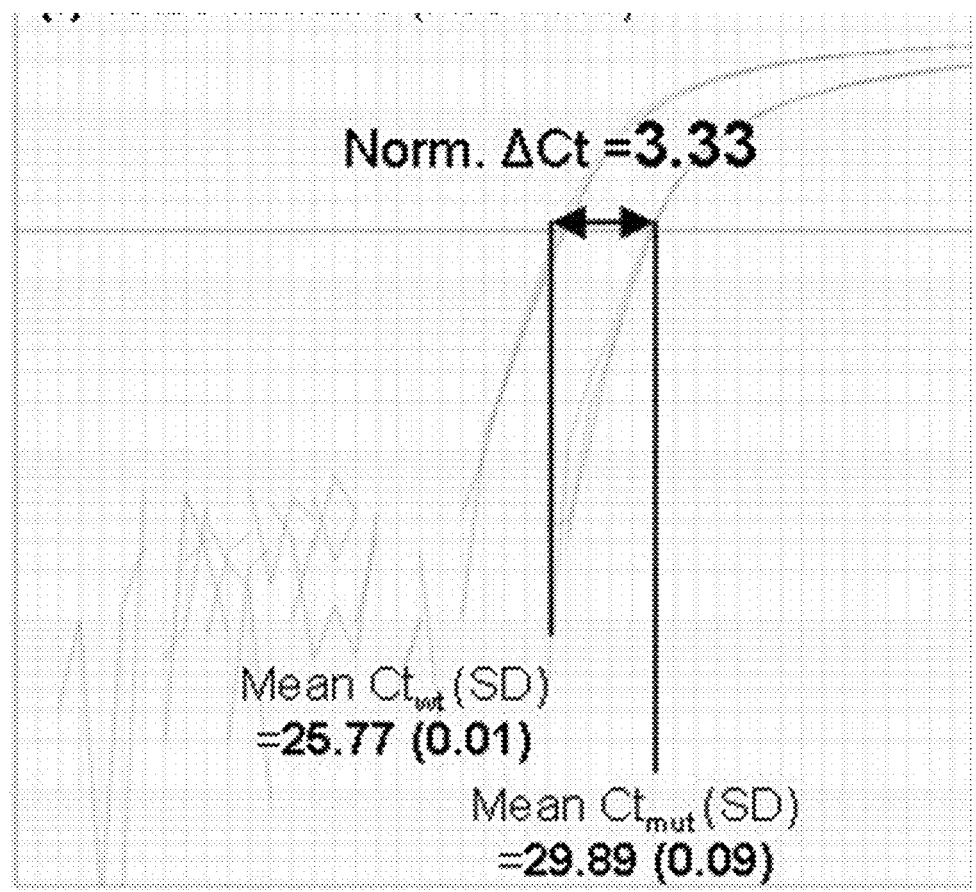
FIG. 37 depicts a plot used to determine the $\Delta Ct$ normalization value of a 10% A30T mixture.

FIGS. 32-37 depict the application of the A30T FluMAMA assay to premixed mixtures of sensitive and A30T DNA. In FIG. 32, a normalization value of 0.78 was calculated using a mixture with 50% A30T. In FIG. 33, a 0.25% A30T mixture yields an A30T percentage of 0.34% (0.28, 0.41). In FIG. 34, a 0.5% A30T mixture yields an A30T percentage of 0.60% (0.55, 0.66). In FIG. 35, a 1% A30T mixture yields an A30T percentage of 1.03% (0.87, 1.22). In FIG. 36, a 5% A30T mixture yields an A30T percentage of 4.26% (3.95, 4.58). In FIG. 31, a 10% A30T mixture yields an A30T percentage of 9.02% (8.27, 9.84).

Figure 38:
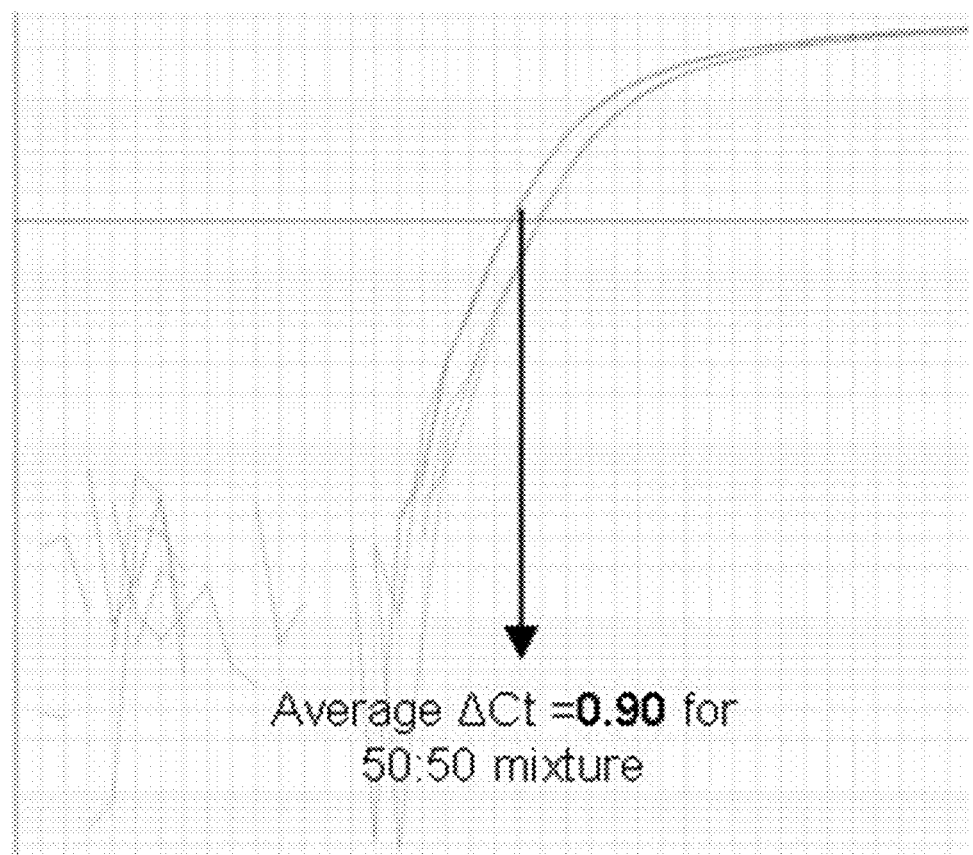
FIG. 38 depicts a plot used to determine the $\Delta Ct$ normalization value of a 50% S31N mixture.
Figure 39:
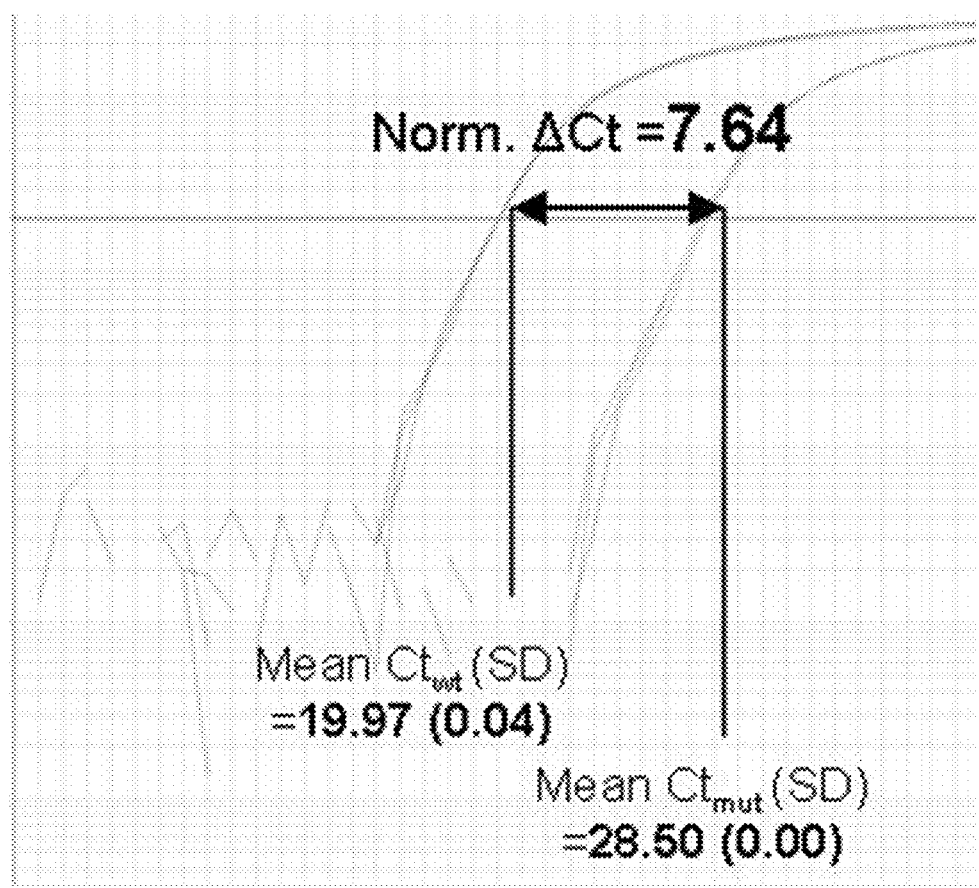
FIG. 39 depicts a plot used to determine the $\Delta Ct$ normalization value of a 0.25% S31N mixture.
Figure 40:
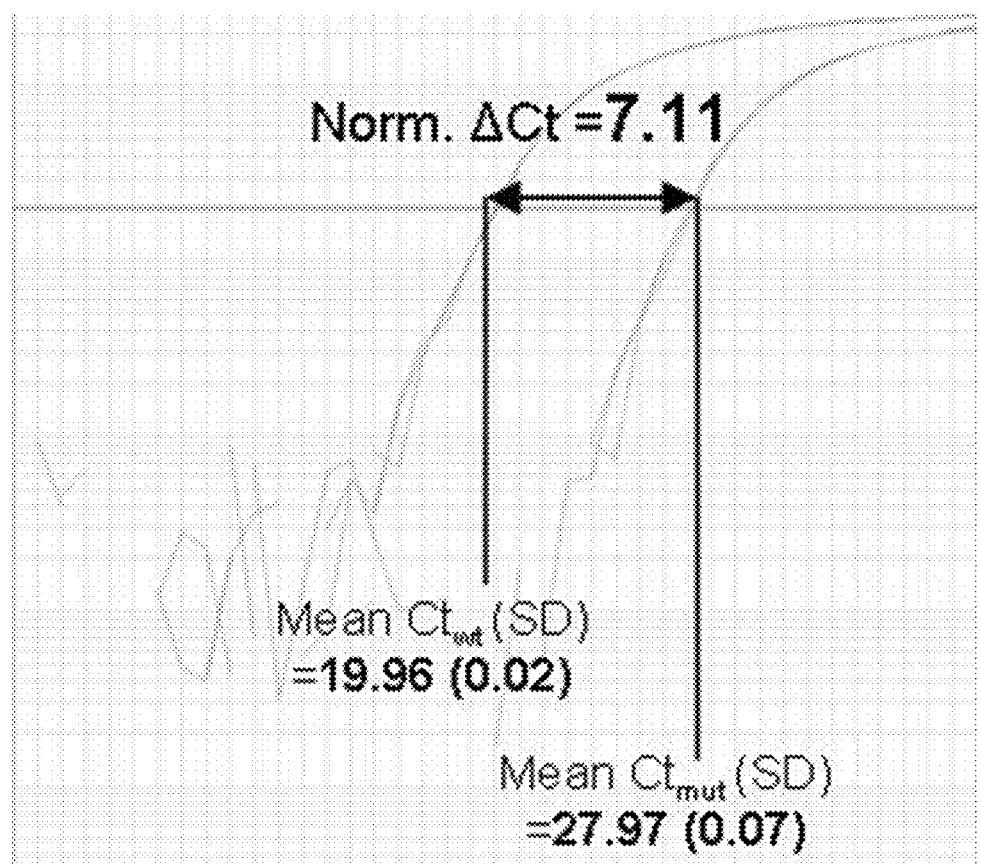
FIG. 40 depicts a plot used to determine the $\Delta Ct$ normalization value of a 0.5% S31N mixture.
Figure 41:
FIG. 41 depicts a plot used to determine the $\Delta Ct$ normalization value of a 1% S31N mixture.
Figure 42:
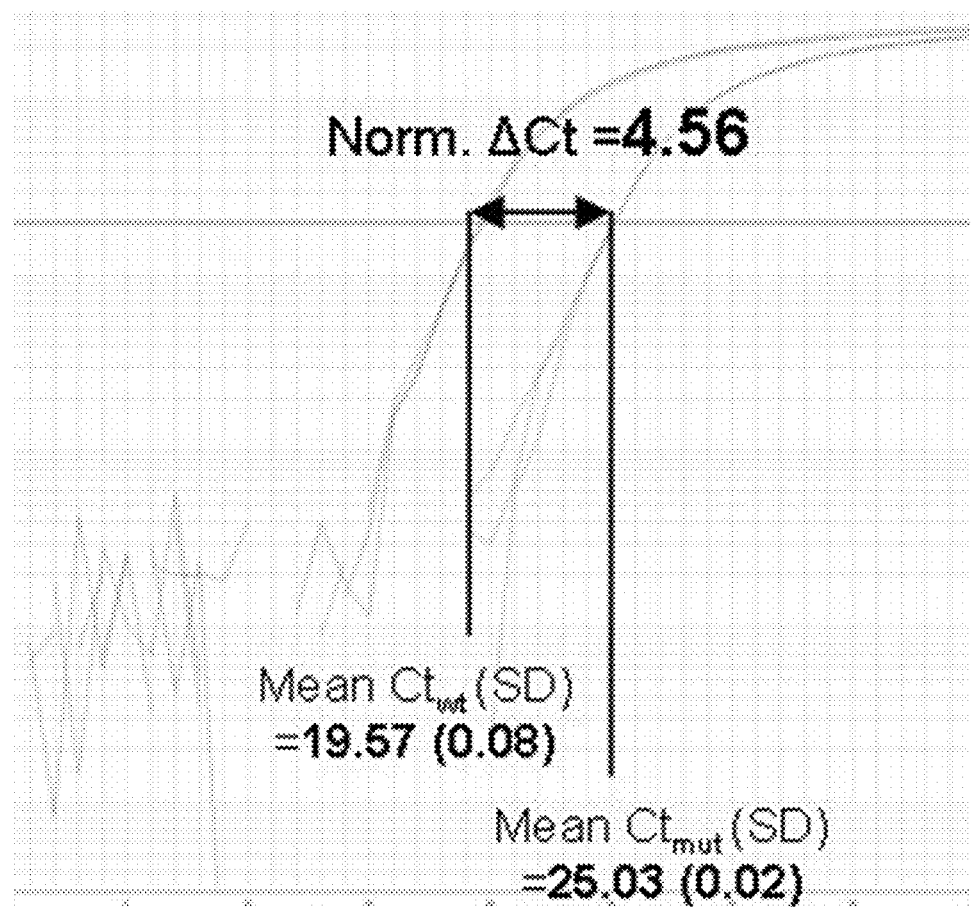
FIG. 42 depicts a plot used to determine the $\Delta Ct$ normalization value of a 5% S31N mixture.
Figure 43:
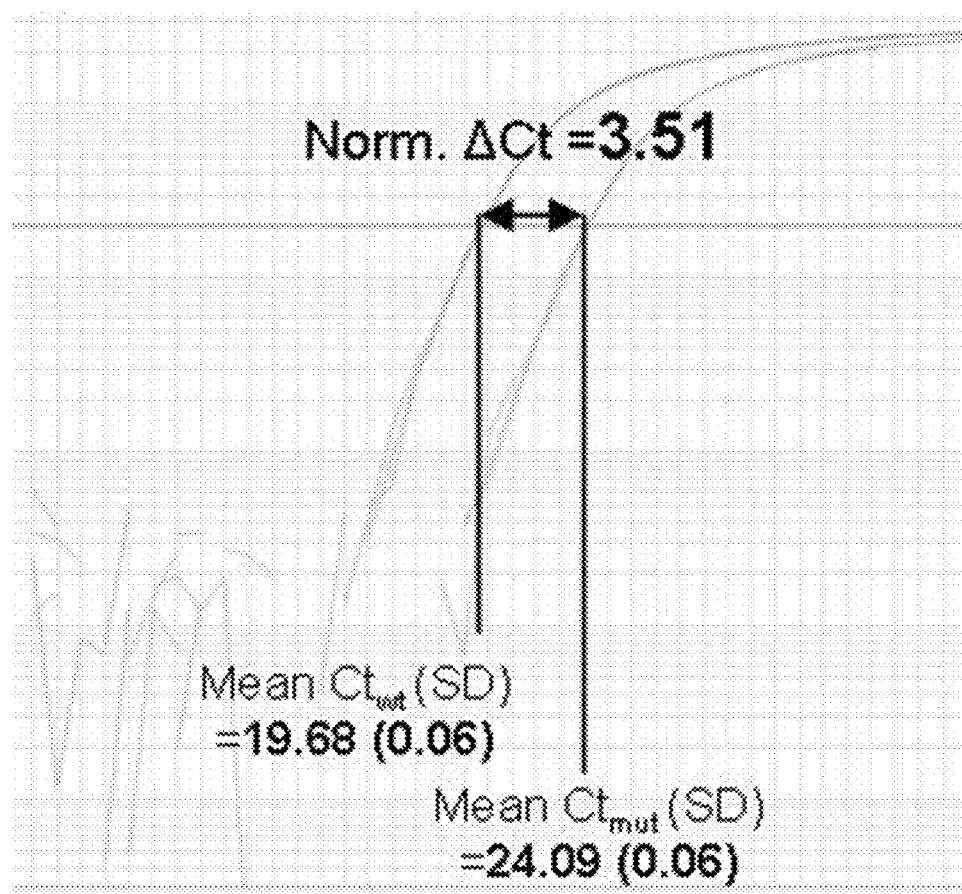
FIG. 43 depicts a plot used to determine the $\Delta Ct$ normalization value of a 10% S31N mixture.

FIGS. 38-43 depict data showing the application of S31N FluMAMA to known mixtures of wild-type and S31N plasmid standards. In FIG. 38, a normalization value of 0.90 was calculated from a mixture containing 50% S31N DNA. In FIG. 39, a 0.25% S31N mixture yields an S31N percentage of 0.50% (0.48, 0.52). In FIG. 40, a 0.5% S31N mixture yields an S31N percentage of 0.72% (0.68, 0.76), In FIG. 341, a 1% S31N mixture yields an S31N percentage of 1.06% (1.01, 1.12). In FIG. 42, a 5% S31N mixture yields an S31N percentage of 4.08% (3.82, 4.35). In FIG. 43, a 10% S31N mixture yields an S31N percentage of 8.08% (7.61, 8.57).

Figure 44:
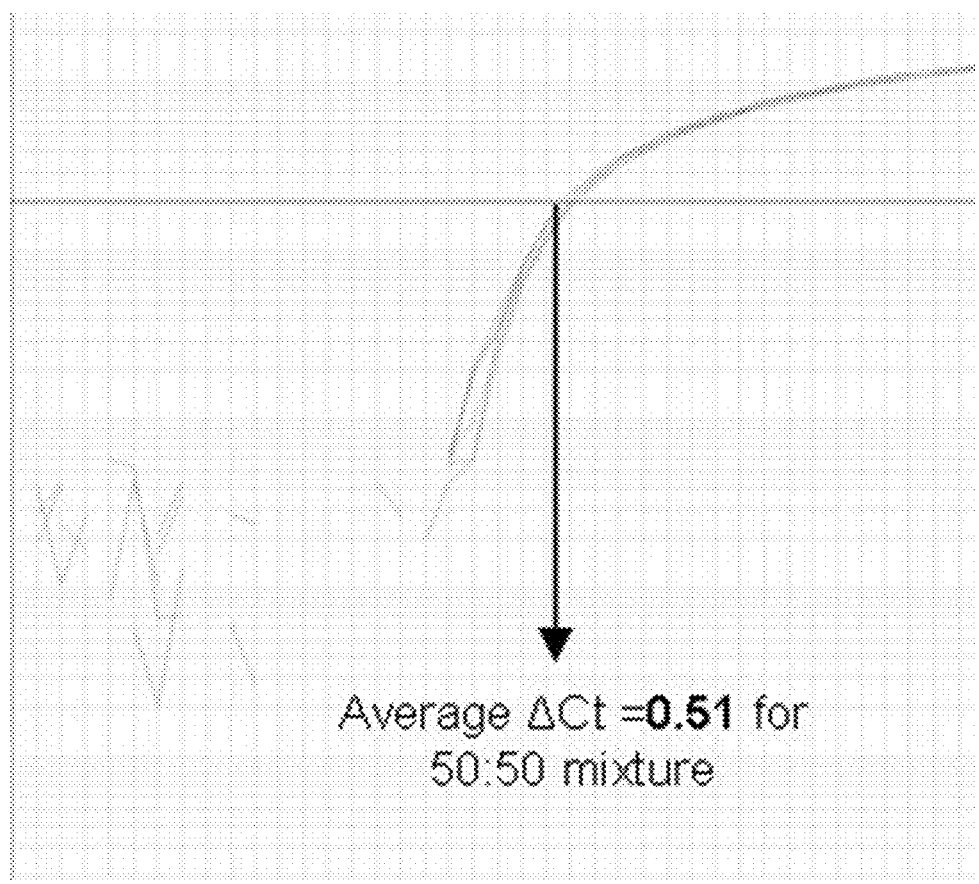
FIG. 44 depicts a plot used to determine the $\Delta Ct$ normalization value of a 50% H274Y mixture.
Figure 45:
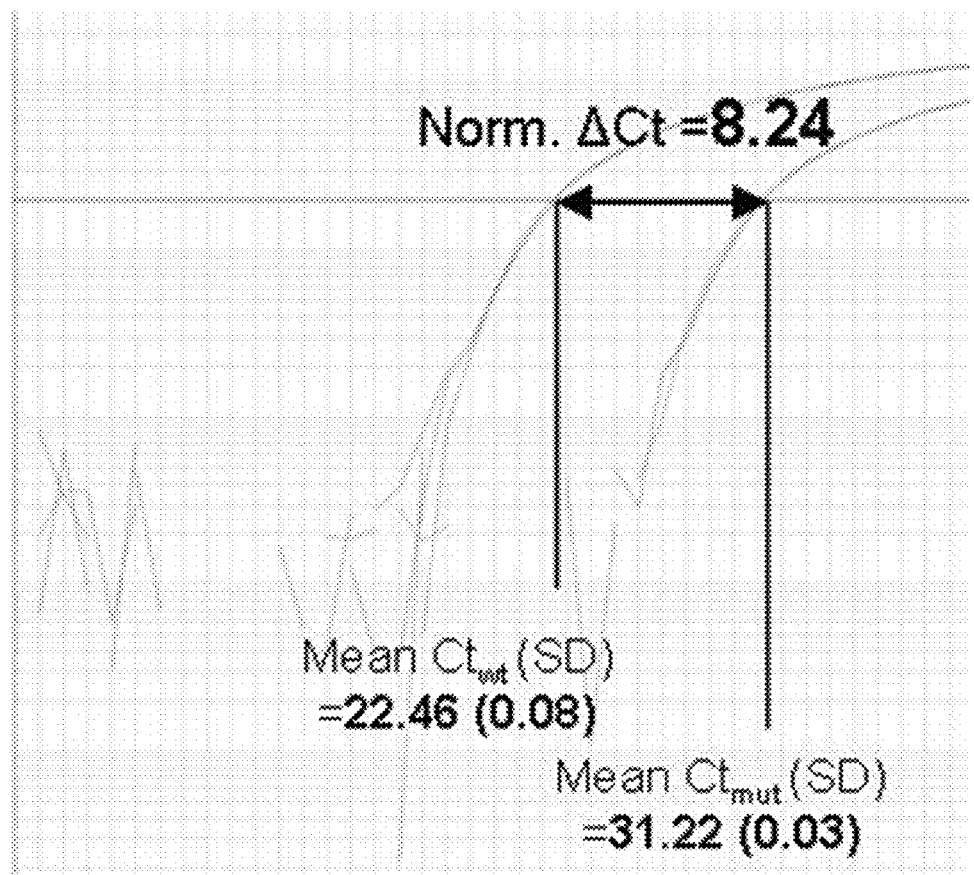
FIG. 45 depicts a plot used to determine the $\Delta Ct$ normalization value of a 0.25% H274Y mixture.
Figure 46:
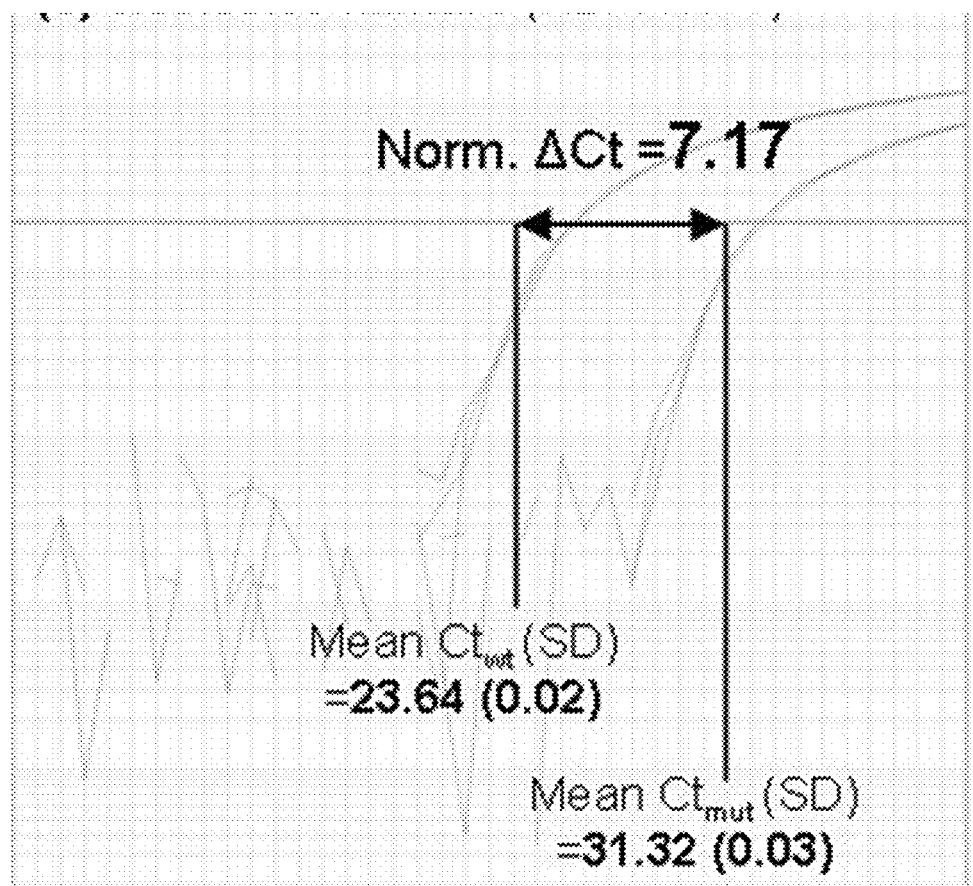
FIG. 46 depicts a plot used to determine the $\Delta Ct$ normalization value of a 0.5% H274Y mixture.
Figure 47:
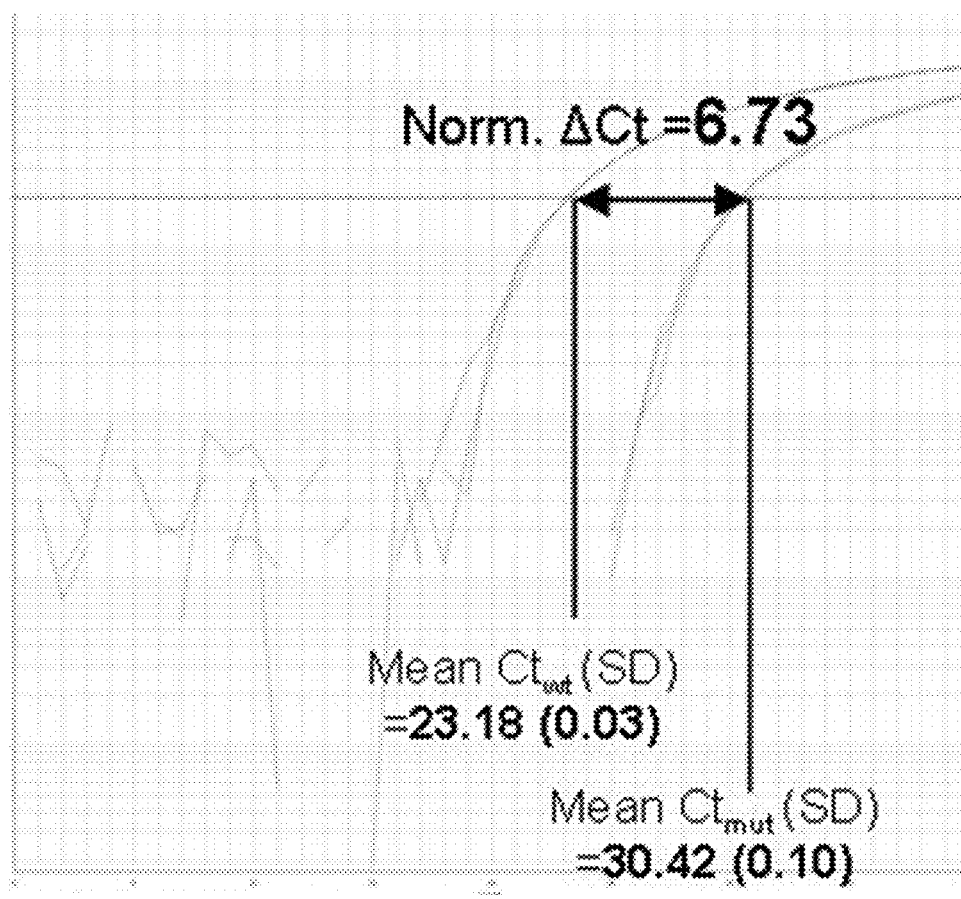
FIG. 47 depicts a plot used to determine the $\Delta Ct$ normalization value of a 1% H274Y mixture.
Figure 48:
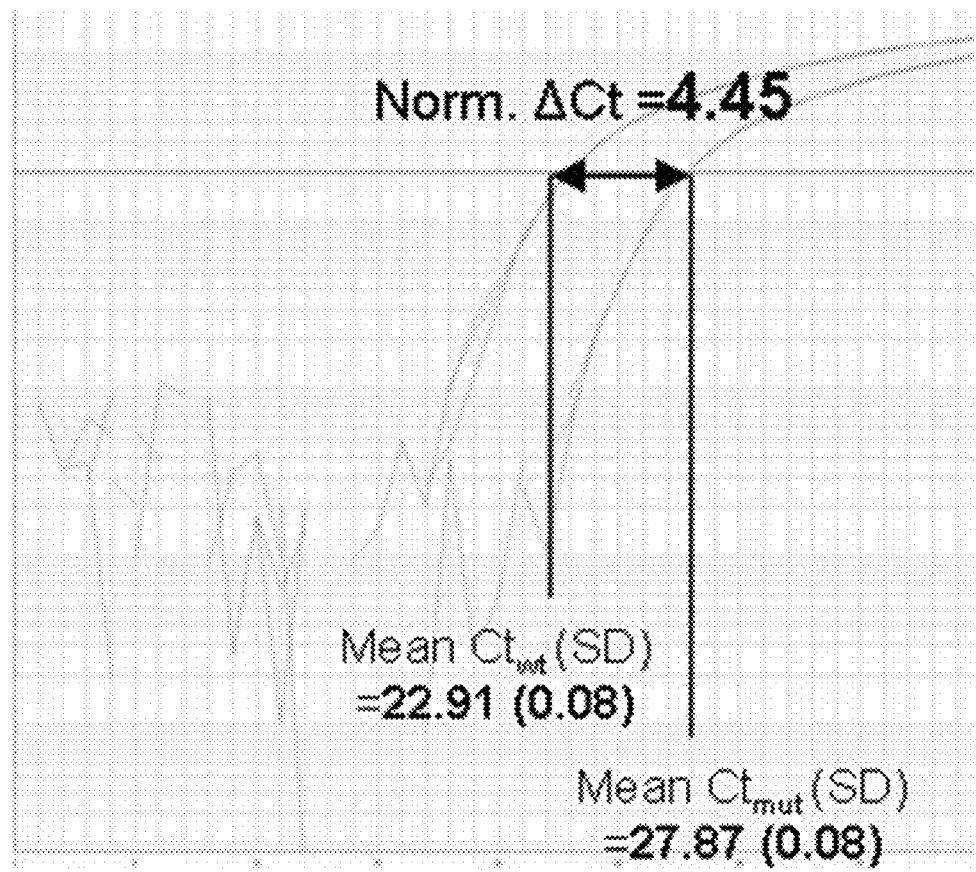
FIG. 48 depicts a plot used to determine the $\Delta Ct$ normalization value of a 5% H274Y mixture.
Figure 49:
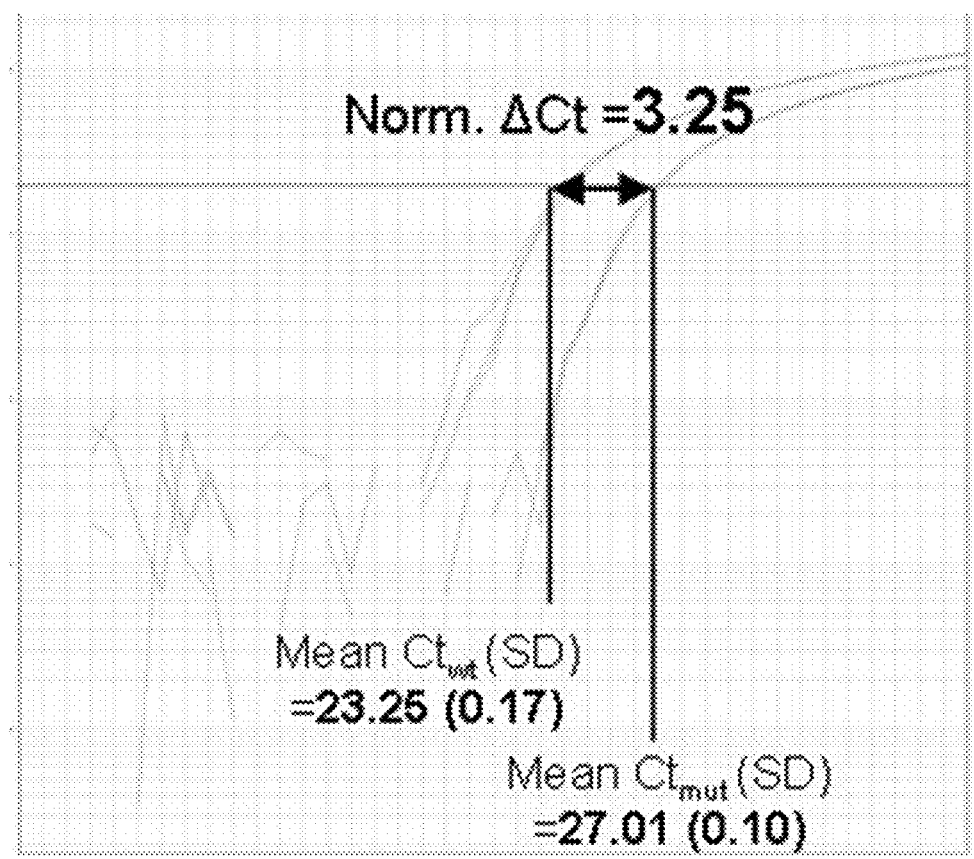
FIG. 49 depicts a plot used to determine the $\Delta Ct$ normalization value of a 10% H274Y mixture.

FIGS. 44-49 depict data showing the application of H274Y FluASMA to known mixtures of wild-type and H274Y plasmid standards. In FIG. 44, a normalization value of 0.51 was calculated from a mixture containing 50% H274Y DNA. In FIG. 45, a 0.25% H274Y mixture yielded an H274Y percentage of 0.33% (0.30, 0.36). In FIG. 46, a 0.5% H274Y mixture yielded an H274Y percentage of 0.69% (0.67, 0.71). In FIG. 47 a 1% H274Y mixture yielded an H274Y percentage of 0.93% (0.86, 1.01). In FIG. 48, a 5% H274Y mixture yielded an H274Y percentage of 4.38% (4.02, 4.76). In FIG. 49, a 10% H274Y mixture yielded an H274Y percentage of 9.49 (8.24, 10.90).

Assay Validation

FluMAMA qPCR results from assays targeting each mutation from the three separate qPCR runs meeting were used to calculate a resistant:sensitive ratio and a 95% confidence interval. Validation results are summarized below.

Validation results are summarized in Tables 2 through 7. Table 2 shows the number of copies of cDNA/rxn present in the pre-made mixtures. The lower limit of detection for all of the assays is between 0.5% and 0.25% resistant copies in a total concentration of $10^3$ copies/µl. Tables 3 through 7 shows the theoretical lower limit of detection of each subtype in each assay. In table 3, the validation of the lower limit of detecting a L26F mutation was in a mixture with a ratio of resistant:sensitive of 0.025 and at a total DNA concentration of $10^3$ copies/µl. The theoretical lower limit of detecting a L26F mutation was $3.8 \times 10^{-6}$ at a total DNA concentration of $10^7$ copies per µl. In Table 4, the lower limit of detecting a V27A mutation was in a mixture with a ratio of resistant:sensitive of 0.25 at a total DNA concentration of $10^3$ copies/µl. The theoretical lower limit of detecting a V27A mutation is in a mixture with a ratio of resistant:sensitive of 0.001 at a total DNA concentration of $2 \times 10^3$ copies/µl. In Table 5, the lower limit of detecting an A30T mutation was in a mixture with a ratio of resistant:sensitive of 0.0025 at a total DNA concentration of $10^3$ copies/µl and the theoretical lower limit of detecting an A30T mutation was the same as the observed lower limit. In Table 6, the lower limit of detecting an S31N mutation is in a mixture with a ratio of resistant:sensitive of 0.005 and a total DNA concentration of $10^3$ copies/µl. Note, however, that the assay can differentiate a mixture with a resistant:sensitive ratio of 0.0025 from a mixture that contains no resistant mutations. The theoretical lower limit of detection is equivalent to the observed lower limit. In Table 7, the lower limit of detecting an H274Y mutation is in a mixture with a ratio of resistant:sensitive of 0.0025 at a total DNA concentration $10^3$ copies/µl. The theoretical lower limit of detecting an H274Y mutation is in a mixture with a ratio of resistant:sensitive of $4.88 \times 10^{-4}$ at a total DNA concentration of $5 \times 10^3$ copies/µl.

TABLE 1

Resistant mutation copy number in a single reaction well for each resistant mutation frequency at each DNA concentration

| r:s Ratio | $10^9$ copies/µl | $10^7$ copies/µl | $10^5$ copies/µl | $10^4$ copies/µl | $10^3$ copies/µl | $10^2$ copies/µl | $10^1$ copies/µl |
|---|---|---|---|---|---|---|---|
| 0.50 | $5 \times 10^8$ | $5 \times 10^6$ | $5 \times 10^4$ | 5000 | 500 | 50 | 5 |
| 0.10 | $1 \times 10^8$ | $1 \times 10^6$ | $1 \times 10^4$ | 1000 | 100 | 10 | 1* |
| 0.05 | $5 \times 10^7$ | $5 \times 10^5$ | 5000 | 500 | 50 | 5 | 0.5* |
| 0.01 | $1 \times 10^7$ | $1 \times 10^5$ | 1000 | 100 | 10 | 1* | 0.1* |
| 0.005 | $5 \times 10^6$ | $5 \times 10^4$ | 500 | 50 | 5 | 0.5* | 0.05* |
| 0.0025 | $2.5 \times 10^6$ | $2.5 \times 10^4$ | 250 | 25 | 2.5 | 0.25* | 0.025* |

*At ≤ one copy level, mutant detection can be a result the Poisson sampling probability or stochastic effect, i.e. a non-deterministic, unpredictable process.

TABLE 2

L26F FluMAMA

| r:s Ratio | $10^9$ copies/µl | $10^7$ copies/µl | $10^5$ copies/µl | $10^4$ copies/µl | $10^3$ copies/µl | $10^2$ copies/µl | $10^1$ copies/µl |
|---|---|---|---|---|---|---|---|
| 0.50 | + | + | + | + | + | + | + |
| 0.10 | + | + | + | + | + | + | − |

TABLE 2-continued

L26F FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.05 | + | + | + | + | + | + | + |
| 0.01 | + | + | + | + | + | + | − |
| 0.005 | + | + | + | + | + | − | − |
| 0.0025 | + | + | + | + | + | − | − |

+ indicates detection of mutation conferring antiviral drug resistance
− indicates no detection of mutation conferring antiviral drug resistance

TABLE 3

V27A FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.50 | + | + | + | + | + | + | + |
| 0.10 | + | + | + | + | + | + | + |
| 0.05 | + | + | + | + | + | + | − |
| 0.01 | + | + | + | + | + | + | − |
| 0.005 | + | + | + | + | + | − | − |
| 0.0025 | + | + | + | + | + | − | − |

+ indicates detection of mutation conferring antiviral drug resistance
− indicates no detection of mutation conferring antiviral drug resistance

TABLE 4

A30T FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.50 | + | + | + | + | + | + | + |
| 0.10 | + | + | + | + | + | + | + |
| 0.05 | + | + | + | + | + | + | − |
| 0.01 | + | + | + | + | + | − | − |
| 0.005 | + | + | + | + | + | − | − |
| 0.0025 | + | + | + | + | + | − | − |

+ indicates detection of mutation conferring antiviral drug resistance
− indicates no detection of mutation conferring antiviral drug resistance

TABLE 5

S31N FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.50 | + | + | + | + | + | + | + |
| 0.10 | + | + | + | + | + | + | + |
| 0.05 | + | + | + | + | + | + | + |
| 0.01 | + | + | + | + | + | − | − |
| 0.005 | + | + | + | + | + | − | − |
| 0.0025 | − | − | − | − | − | − | − |

+ indicates detection of mutation conferring antiviral drug resistance
− indicates no detection of mutation conferring antiviral drug resistance

TABLE 6

H274Y FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.50 | + | + | + | + | + | + | + |
| 0.10 | + | + | + | + | + | + | − |
| 0.05 | + | + | + | + | + | + | + |
| 0.01 | + | + | + | + | + | + | − |

TABLE 6-continued

| | H274Y FluMAMA | | | | | | |
|---|---|---|---|---|---|---|---|
| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
| 0.005 | + | + | + | + | + | + | − |
| 0.0025 | + | + | + | + | + | − | − |

+ indicates detection of mutation conferring antiviral drug resistance
− indicates no detection of mutation conferring antiviral drug resistance Tables 7 through 11 show the mean calculated resistant:sensitive ratios along with 95% confidence intervals for each mutation at each concentration. Table 13 depicts the lower limit of quantification of mutant using each of the five assays depicted. We then transformed the lower limit of quantification into an absolute copy number equivalent, which is at 25 copies of the targeted mutant in a mixture per 975 copies of antiviral drug sensitive DNA using the L26F, V27A, A30T, H274Y FluMAMA assays and at 50 copies of the targeted mutant in a mixture per 950 copies of antiviral drug sensitive DNA using the S31N FluMAMA. FluMAMA consistently distinguished between 2.5 copies of the mutant (5 copies for S31N FluASMA) and pure sensitive plasmid even at $10^3$ copies/μl DNA concentration.

For all Tables 7-11,
Top number: mean calculated resistant:sensitive ratio. Bottom numbers=95% confidence interval of resistant:sensitive ratio.

TABLE 7

| | L26F FluMAMA | | | | | | |
|---|---|---|---|---|---|---|---|
| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
| 0.50 | 0.588 | 0.584 | 0.472 | 0.495 | 0.465 | 0.438 | 0.462 |
| | 0.570-0.604 | 0.573-0.595 | 0.448-0.497 | 0.455-0.534 | 0.447-0.484 | 0.415-0.461 | 0.401-0.525 |
| 0.10 | 0.0904 | 0.118 | 0.103 | 0.0817 | 0.0757 | 0.0636 | N/A |
| | 0.085-0.097 | 0.112-0.124 | 0.079-0.132 | 0.062-0.108 | 0.070-0.082 | 0.070-0.082 | |
| 0.05 | 0.0420 | 0.055 | 0.054 | 0.039 | 0.033 | 0.035 | 0.055 |
| | 0.039-0.049 | 0.052-0.058 | 0.051-0.058 | 0.031-0.048 | 0.029-0.037 | 0.028-0.044 | 0.048-0.062 |
| 0.01 | 0.0089 | 0.0122 | 0.0126 | 0.0062 | 0.0065 | 0.0058 | N/A |
| | 0.008-0.010 | 0.011-0.014 | 0.012-0.014 | 0.005-0.007 | 0.006-0.008 | 0.004-0.007 | |
| 0.005 | 0.0046 | 0.0056 | 0.0042 | 0.0037 | 0.0043 | NA | NA |
| | 0.004-0.005 | 0.005-0.006 | 0.003-0.006 | 0.003-0.004 | 0.004-0.005 | | |
| 0.0025 | 0.0025 | 0.0025 | 0.0019 | 0.0018 | 0.0014 | NA | NA |
| | 0.002-0.003 | 0.002-0.003 | 0.002-0.002 | 0.002-0.002 | 0.001-0.002 | | |

TABLE 8

| | V27A FluMAMA | | | | | | |
|---|---|---|---|---|---|---|---|
| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
| 0.50 | 0.457 | 0.484 | 0.504 | 0.504 | 0.546 | 0.505 | 0.512 |
| | 0.421-0.493 | 0.465-0.504 | 0.459-0.548 | 0.449-0.558 | 0.515-0.554 | 0.479-0.532 | 0.474-0.550 |
| 0.10 | 0.0777 | 0.0939 | 0.817 | 0.0860 | 0.108 | 0.0975 | 0.0802 |
| | 0.073-0.083 | 0.088-0.100 | 0.065-0.103 | 0.069-0.108 | 0.097-0.120 | 0.078-0.121 | 0.062-0.103 |
| 0.05 | 0.0356 | 0.0496 | 0.0471 | 0.0440 | 0.055 | 0.058 | N/A |
| | 0.032-0.039 | 0.038-0.065 | 0.045-0.049 | 0.038-0.052 | 0.044-0.059 | 0.045-0.073 | |
| 0.01 | 0.0070 | 0.0095 | 0.0088 | 0.0078 | 0.0098 | 0.0095 | 0.0187 |
| | 0.007-0.08 | 0.008-0.011 | 0.008-0.010 | 0.006-0.009 | 0.007-0.012 | 0.007-0.012 | 0.015-0.023 |
| 0.005 | 0.0034 | 0.0050 | 0.0045 | 0.0044 | 0.0051 | NA | NA |
| | 0.003-0.004 | 0.004-0.007 | 0.004-0.005 | 0.004-0.005 | 0.004-0.006 | | |
| 0.0025 | 0.0019 | 0.0023 | 0.0024 | 0.0023 | 0.0026 | NA | NA |
| | 0.002-0.002 | 0.002-0.003 | 0.002-0.003 | 0.002-0.003 | 0.002-0.003 | | |

TABLE 9

| | A30T FluMAMA | | | | | | |
|---|---|---|---|---|---|---|---|
| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
| 0.50 | 0.500 | 0.443 | 0.478 | 0.543 | 0.601 | 0.455 | 0.519 |
| | 0.486-0.514 | 0.414-0.472 | 0.435-0.521 | 0.498-0.588 | 0.566-0.635 | 0.422-0.489 | 0.498-0.540 |
| 0.10 | 0.0988 | 0.0893 | 0.0904 | 0.114 | 0.117 | 0.0823 | 0.105 |
| | 0.094-0.107 | 0.081-0.098 | 0.077-0.106 | 0.083-0.154 | 0.104-0.130 | 0.067-0.100 | 0.086-0.127 |

TABLE 9-continued

A30T FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.05 | 0.0477 | 0.0344 | 0.0438 | 0.0547 | 0.0588 | 0.0386 | N/A |
|  | 0.046-0.050 | 0.031-0.038 | 0.038-0.051 | 0.040-0.074 | 0.051-0.067 | 0.028-0.053 |  |
| 0.01 | 0.0101 | 0.0074 | 0.0095 | 0.0110 | 0.0114 | NA | NA |
|  | 0.010-0.011 | 0.007-0.008 | 0.008-0.011 | 0.008-0.016 | 0.009-0.014 |  |  |
| 0.005 | 0.0061 | 0.0045 | 0.0059 | 0.0056 | 0.0078 | NA | NA |
|  | 0.006-0.007 | 0.004-0.005 | 0.005-0.007 | 0.005-0.006 | 0.006-0.010 |  |  |
| 0.0025 | 0.0040 | 0.0030 | 0.0038 | 0.0037 | 0.0055 | 0.0049 | NA |
|  | 0.004-0.005 | 0.003-0.003 | 0.003-0.005 | 0.003-0.005 | 0.004-0.007 | 0.004-0.005 |  |

TABLE 11

S31N FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.50 | 0.626 | 0.560 | 0.467 | 0.478 | 0.474 | 0.433 | 0.465 |
|  | 0.600-0.650 | 0.496-0.623 | 0.435-0.500 | 0.440-0.515 | 0.455-0.493 | 0.401-0.466 | 0.401-0.531 |
| 0.10 | 0.125 | 0.103 | 0.844 | 0.0797 | 0.084 | 0.0649 | 0.0797 |
|  | 0.113-0.137 | 0.094-0.112 | 0.079-0.090 | 0.068-0.094 | 0.077-0.091 | 0.053-0.080 | 0.072-0.088 |
| 0.05 | 0.0544 | 0.054 | 0.0407 | 0.0407 | 0.0404 | 0.048 | 0.0628 |
|  | 0.052-0.057 | 0.041-0.072 | 0.038-0.044 | 0.033-0.050 | 0.037-0.044 | 0.038-0.059 | 0.054-0.073 |
| 0.01 | 0.0124 | 0.0153 | 0.0106 | 0.0103 | 0.0106 | NA | NA |
|  | 0.012-0.013 | 0.013-0.019 | 0.010-0.012 | 0.009-0.012 | 0.009-0.012 |  |  |
| 0.005 | 0.0067 | 0.0086 | 0.0071 | 0.0067 | 0.0080 | NA | NA |
|  | 0.006-0.007 | 0.007-0.010 | 0.007-0.008 | 0.006-0.008 | 0.007-0.010 |  |  |
| 0.0025 | 0.0049 | 0.0063 | 0.0052 | 0.0048 | NA | NA | NA |
|  | 0.005-0.005 | 0.005-0.008 | 0.005-0.006 | 0.004-0.006 |  |  |  |

TABLE 12

H274Y FluMAMA

| r:s Ratio | $10^9$ copies/μl | $10^7$ copies/μl | $10^5$ copies/μl | $10^4$ copies/μl | $10^3$ copies/μl | $10^2$ copies/μl | $10^1$ copies/μl |
|---|---|---|---|---|---|---|---|
| 0.50 | 0.542 | 0.498 | 0.533 | 0.523 | 0.566 | 0.500 | 0.510 |
|  | 0.499-0.583 | 0.482-0.514 | 0.502-0.563 | 0.447-0.598 | 0.542-0.589 | 0.469-0.531 | 0.428-0.592 |
| 0.10 | 0.0710 | 0.0975 | 0.0957 | 0.0945 | 0.112 | 0.0876 | NA |
|  | 0.062-0.084 | 0.092-0.104 | 0.083-0.111 | 0.080-0.112 | 0.0095-0.131 | 0.068-0.113 |  |
| 0.05 | 0.0356 | 0.0461 | 0.0443 | 0.0443 | 0.0537 | 0.044 | 0.0503 |
|  | 0.030-0.042 | 0.043-0.050 | 0.040-0.049 | 0.034-0.057 | 0.044-0.065 | 0.038-0.050 | 0.043-0.059 |
| 0.01 | 0.0063 | 0.0085 | 0.0093 | 0.0090 | 0.0112 | 0.0088 | NA |
|  | 0.005-0.008 | 0.008-0.009 | 0.009-0.010 | 0.007-0.011 | 0.009-0.013 | 0.007-0.011 |  |
| 0.005 | 0.0034 | 0.0058 | 0.0059 | 0.0061 | 0.0056 | 0.0059 | NA |
|  | 0.003-0.004 | 0.005-0.07 | 0.005-0.007 | 0.005-0.007 | 0.005-0.07 | 0.005-0.007 |  |
| 0.0025 | 0.0031 | 0.0037 | 0.0039 | 0.0039 | 0.0041 | NA | NA |
|  | 0.003-0.004 | 0.004-0.004 | 0.003-0.005 | 0.003-0.005 | 0.003-0.005 |  |  |

The dynamic range of FluMAMA was established at $10^2$-$10^8$ copies/μl. Reaction efficiencies were comparable across assays. Reaction efficiencies ranged from 0.96-1.07 for L26F FluASMA, 1.06-1.30 for V27A, 1.05-1.26 for A30T, 0.95-1.16 for S31N, and 1.11-1.29 for H274Y. The mean percent error for the calculated mutant percentages for all antiviral resistant mutants were assessed for all reactions containing ≥25 copies of the targeted mutant (≥50 copies for S31N FluMAMA). The mean percent error ranged from 7.0-9.9%, with a standard deviation of 4.2-6.8%. Intra-assay CoV for $\Delta Ct_{r-s}$ was also assessed. The mean intra-assay CoV ranged from 1.1-1.7% (Table 12).

TABLE 12

Assay validation per mutant tested.

| Assay | Validated lower limit of quantification[1] | Normalized $\Delta Ct_{r-s}$ | Theoretical lower limit of quantification[2] | % error (SD) of calculated % mutant | ΔCt Intra-run mean CoV | ΔCt Inter-run mean CoV |
|---|---|---|---|---|---|---|
| M2 Gene |  |  |  |  |  |  |
| L26F | 0.25% | 19.0 | $3.8 \times 10^{-4}$% (at $6.6 \times 10^6$ total copies) | 7.0 (4.2) | 1.1% | 3.6% |

TABLE 12-continued

Assay validation per mutant tested.

| Assay | Validated lower limit of quantification[1] | Normalized $\Delta Ct_{r-s}$ | Theoretical lower limit of quantification[2] | % error (SD) of calculated % mutant | ΔCt Intra-run mean CoV | ΔCt Inter-run mean CoV |
|---|---|---|---|---|---|---|
| V27A | 0.25% | 11.2 | 0.1% (at $2.0 \times 10^4$ total copies) | 7.0 (4.6) | 1.2% | 2.2% |
| A30T | 0.25% | 9.5 | 0.25% (at $1.0 \times 10^4$ total copies) | 9.9 (6.8) | 1.6% | 4.5% |
| S31N | 0.5% | 8.5 | 0.5% (at $1.0 \times 10^4$ total copies) | 7.5 (4.8) | 1.3% | 3.0% |
| NA Gene | | | | | | |
| H274Y | 0.25% | 11.5 | 0.05% (at $5.0 \times 10^4$ total copies) | 8.8 (6.6) | 1.7% | 3.0% |

FIGS. 1 through 15 graphically depict the variances replicates for each targeted mutation at each DNA concentration. The figures are further broken down into mutation frequency sets. Samples with a high frequency of mutations that confer drug resistance (50%-100%), samples with a mid-level frequency of mutation (5%-10%), and samples with a C) low frequency of mutation (0%-1%) are further grouped. These data show that the confidence intervals do not overlap at the validated range of detection, indicating that there is 95% confidence that even differences in frequency of resistant alleles in a sample at low frequencies of mutation are real differences.

Table 14 provides a listing of M2 mutations found in influenza samples. While mutations that occur in a different base than the targeted base will not be detected by the specific FluMAMA assays, the assay may be readily adapted to detect other mutations that confer antiviral resistance or to detect antiviral resistance in other strains. For example, a single nucleotide change in the V27A, A30T, and S31N FluMAMA will allow its application to additional H1N1 strains and the H274Y FluMAMA can be to H5N1 strains or to A/Texas/36/91. Re-design and re-validation of FluMAMA would require sequences of the strains or subtypes of interest and a new plasmid standard containing the targeted SNP allele in the strains/subtype of interest.

TABLE 14

Alternative nucleotide substitutions in mutations that confer antiviral sensitivity

| Codon | Sens AA | Sens Seq | Exp. Res AA | Exp. Res Seq | Observed Res AA | Observed Res Seq |
|---|---|---|---|---|---|---|
| 27 | Val (V) | GTT | Ala (A) | GCT | Gly (G) | GGT |
| 27 | Val (V) | GTT | Ala (A) | GCT | Ile (I) | ATT |
| 30 | Ala (A) | GCG | Thr (T) | ACG | Ser (S) | TCG |
| 30 | Ala (A) | GCG | Thr (T) | ACG | Val (V) | GTG |
| 30 | Ala (A) | GCG | Thr (T) | ACG | Glu (E) | GAG |
| 31 | Ser (S) | AGT | Asn (N) | AAT | Ile (I) | ATT |
| 31 | Ser (S) | AGT | Asn (N) | AAT | Gly (G) | GGT |
| 31 | Ser (S) | AGT | Asn (N) | AAT | Arg (R) | AGA |

Figure 16:
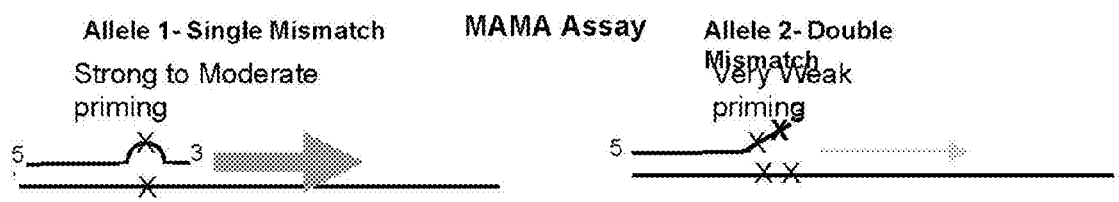
FIG. 16 depicts the principle behind an MAMA assay.
Figure 17:
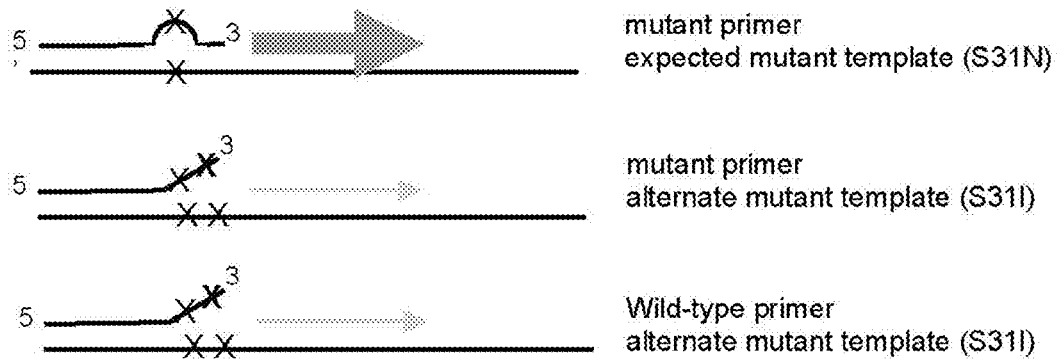
FIG. 17 depicts a situation in which a MAMA assay is unable to quantify the level of a mutation other than a target mutation with a primer that hybridizes to a target mutation.

Of the eight alternate mutations seen in previous experiments, only three occur at the same base location. The MAMA assays target a specific base and rely on a difference in the amplification efficiency between a single mismatch and two mismatches between the primer and template DNA. FIG. 16 graphically depicts this principle. FIG. 17 shows that in the case of an alternate mutation at the same base location, there would be no difference in the amplification between the mutant that confers antiviral resistance and the antiviral sensitive form (which is interchangeably referred to as wild-type), because both contain a double mismatch. However, by using a pre-screen with HRM and targeted Sanger sequencing on a subset of samples, it is possible to determine which FluMAMA assay to use to detect antiviral resistant mutations.

Once a predominant mutation in a given experiment is determined, highly accurate and precise measures of the minor component mutant population can be achieved. To appropriately apply FluMAMA, it is necessary to know the sequence of the influenza being tested to ascertain if it was a perfect match for the primers and probes used in FluMAMA. As a result, users may sequence the samples being tested against FluMAMA prior to running the assays.

Table 15 provides a list of SEQ ID numbers correlated with the sequences that they represent.

TABLE 1

Sequence codes

| Oligo Name | Sequence ID |
|---|---|
| L26F R | SEQ ID NO. 1 |
| L26F F-Sensitive | SEQ ID NO. 2 |
| L26F F-Resistant | SEQ ID NO. 3 |
| L26F Probe | SEQ ID NO. 4 |
| V27A/S31N F | SEQ ID NO. 5 |
| V27A R-Sensitive | SEQ ID NO. 6 |
| V27A R-Resistant | SEQ ID NO. 7 |
| V27A/S31N Probe | SEQ ID NO. 8 |
| A30T F | SEQ ID NO. 9 |
| A30T R-Sensitive | SEQ ID NO. 10 |
| A30T R-Resistant | SEQ ID NO. 11 |
| A30T Probe | SEQ ID NO. 12 |
| S31N R-Sensitive | SEQ ID NO. 13 |
| S31N R-Resistant | SEQ ID NO. 14 |
| H274Y F | SEQ ID NO. 15 |
| H274Y R-Sensitive | SEQ ID NO. 16 |
| H274Y R-Resistant | SEQ ID NO. 17 |
| H274Y Probe | SEQ ID NO. 18 |
| Influenza A M2 Protein | SEQ ID NO. 19 |
| Influenza A M2 nucleic acid | SEQ ID NO. 20 |
| Influenza A Neuraminidase protein | SEQ ID NO. 21 |
| Influenza A neuraminidase nucleic acid | SEQ ID NO. 22 |

References

So as to reduce the complexity and length of the Detailed Specification, Inventors herein expressly incorporate by reference all of the following materials. Inventors believe that the incorporated material is "non-essential" in accordance with 37 CFR 1.57, because it is referred to for purposes of enabling the invention and/or illustrating the state of the art. However, if the Examiner believes that any of the above-incorporated material constitutes "essential material" within the meaning of 37 CFR 1.57(c)(1)-(3), Inventors will amend the specification to expressly recite the essential material that is incorporated by reference as allowed by the applicable rules.

1. Li B et al, *Genomics* 83, 311-320 (2004).
2. Germer S et al, *Genome Res* 10, 258-266 (2000).
3. Sidwell R W et al, *Antiviral Res* 68, 10-17 (2005).
4. McSharry J J et al, *Clin Diag Lab Immunol* 11, 21-28 (2004).
5. Sidwell R W and Smee D F, *Antiviral Res* 48, 1-16 (2000).
6. Mungall B A et al, *Avian Dis* 47, 3 Suppl 1141-1144 (2003).
7. Gubareva L V et al, *J Gen Virol* 83, 2683-2692 (2002).
8. Hata M et al, *Jpn J Infect Dis* 60, 202-204 (2007).
9. Suwannakarn K et al, *J Virol Methods* 152, 25-31 (2008).
10. Carr M J et al, *J Virol Methods* 153, 257-262 (2008).
11. Duwe S and Schweiger B *J Virol Methods* 153, 134-141 (2008).
12. Deyde V M et al *Antiviral Res* 81, 16-24 (2008.)
13. Rahman M et al, *Diagn Microbiol Infect Dis* 62, 162-166 (2007).
14. Lu Y Y et al, *Lett Appl Microbiol* 46, 20-25 (2007).
15. Rowley C F et al, *J Virol Methods* 149, 69-75 (2008).
16. Peuchant O et al, *AIDS* 31, 1417-1423 (2008).
17. Schwarz G et al, *Nucleic Acids Res* 11, e24 (2004).
18. Norton N et al, *Hum Genet.* 110, 471-478 (2002).
19. Archambeault et al, *Blood* 111, 1124-1127 (2007).
20. Ottone T et al, *J Mol Diagn* 10, 212-216 (2008).
21. Hirt C et al, *Br. J. Haematol* 141, 631-640 (2008).

---

We claim:

1. A method of determining the amount of Influenza A virus resistant to a first and a second antiviral composition in a sample, the sample comprising a mixture of Influenza A virus particles that may be resistant or sensitive to the first and the second antiviral compositions, the method comprising:

subjecting a first amplification mixture to nucleic acid amplification wherein the mixture comprises the sample and a first oligonucleotide capable of binding to a first marker having a sequence of SEQ ID NO. 20, wherein the first oligonucleotide amplifies wild-type and mutant alleles of the first marker with different amplification efficiencies, wherein the different amplification efficiencies arise from a mismatch nucleotide sequence between the first oligonucleotide and the wild-type or mutant alleles of the first marker;

determining a difference between a Ct value of Influenza A virus resistant to the first antiviral composition ($Ct_{mut}$) and a Ct value of Influenza A virus sensitive to the first antiviral composition ($Ct_{wt}$) in the first mixture to determine a $\Delta Ct_{mut-wt}$, value for the first mixture;

subjecting a second amplification mixture to nucleic acid amplification wherein the mixture comprises the sample and a second oligonucleotide capable of binding to a second marker having a sequence of SEQ ID NO. 22, wherein the second oligonucleotide amplifies wild-type and mutant alleles of the second marker with different amplification efficiencies, wherein the different amplification efficiencies arise from a mismatch nucleotide sequence between the first oligonucleotide and the wild-type or mutant alleles of the second marker;

determining a difference between a Ct value of Influenza A virus resistant to the second antiviral composition ($Ct_{mut}$) and a Ct value of Influenza A virus sensitive to the second antiviral composition ($Ct_{wt}$) in the second mixture to determine a $\Delta Ct_{mut-wt}$ value for the second mixture;

determining the amount of Influenza A virus resistant to the first and second antiviral compositions (% mutant) in the first and second mixtures, respectively, with the equation:

$$\%\ \text{mutant}=1/(2^{\Delta Ctmut\text{-}wt}+1)\times 100;$$

wherein the amount of Influenza A virus resistant to the first and second antiviral compositions in the first and second mixtures, respectively, is used to determine which antiviral compositions are effective against the Influenza A virus in the sample;

wherein the first oligonucleotide added to the first mixture includes a sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, and SEQ ID NO. 14;

wherein the first oligonucleotide added to the second mixture includes a sequence selected from the group consisting of SEQ ID NO. 15, SEQ ID NO. 16, SEQ ID NO. 17, and SEQ ID NO. 18; and wherein the sample comprises a nucleic acid.

2. The method of claim 1 wherein the first oligonucleotide added to the first mixture includes SEQ ID NO. 1, further comprising adding a second oligonucleotide to the first mixture.

3. The method of claim 2 wherein the second oligonucleotide includes a sequence selected from the group consisting of SEQ ID NO. 2 and SEQ ID NO. 3.

4. The method of claim 3 further comprising adding a third oligonucleotide to the first mixture, wherein the third oligonucleotide includes SEQ ID NO. 4.

5. The method of claim 4 wherein the second oligonucleotide includes SEQ ID NO. 2 further comprising adding a fourth oligonucleotide to the first mixture, wherein the fourth oligonucleotide includes SEQ ID NO.3.

6. The method of claim 1 wherein the first oligonucleotide added to the first mixture includes SEQ ID NO. 5, further comprising adding a second oligonucleotide to the first mixture.

7. The method of claim 6 wherein the second oligonucleotide includes a sequence selected from the group consisting of SEQ ID NO. 6, SEQ ID NO. 7, SEQ ID NO. 13, and SEQ ID NO. 14.

8. The method of claim 7 further comprising adding a third oligonucleotide to the first mixture, wherein the third oligonucleotide includes SEQ ID NO. 8.

9. The method of claim 8 wherein the second oligonucleotide includes SEQ ID NO. 6 further comprising adding a fourth oligonucleotide to the first mixture, wherein the fourth oligonucleotide includes SEQ ID NO. 7.

10. The method of claim 8 wherein the second oligonucleotide includes SEQ ID NO. 13 further comprising adding a fourth oligonucleotide to the first mixture, wherein the fourth oligonucleotide includes SEQ ID NO. 14.

11. The method of claim 1 wherein the first oligonucleotide includes SEQ ID NO. 9, further comprising adding a second oligonucleotide to the first mixture.

12. The method of claim 11 wherein the second oligonucleotide includes a sequence selected from the group consisting of SEQ ID NO. 10 and SEQ ID NO. 11.

13. The method of claim 12 further comprising adding a third oligonucleotide to the first mixture, wherein the third oligonucleotide includes SEQ ID NO. 12.

14. The method of claim 13 wherein the second oligonucleotide includes SEQ ID NO. 10 further comprising adding a fourth oligonucleotide to the first mixture, wherein the fourth oligonucleotide includes SEQ ID NO. 11.

15. The method of claim 1 wherein the first oligonucleotide added to the second mixture includes SEQ ID NO. 15, further comprising adding a second oligonucleotide to the second mixture.

16. The method of claim 15 wherein the second oligonucleotide includes a sequence selected from the group consisting of SEQ ID NO. 16 and SEQ ID NO. 17.

17. The method of claim 16 further comprising adding a third oligonucleotide to the second mixture, wherein the third oligonucleotide includes SEQ ID NO. 18.

18. The method of claim 17 wherein the second oligonucleotide includes SEQ ID NO. 16 further comprising adding a fourth oligonucleotide to the second mixture, wherein the fourth oligonucleotide includes SEQ ID NO. 17.

19. The method of claim 1 wherein at least one of the first oligonucleotide added to the first mixture and the first oligonucleotide added to the second mixture comprises a first label.

20. The method of claim 19 wherein the first label comprises a fluorescent label.

21. The method of claim 20 wherein the first oligonucleotide is selected from the group consisting of SEQ ID NO. 4, SEQ ID NO. 8, SEQ ID NO. 12, and SEQ ID NO. 18.

22. The method of claim 20 wherein the fluorescent label is selected from the group consisting of FAM, dR110, 5-FAM, 6FAM, dR6G, JOE, HEX, VIC, TET, dTAMRA, TAMRA, NED, dROX, PET, BHQ+, Gold540, and LIZ.

23. The method of claim 1 wherein the first oligonucleotide added to the first mixture is selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, and SEQ ID NO. 14 and the first antiviral composition comprises an adamantine.

24. The method of claim 1 wherein the first oligonucleotide added to the second mixture is selected from the group consisting of SEQ ID NO. 15, SEQ ID NO. 16, SEQ ID NO. 17, and SEQ ID NO. 18 and the second antiviral composition comprises a neuraminidase inhibitor.

25. The method of claim 1 wherein the sample comprises an environmental sample.

26. The method of claim 1 wherein the sample comprises a sample derived from a subject.

27. The method of claim 26 wherein the sample comprises a sputum sample.

28. The method of claim 1 further comprising collecting the sample.

29. The method of claim 1, wherein the nucleic acid amplification is quantitative PCR (qPCR).

* * * * *